(12) United States Patent
Wang et al.

(10) Patent No.: US 12,161,635 B2
(45) Date of Patent: Dec. 10, 2024

(54) COMPOSITIONS AND METHODS OF TREATING PIK3CA HELICAL DOMAIN MUTANT CANCERS

(71) Applicant: CASE WESTERN RESERVE UNIVERSITY, Cleveland, OH (US)

(72) Inventors: Zhenghe Wang, Beachwood, OH (US); Yujun Hao, Shanghai (CN); Yamu Li, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 17/559,280

(22) Filed: Dec. 22, 2021

(65) Prior Publication Data
US 2022/0193056 A1  Jun. 23, 2022

Related U.S. Application Data

(60) Provisional application No. 63/129,339, filed on Dec. 22, 2020.

(51) Int. Cl.
*A61K 31/4439* (2006.01)
*A61K 45/06* (2006.01)
*A61P 35/00* (2006.01)

(52) U.S. Cl.
CPC .......... *A61K 31/4439* (2013.01); *A61K 45/06* (2013.01); *A61P 35/00* (2018.01)

(58) Field of Classification Search
CPC .............. A61K 31/4439; A61K 31/496; A61K 31/5377; A61K 45/06; A61K 2300/00; A61P 35/00
See application file for complete search history.

(56) References Cited

U.S. PATENT DOCUMENTS

| | | | |
|---|---|---|---|
| 2017/0051361 A1* | 2/2017 | Moynahan | ............... C12Q 1/68 |
| 2019/0151325 A1 | 5/2019 | Raimondi | |
| 2020/0135302 A1 | 4/2020 | Bagaev et al. | |
| 2021/0069230 A1 | 3/2021 | Rees et al. | |
| 2021/0115140 A1 | 4/2021 | Cao et al. | |

OTHER PUBLICATIONS

Gymnopoulos et al., Rare cancer-specific mutations in PIK3CA show gain of function, PNAS, vol. 104, No. 13, 5569-5574, Mar. 27, 2007 (Year: 2007).*

* cited by examiner

Primary Examiner — Kortney L. Klinkel
Assistant Examiner — Padmaja S Rao
(74) Attorney, Agent, or Firm — Tarolli, Sundheim, Covell & Tummino LLP

(57) ABSTRACT

A method of treating PIK3CA helical domain mutant cancer in a subject in need thereof includes administering to the subject therapeutically effective amounts of (i) an inhibitor of nuclear translocation of p85β and/or an EZH inhibitor in combination with (ii) a PI3K inhibitor.

6 Claims, 43 Drawing Sheets a b h i j a
p85β WT         QELQMKRTAIEAFNE
p85β^(KR-AA) Mut  QELQMAATAIEAFNE
positions: 474, 477, 478, 484
Fig. 4A
b
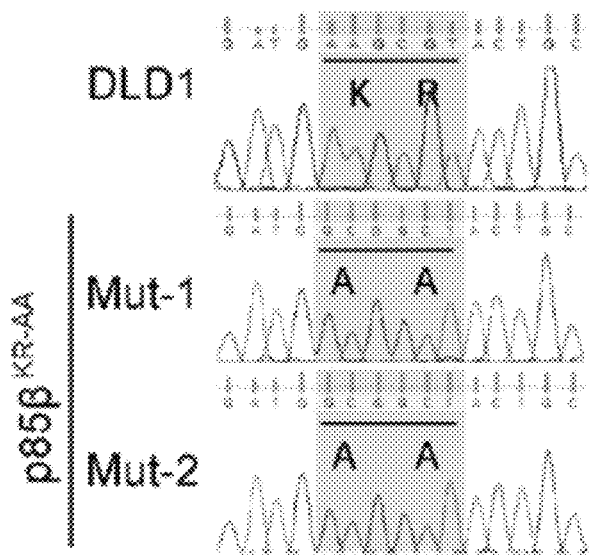
Fig. 4B
c
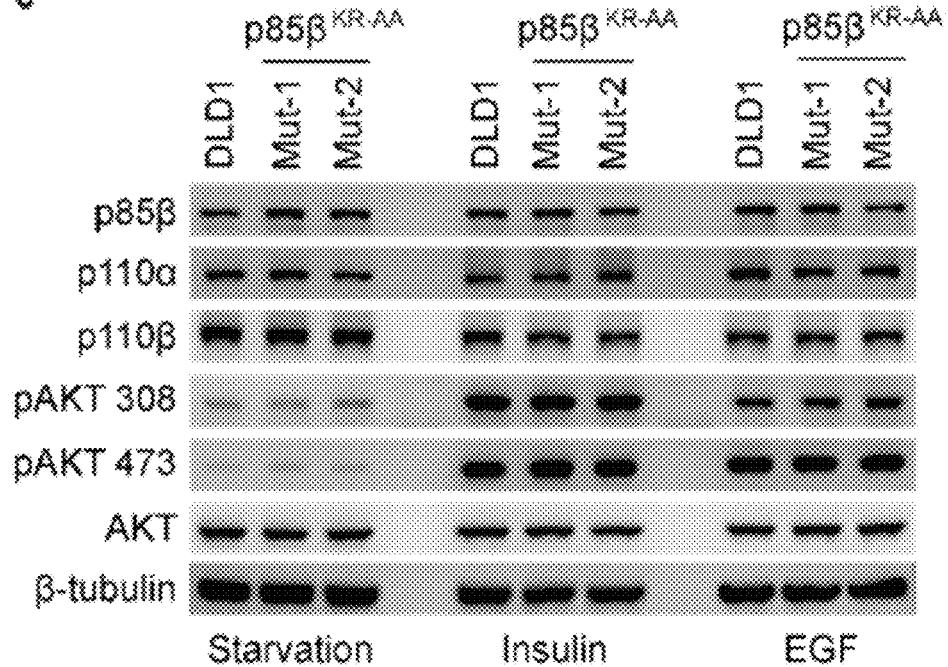
Fig. 4C c d

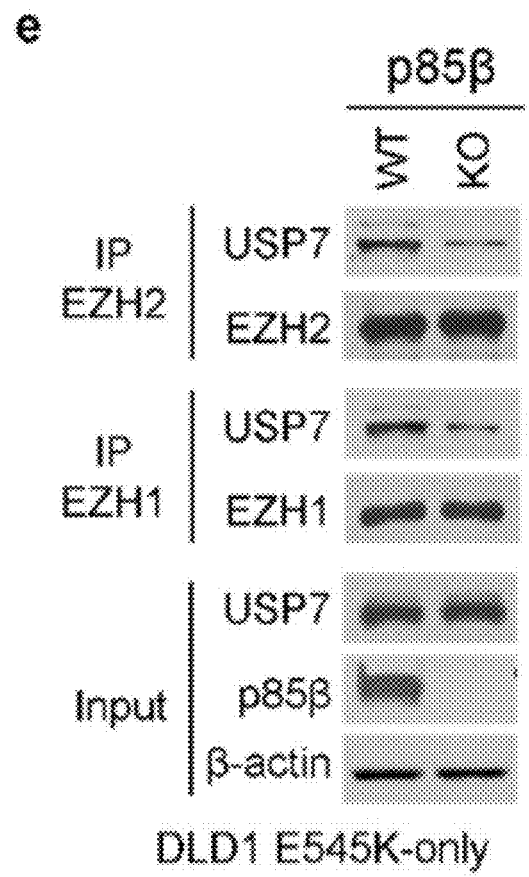
Fig. 5E
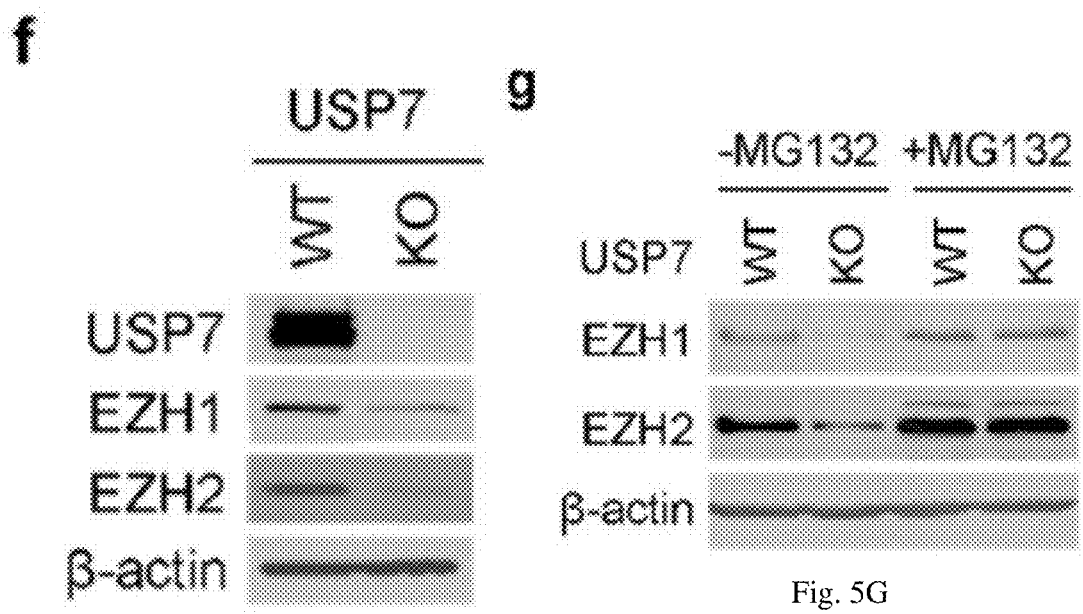
Fig. 5F
Fig. 5G

COMPOSITIONS AND METHODS OF TREATING PIK3CA HELICAL DOMAIN MUTANT CANCERS

RELATED APPLICATION

This application claims priority from U.S. Provisional Application No. 63/129,339, filed Dec. 22, 2020, the subject matter of which is incorporated herein by reference in its entirety.

GOVERNMENT FUNDING

This invention was made with government support under Grant No. R01CA196643 awarded by The National Institutes of Health. The United States government has certain rights in the invention.

BACKGROUND

PIK3CA, which encodes the p110α catalytic subunit of PI3 kinase, is one of the most frequently mutated oncogenes in human cancers. Recently, the FDA approved the combination of p110α-specific inhibitor Alpelisib and the estrogen receptor antagonist Fulvestrant to treat PIK3CA-mutant breast cancer patients whose tumors are hormone receptor (HR)-positive and HER2-negative. This approval highlights mutant PIK3CA (encoding p110α protein) as a critical cancer drug target and the importance of further understanding the molecular mechanisms by which PIK3CA mutations drive tumorigenesis. PI3Ks are heterodimers consisting of a p110 catalytic subunit and a p85 regulatory subunit. Normally, the p85 subunits bind and stabilize the p110 subunit and inhibit its enzymatic activity. Upon growth factor stimulation, the SH2 domains of p85 bind to the phospho-tyrosine residues on receptor protein kinases or adaptor proteins, such as insulin receptor substrate 1 (IRS1), which activates PI3K and catalyzes the conversion of phosphatidylinositol-4,5-bisphosphate (PIP2) to phosphatidylinositol-3,4,5-triphosphate (PIP3). PIP3 recruits pleckstrin homology domain-containing proteins, including PDK1 and AKTs, to the cell membrane to activate signaling pathways.

SUMMARY

Embodiments described herein relate to compositions and methods of treating PIK3CA helical domain mutant cancer in a subject in need thereof. PI3Ks consist of p110 catalytic subunits and p85 regulatory subunits. PIK3CA, encoding p110α, is frequently mutated in human cancers. Most PIK3CA mutations are clustered in two hotspots: the helical domain and the kinase domains. It was found that in cancer cells with a p110α helical domain mutation, p85β, but not p85α, disassociates from p110α helical domain mutant protein and translocates into the nucleus through a nuclear localization sequence (NLS), thereby promoting tumor growth. The nuclear p85β recruits deubiquitinase USP7 to stabilize histone methyltransferases EZH1 and EZH2 and enhances histone H3 lysine 27 trimethylation (H3K27Me3). We had previously found that p110α helical domain mutant proteins directly bind to IRS1 and activate the canonical PDK1-AKT signaling pathways. Therefore, PIK3CA helical domain mutations promote oncogenesis through two independent pathways: a canonical p110-PDK1-AKT pathway and a nuclear p85β-USP7-EZH1/2 axis.

It was found that simultaneously targeting p85β-stabilized EZHs and p110α reduces the growth of tumors harboring PIK3CA helical domain mutations, but not tumors with PIK3CA WT or kinase domain mutations. Inhibiting or blocking nuclear translocation of p85β and/or administering an EZH inhibitor sensitizes PIK3CA helical domain mutant cancers to p110α inhibitors, suggesting that targeting p85β nuclear translocation in combination with a p110α inhibitor can be an effective therapeutic approach for PIK3CA helical domain mutant cancers or tumors. Accordingly, in some embodiments described herein, a method of treating PIK3CA helical domain mutant cancer in a subject in need thereof includes administering to the subject therapeutically effective amounts of (i) an inhibitor of nuclear translocation of p85β and/or an EZH inhibitor in combination with (ii) a PI3K inhibitor.

In some embodiments, the inhibitor of nuclear translocation of p85β is an inhibitor of transport receptor importin-beta, such as importazole.

In other embodiments, the EZH inhibitor includes at least one of EPZ011989 (free base CAS No. 1598383-40-4), EPZ005687 (CAS No. 1396772-26-1), GSK126 (CAS No. 1346574-57-9), GSK343 (CAS No. 1346704-33-3), GSK503 (CAS No. 1346572-63-1), tazemetostat (EPZ-6438, CAS No. 1403254-99-8), 3-deazaneplanocin A (DZNeP, HCl salt CAS No. 120964-45-6), EI1 (CAS No. 1418308-27-6), CPI-360 (CAS No. 1802175-06-9), CPI-169 (CAS No. 1450655-76-1), JQ-EZ-05 (JQEZ5, CAS No. 1913252-04-6), PF-06726304 (CAS No. 1616287-82-1), UNC1999 (CAS No. 1431612-23-5), UNC2400 (CAS No. 1433200-49-7) or analogs thereof.

In other embodiments, the PI3K inhibitor includes at least one of pictilisib, dactolisib, wortmannin, LY294002, Idelalisib, duvelisib, buparlisib, IPI-549, SP2523, GDC-0326, TGR-1202, VPS34 inhibitor 1, GSK2269557, GDC-0084, SAR405, AZD8835, LY3023414, PI-103, TGX-221, NU7441, IC-87114, wortmannin, XL147 analogue, ZSTK474, Alpelisib, PIK-75 HCl, A66, AS-605240, 3-Methyladenine (3-MA), PIK-93, PIK-90, AZD64822, PF-04691502, Apitolisib, GSK1059615, Duvelisib, Gedatolisib, TG100-115, AS-252424, BGT226, CUDC-907, AS-604850, PIK-294, GSK2636771, Copanlisib, YM201636, CH5132799, CAY10505, PIK-293, PKI-402, TG100713, VS-5584, Taselisib, CZC24832, AMG319, GSK2292767, HS-173, Quercetin, Voxtalisib, PIK-93, Omipalisib, PIK-90, GNE-317, Pilaralisib, PF-4989216, AZD8186, 740 Y-P, Vps34-IN1, PIK-III, PI-3065 or analogs thereof.

In still other embodiments, the PI3K inhibitor includes a p110α inhibitor, such as a selective p110α inhibitor. The selective p110α inhibitor can include Alpelisib.

In some embodiments, the PIK3CA helical domain mutant cancer includes a mutation in the p110α helical domain. The mutation can include at least of a mutation of residues E542, E545, or Q546 of the p110α helical domain.

In other embodiments, the cancer includes at least one of breast cancer, colon cancer, colorectal cancer, endometrial cancer, brain cancer, skin cancer, ovarian cancer, gastric cancer, lung cancer, thyroid cancer, head and neck cancer, cervical cancer, pancreatic cancer, esophageal cancer, liver/biliary cancer tract cancer, pituitary tumors, urological tumors, leukemia/lymphoma, or neuroblastoma.

Figure 1A:
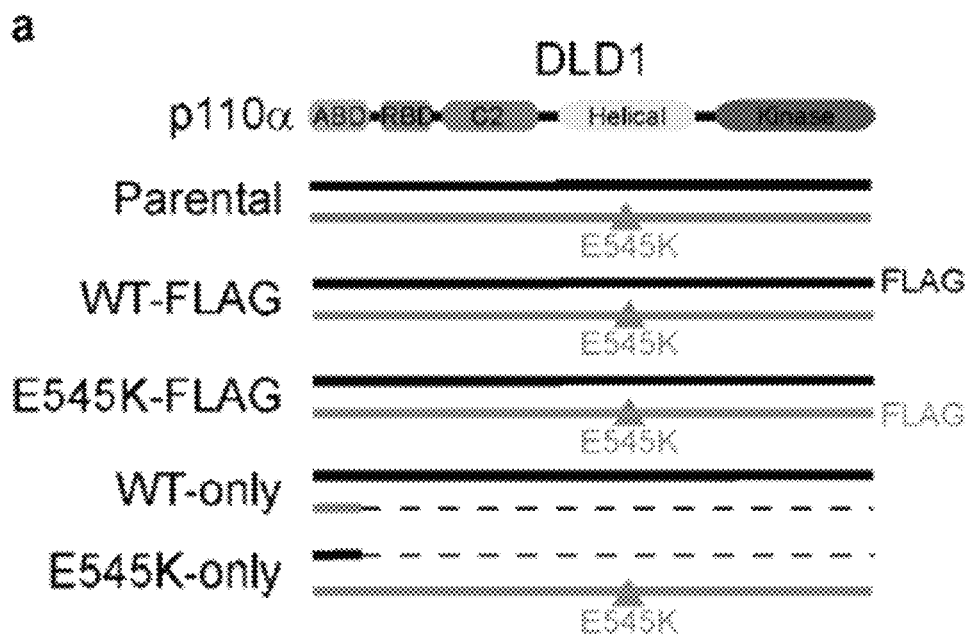
FIGS. 1 (A-J) illustrate p85β disassociates from the p110α helical domain-mutant protein. (A) Schematic of DLD1 isogenic cell lines. WT-FLAG: DLD1 cells with the endogenous wild-type p110α tagged with 3×FLAG; E545K-

FLAG: DLD1 cells with the endogenous p110α E545K mutant protein tagged with 3×FLAG; WT-only: DLD1 cells with the PIK3CA E545K allele knocked out; E545K-only: DLD1 cells with the PIK3CA WT allele knocked out. ABD: adaptor-binding domain; RBD: Ras-binding domain; C2: C2 domain; helical: helical domain; kinase: kinase domain. (B-D) p85β, but not p85α, disassociates from p110α E545K mutant protein. Cell lysates from the p110α E545K or WT FLAG-tagged cells were immunoprecipitated with anti-FLAG antibody-conjugated beads and blotted with indicated antibodies (B). Cell lysates from the indicated cell lines were immunoprecipitated with either an anti-p85β antibody (C) or an anti-p85α antibody (D) and blotted with indicated antibodies. (E) A schematic diagram of tumor-derived PIK3CA mutations tested for interaction with p85β. (F) p85β, but not p85α, disassociates from p110α helical domain mutant proteins. The indicated FLAG-tagged p110α constructs were transfected into 293T cells. Cell lysates were immunoprecipitated by anti-FLAG agarose and then blotted with the indicated antibodies. (G & H) p85β disassociates from PI3K complexes in PIK3CA helical domain mutant cells. Cell lysates from indicated cell lines were immunoprecipitated with either an anti-p85β antibody (G) or an anti-p110α antibody (H) and blotted with indicated antibodies. (I & J). The N-terminal domains of p85β cause disassociation from p110α E545K mutant protein. Schematics of p85α, p85β and two chimeric p85 constructs (I). The indicated HA-tagged p85 constructs were co-transfected with a Flag-tagged construct expressing either WT or E545K mutant p110α. Cell lysates were immunoprecipitated by anti-FLAG agarose and then blotted with an anti-HA antibody.

FIGS. 2(A-I) illustrate p85β plays an oncogenic role in cancer cells with PIK3CA helical domain mutations. (A) High levels of PIK3R2 (p85β) are associated with worse survival of patients whose tumors harbor a PIK3CA helical domain mutation. COAD, BLCA, UCEC, and BRAC datasets were downloaded from TGCA and combined. Patients were divided into three groups according to their PIK3CA mutation status: Helical domain mutations, Non-helical domain mutations, and wild-type. Kaplan-Meier analyses of 5-year survival of patients whose tumors expressing high levels of PIK3R2 vs low levels of PIK3R2 were performed. HR: Hazard Ratio. (B-F) Knockout of p85β impairs the growth of cancer cells with a PIK3CA E545K mutation, but not cells with WT PIK3CA. PIK3R2 (p85β) was knocked out in the indicated cell lines, and the cells were assayed for: Western blot analyses of p85β, p110α and p110β proteins (B); cell proliferation (C); colony formation (D); and xenograft tumor growth (E & F). (G-I) Depletion of p85β impairs the growth of cancer cells with a PIK3CA E545K mutation, but not cells with a PIK3CA H1047R mutation. p85I3 was knocked down with two independent siRNAs in the indicated cell lines, and the cells were assayed for: Western blot analyses of p85I3 protein (G); cell proliferation (H); colony formation (I). Statistical analyses, two-way ANOVA was used for C, E, F & H, and student's t-test was used for D & I. Data are presented as mean±SEM of three independent experiments. p<0.01; *p<0.001; n.s., not significant FIGS. 3(A-J) illustrate p85I3 translocates into the nucleus in cancer cells with a PIK3CA E545K mutation. (A-C) p85β translocates into the nucleus in DLD1 PIK3CA E545K cells. (A) The indicated cells were immunofluorescently stained with an anti-p85I3 antibody and DAPI. (B) Cell lysates were fractionated into cytoplasmic (Cyto) and nuclear (Nuc) fractions and blotted with the indicated antibodies. Whole: whole cell lysate. The ratios of nuclear/cytoplasmic p85β levels were quantified by Image J as shown in (C). Data are presented as mean±SEM of three independent experiments. ***p<0.001; n.s., not significant. (D-J) p85β translocates into the nucleus in cancer cells with a PIK3CA helical domain mutation, but not cells with WT PIK3CA or a PIK3CA kinase domain mutation. The indicated cells were immunofluorescently stained with an anti-p85β antibody, and representative images are shown in (D), (F), and (H). Cell lysates of the indicated cells were fractionated into cytoplasmic and nuclear fractions and blotted with the indicated antibodies (E), (G), and (I). The ratios of nuclear/cytoplasmic p85β levels were quantified by Image J and shown in (J). Data are presented as mean±SEM of three independent experiments.

FIGS. 4(A-G) illustrate nuclear translocation of p85β is critical for the tumorigenicity of PIK3CA E545K mutant cells. (A) A predicted Nuclear Localization Sequence (NLS) in p85β protein is highlighted. The critical stretch basic amino acids $K^{477}R^{478}$ are highlighted. (B) Genomic DNA sequencing of DLD1 parental cells and $K^{477}A R^{478}A$ mutant knock-in (p85β KR-AA) cells. (C) NLS mutation has no impact on p85β, p110α and p110β protein levels and AKT phosphorylation. Cells of the indicated genotypes were serum-starved, stimulated with insulin or EGF, and then lysed and blotted with indicated antibodies. (D) Cells of the indicated genotype were stained with an anti-p85β antibody. Mut-1 and Mut-2 are two independently derived p85β KR-AA mutant knock-in clones. (E-G) Cells of the indicated genotypes were assayed for cell proliferation (E), colony formation (F), and xenograft tumor growth (G). Statistical analyses, two-way ANOVA was used for E & G, and student's t-test was used for F. Data are presented as mean±SEM of three independent experiments. p<0.01; *p<0.001.

FIGS. 5(A-H) illustrate Nuclear p85β recruits the deubiquitinase USP7 to stabilize EZH1/2, increasing H3K27 tri-methylation. (A-C) Nuclear p85β stabilizes EZH1 and EZH2 and increases histone H3K27 methylation. H3K27me3, EZH1, and EZH2 levels were evaluated by Western blot analyses in indicated cell lines. (D) Nuclear p85β interacts with USP7, EZH1, and EZH2. DLD1 cells were lysed and immunoprecipitated (IP) with either an anti-p85β or an anti-USP7 antibody, then blotted with indicated antibodies. (E) The interaction between USP7 and EZH1 or EZH2 is reduced in p85β knockout cells. The indicated cell lines were lysed, IPed with either EZH1 or EZH2, then blotted with indicated antibodies. (F-H) Deubiquitinase USP7 protects EZH1 and EZH2 from ubiquitin-mediateddegradation. Lysates of DLD1 parental cells and USP7 knockout cells were blotted with indicated antibodies (F). DLD1 parental cells and USP7 knockout cells were treated with either vehicle or MG132 for 6 hours and then blotted with indicated antibodies (G). After treated with MG132 for 6 hours, DLD1 parental cells and USP7 knockout cells were lysed, IPed with an antibody against either EZH1 or EZH2, then blotted with indicated antibodies (H).

FIGS. 6(A-H) illustrate a combination of p110α and EZH inhibitors induces regression of tumors with PIK3CA helical domain mutations, but not WT or kinase domain mutation. (A) Subcutaneous xenograft tumors established from DLD1 cells were treated with vehicle or the indicated drugs. GSK2814126: an EZH2 inhibitor; Alpelisib: a p110α-specific inhibitor. (B to G) Tumors are treated with an EZH inhibitor Tazematostat (EPZ-6438), Alpelisib, or the drug combination. Subcutaneous xenograft tumors established from DLD1 parental cells (B), DLD1 PIK3CA E545K-only cells (C), DLD1 PIK3CA WT-only cells (D); a CRC patient-derived xenograft (PDX) with a PIK3CA H1047R kinase domain mutation (E), Vaco481 CRC cells with a PIK3CA Q546P mutation, or a CRC PDX with a PIK3CA E542K mutation (G). Lysates of PIK3CA E542K mutant PDX tumors treated with the indicated drug were blotted with the indicated antibodies. Statistical analyses, two-way ANOVA. *p<0.05; *P<0.001; **P<0.0001; NS, not significant.

Figure 7:
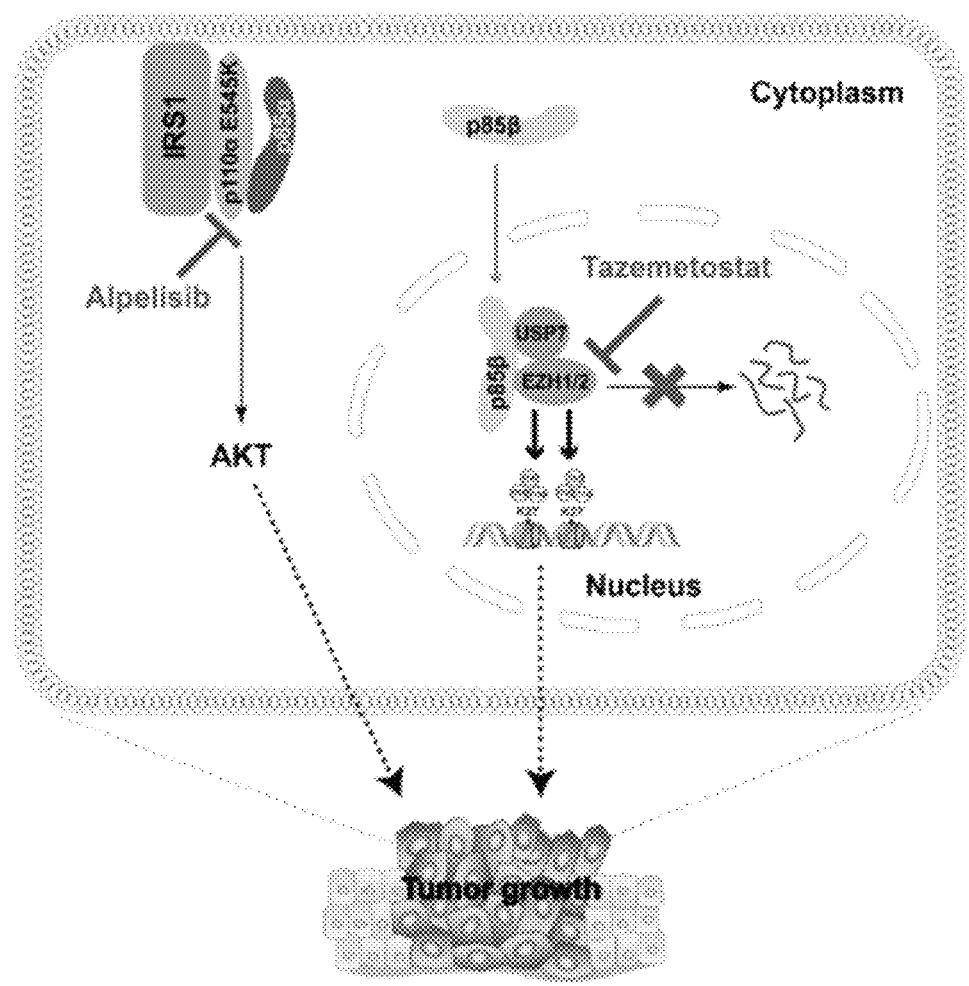

FIG. 7 A model for how PIK3CA helical domain mutations promote oncogenesis. PIK3CA helical domain mutations promote oncogenesis through two independent pathways: (1) p110α helical domain mutant protein directly interacts with IRS1 to activate the canonical PDK1-AKT pathway (citation); and (2) p85β translocates into the nucleus, stabilizes EZH1/2 by recruiting deubiquitinase USP7, and enhances H3K27 trimethylation. Simultaneously targeting both pathways with Alpelisib, a p110α inhibitor, and Tazemetostat, an EZH2 inhibitor, induces regression of tumors harboring a PIK3CA helical domain mutation.

Figure 1B:
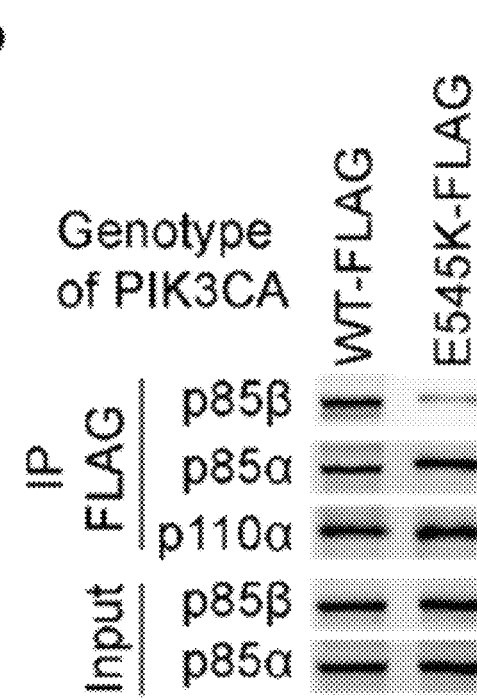
Figure 1C:
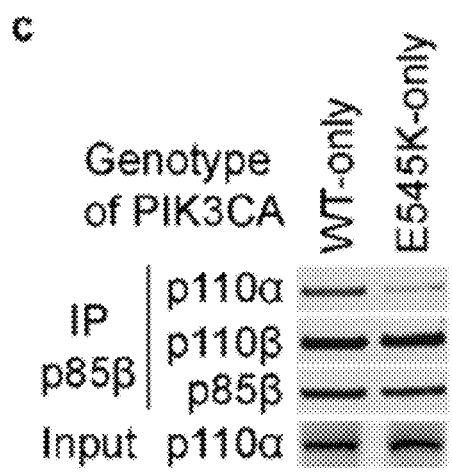
Figure 1D:
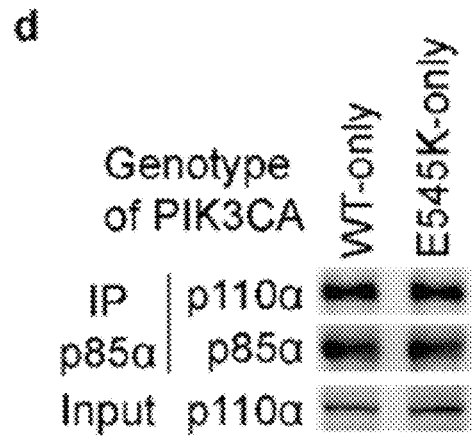

FIGS. 8(A-H) illustrate p85β disassociates from p110α helical domain mutated PI3K complex (A) Quantification of Western blots shown in FIG. 1b by Image J. (B) Quantification of Western blot shown in FIG. 1C by Image J. (C) Quantification of Western blot shown in FIG. 1D by Image J. (D & D) PIK3CA helical domain mutant cells have more p110-free p85β. (D) Cell lysates were immunoprecipitated with both anti-p110α and anti-p110α antibodies and blotted with indicated antibodies. Pre-IP indicates cell lysates before immunoprecipitation; Post-IP indicates cell lysates after immunoprecipitation; Wash indicates buffers after washing beads; IP: p110α+p110α indicates immune complexes on the beads after immunoprecipitation. (E) Indicated cell lysates were fractionated with a Sepharose 6B column. The indicated elution fractions were blotted with the indicated antibodies, and the intensities of each protein at the indicated fractions were quantified with the Image J software. (F) Quantification of Western blot shown in FIG. 1F by Image J. (G) Quantification of Western blot shown in FIG. 1G by Image J. (H) Quantification of Western blot shown in FIG. 1H by Image J.

FIGS. 9(A-H) illustrate the depletion of p85β specifically impairs the growth of cancer cells with a PIK3CA helical domain mutation. (A) PIK3R2 expression levels are higher in tumors compared to corresponding non-tumor tissue (NT). The RNA-seq data of tumors and matched non-tumor tissue were downloaded from the TCGA website. COAD: colon adenocarcinoma; BLCA: bladder carcinoma; UCEC: endometrial carcinoma; BRCA: breast cancer; FPKM: fragments per kilobase of exon per million reads mapped. (B-G) Attenuating of p85β impair the growth of cancer cells a PIK3CA E545K mutation, but not cells with a PIK3CA H1047R mutation or wild-type PIK3CA. p85β was knocked down with siRNA in the indicated cell lines, and the cells were assayed for: Western blot analyses of p85β protein (A, E); cell proliferation (C, F); colony formation (D, G). (H) Mutation status of the indicated genes in cell lines used in this study. The data were obtained from COSMIC. NA: the indicated information is not available. The student's t-test was used for statistical analyses. Data are presented as mean±SEM of three independent experiments. ***p<0.001; n.s., not significant.

FIGS. 10(A-G) illustrate PIK3CA E545K mutation promotes the nuclear translocation of p85β. (A & B) Depletion or overexpression of p85β have no impact on p110 stability and AKT signaling. The parental and p85β KO cells were grown in 6-well plates. After serum starvation (16 hours), cells were treated with insulin (1 μg/ml for 15 minutes) or EGF (200 ng/ml for 15 minutes). Cell lysates were blotted with the indicated antibodies (A). Overexpression of p85α, but not p85β, stabilizes p110α protein and increases phosphorylation of AKT. DLD1 PIK3CA E545K-only cells were transfected with HA-tagged p85β or p85α. Three days after transfection, lysates from indicated cell lines were harvested and blotted with indicated antibodies (B). Knockout of BRD7 abolishes nuclear translocation of p85α but not p85β. BRD7 gene was knocked out in DLD cells using the CRISPR/Cas9 system. DLD1 cells and BRD7 KO cells were fractionated and blotted with indicated antibodies. Quantification of Western blots shown in FIG. 10C by Image J. SW480 was transfected with FLAG-tagged wild-type PIK3CA, PIK3CA H1047R, or E545K mutant construct. Three days post-transfection, cell lysates were fractionated and blotted with indicated antibodies. (F & G) Immunohistochemistry images of p85β staining in colorectal tumors with PIK3CA E545K mutation (F) or wild-type PIK3CA (G).

FIGS. 11(A-F) illustrate nuclear localization signal is critical for nuclear translocation of p85β. (A) The p85β. NLS mutant does not impact its interaction with p110α and p110β. The DLD1 PIK3CA E545K-only p85β. KO cells were transfected with either HA-tagged p85β or HA-tagged p85β$^{KR-AA}$. Stable expression clones were selected. Cell lysates were immunoprecipitated with anti-HA agarose and blotted with the indicated antibodies. (B & C) NLS of p85β is critical for its nuclear translocation. The indicated cells were fractionated and blotted with indicated antibodies (B). The p85β subcellular localization of the indicated cell lines was evaluated by immunofluorescence assay (C). (D & E) Reconstitution of wild-type p85β, but not the p85β$^{KR-AA}$ mutant, rescues growth defects caused by p85β depletion in DLD1 PIK3CA E545K cells. The growth curve (D) and colony formation (E) of indicated cell lines are shown. (F) KR-AA mutation has no impact on p85β-p110α interaction. The indicated FLAG-tagged p110α and HA-tagged p85β constructions were co-transfected into 293T cells. Cell lysates were immunoprecipitated with anti-HA agarose and then blotted with indicated antibodies.

Figure 5A:
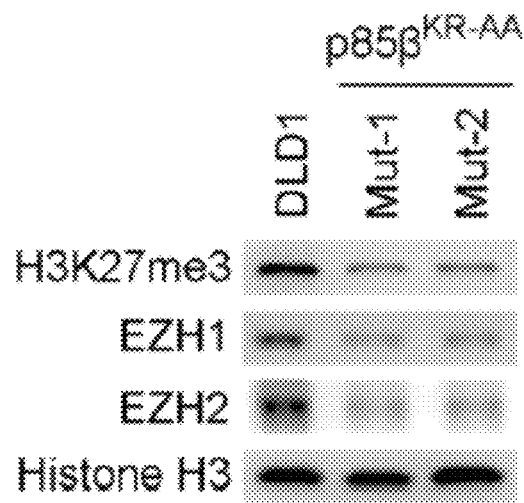
Figure 5B:
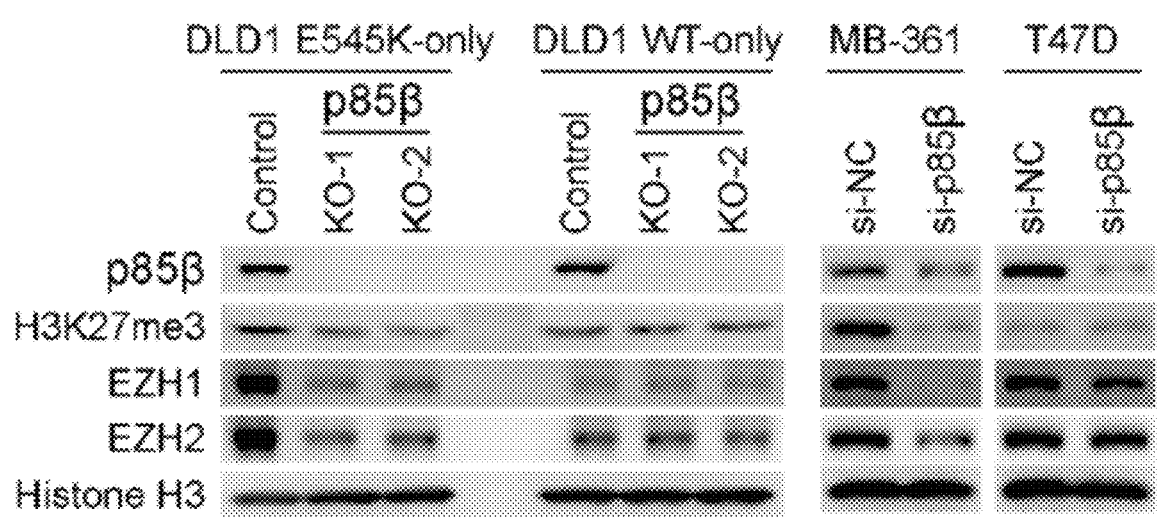
Figure 5C:
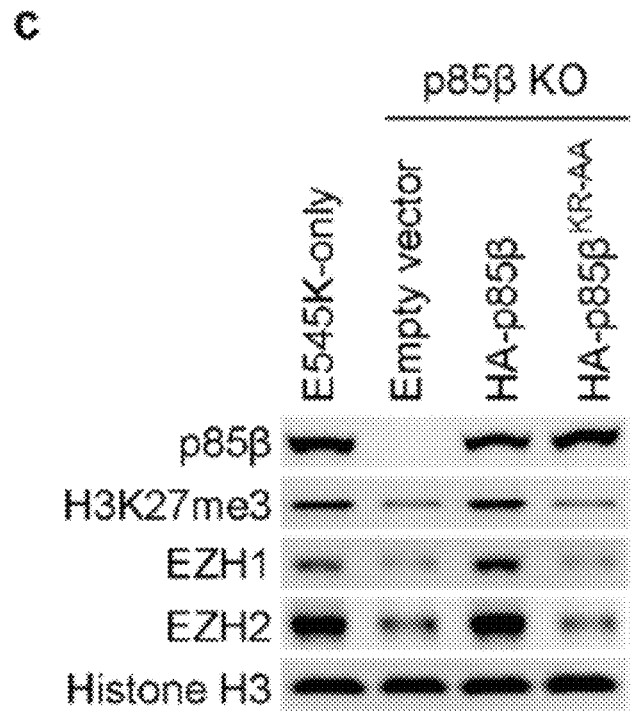
Figure 5D:
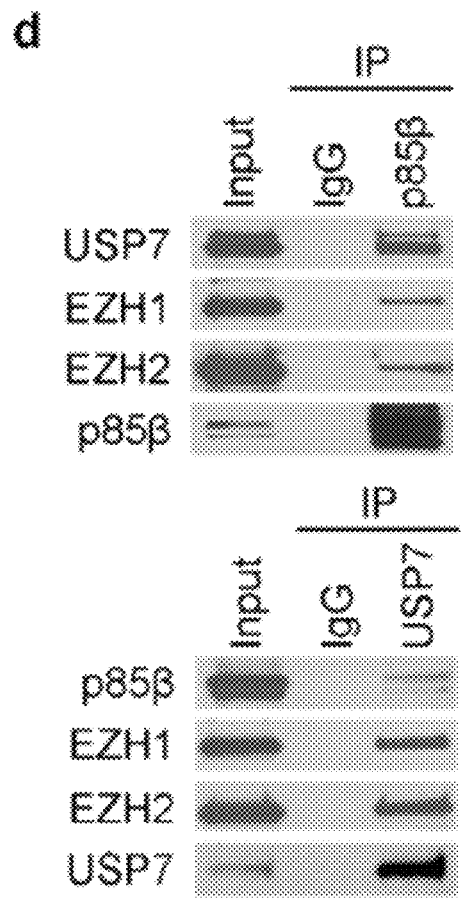

FIGS. 12(A-F) illustrate nuclear p85β increases tri-methylation of H3K27 by stabilizing EZH1/2 proteins. Heat map analysis of microarray data showing differentially expressed genes between DLD1 and p85β$^{KR-AA}$ mutant cells. Nuclear p85β have no impact on trimethylation of other sites of histone H3 (except H3K27me3 as shown in FIG. 5A to C) and protein levels of other subunits of PRC2 (except EZH1 and EZH2 as shown in FIG. 5A to C). Cell lysates of p85β KO and their control cells were blotted with indicated antibodies. EZH 1 and EZH2 proteins are less stable in p85β knockout E545K-only cells. DLD1 E545K-only and its p85β knockout derivative cells were treated with cycloheximide (CHX) for the indicated times. Cell lysates were blotted with the indicated antibodies. Western blots are shown in the left panel, and quantification of EZH1 and EZH2 protein levels are shown in the right panel. Knockout of p85β has no effect on mRNA levels of EZH1 and EZH2. Expression of EZH1 and EZH2 in DLD1 PIK3CA E545K-only and DLD1 PIK3CA E545K-only p85β KO cells were analyzed by quantitative RT-PCR. EZH1 and EZH2 bind to p85β, but not p110α and p110β. EZH1 and EZH2 were immunoprecipitated from DLD1 cell lysates, respectively, and blotted with the indicated antibodies.

FIGS. 13(A-G) illustrate body weights of mice treated were maintained during the course of treatment.

Figure 14A:
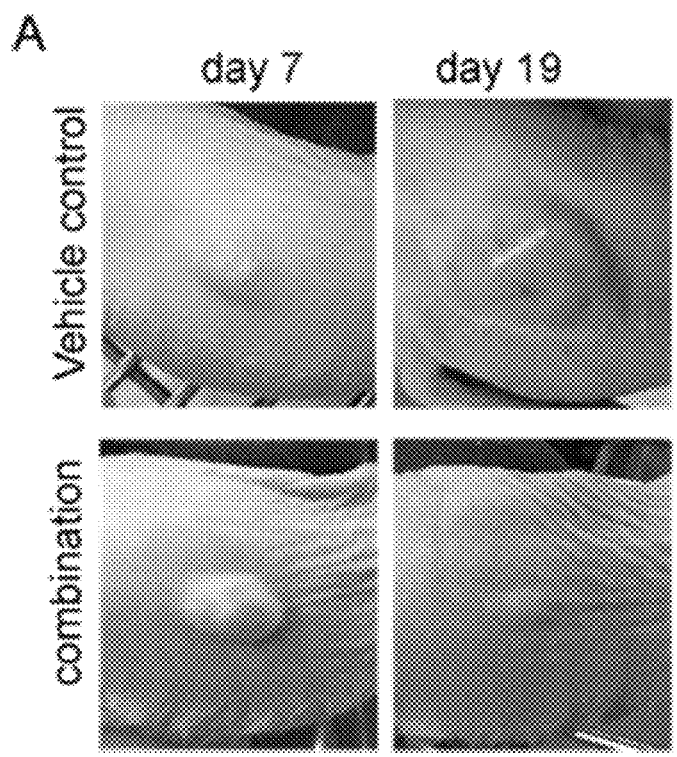
Figure 14B:
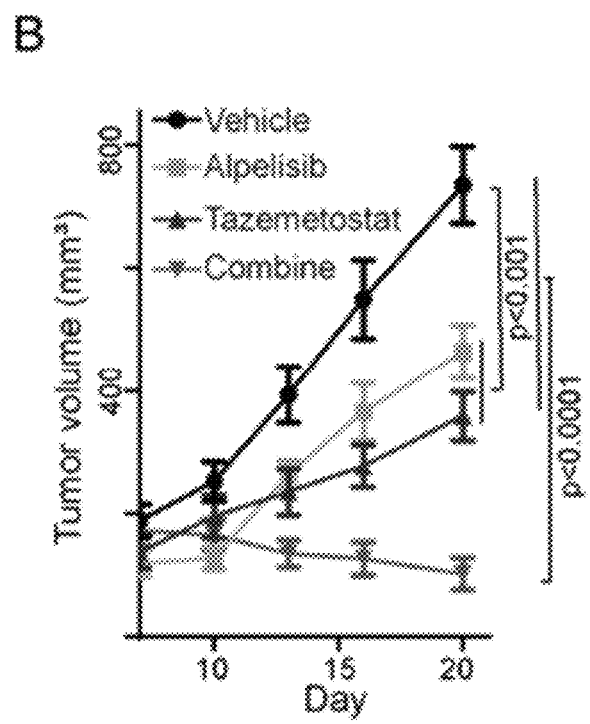

FIGS. 14(A-B) illustrate three million of DLD1 cells were injected subcutaneously into athymic nude mice. Once tumors reached average size of 200 mm³, mice were randomly assigned into four groups and treated with vehicle, Tazemetostat at 500 mg/kg oral twice daily [a dose used by Epizyme], Alpelisib at 12.5 mg/kg once daily, or the drug combination. Representative tumor images are shown in (A) and tumor growth are shown in (B). Statistical analyses, two-way ANOVA.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this invention belongs.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. Exemplary cancers include, but are not limited to, lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors);

penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; vulvar cancer (e.g., Paget's disease of the vulva); diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CIVIL) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); and brain cancer (e.g., meningioma, glioblastomas, glioma (e.g., astrocytoma, oligodendroglioma), medulloblastoma).

As used herein, the term "responsiveness" is interchangeable with terms "responsive", "sensitive", and "sensitivity", and it is meant that a subject is showing therapeutic responses when administered a composition of the disclosure, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the disclosure, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively, samples can be obtained by the physician according to routine practice in the art.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the disclosure, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the disclosure, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/ nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

A "subject" includes any human or nonhuman animal. The term "nonhuman animal" includes, but is not limited to, vertebrates, such as nonhuman primates, sheep, dogs, cats, rabbits, ferrets, rodents such as mice, rats and guinea pigs, avian species, such as chickens, amphibians, and reptiles. In preferred embodiments, the subject is a mammal, such as a nonhuman primate, sheep, dog, cat, rabbit, ferret or rodent. In more preferred embodiments, the subject is a human. The terms, "subject," "patient" and "individual" are used interchangeably herein.

A "therapeutically effective amount" or "therapeutically effective dosage" of a drug or therapeutic agent, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in vitro assays.

By way of example, an anti-cancer agent promotes cancer regression in a subject. In some embodiments, a therapeutically effective amount of the drug promotes cancer regression to the point of eliminating the cancer. "Promoting cancer regression" means that administering an effective amount of an anti-cancer agent or agents results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent inhibits cell growth or tumor growth by at least about 10%, for example, at least about 20%, at least about 40%, at least about 60%, or at least about 80% relative to untreated subjects. In other embodiments, tumor regression may be observed and continue for a period of at least about 20 days, at least about 40 days, or at least about 60 days.

A therapeutically effective amount of an agent or drug includes a "prophylactically effective amount," which is any amount of the drug that, when administered alone or in combination with another agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

"Treatment" refers to clinical intervention designed to alter the natural course of the individual or cell being treated, and can be performed either for prophylaxis or during the course of clinical pathology. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease. Desirable effects of treatment include preventing occurrence or recurrence of disease, preventing metastasis, decreasing the rate of disease progression, ameliorating or palliating the disease state, and remission or improved prognosis.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

Embodiments described herein relate to compositions and methods of treating PIK3CA helical domain mutant cancer in a subject in need thereof. PI3Ks consist of p110 catalytic subunits and p85 regulatory subunits. PIK3CA, encoding p110α, is frequently mutated in human cancers. Most PIK3CA mutations are clustered in two hotspots: the helical domain and the kinase domains. It was found that in cancer cells with a p110α helical domain mutation, p85β, but not p85α, disassociates from p110α helical domain mutant protein and translocates into the nucleus through a nuclear localization sequence (NLS), thereby promoting tumor growth. The nuclear p85β recruits deubiquitinase USP7 to stabilize histone methyltransferases EZH1 and EZH2 and enhances histone H3 lysine 27 trimethylation (H3K27Me3). We had previously found that p110α helical domain mutant proteins directly bind to IRS1 and activate the canonical PDK1-AKT signaling pathways. Therefore, PIK3CA helical domain mutations promote oncogenesis through two independent pathways: a canonical p110-PDK1-AKT pathway and a nuclear p85β-USP7-EZH1/2 axis.

It was found that simultaneously targeting p85β-stabilized EZHs and p110α reduces the growth of tumors harboring PIK3CA helical domain mutations, but not tumors with PIK3CA WT or kinase domain mutations. Inhibiting or blocking nuclear translocation of p85β and/or administering an EZH inhibitor sensitizes PIK3CA helical domain mutant cancers to p110α inhibitors, suggesting that targeting p85β nuclear translocation in combination with a p110α inhibitor can be an effective therapeutic approach for PIK3CA helical domain mutant cancers or tumors. Accordingly, in some embodiments described herein, a method of treating PIK3CA helical domain mutant cancer in a subject in need thereof includes administering to the subject therapeutically effective amounts of (i) an inhibitor of nuclear translocation of p85β and/or an EZH inhibitor in combination with (ii) a PI3K inhibitor.

Accordingly, in some embodiments described herein a method of treating PIK3CA helical domain mutant cancer in a subject in need thereof includes administering to the subject therapeutically effective amounts of (i) an inhibitor of nuclear translocation of p85β and/or an EZH inhibitor in combination with (ii) a PI3K inhibitor.

The combination therapy can also be administered to PIK3CA helical domain mutant cancer cells to inhibit proliferation or induce cell death. In one aspect, an inhibitor of nuclear translocation of p85β and/or an EZH inhibitor is administered subsequent to administration of the PI3K inhibitor. In another aspect, a PI3K inhibitor is administered prior to administration of an inhibitor of nuclear translocation of p85β and/or an EZH inhibitor. In one aspect, an inhibitor of nuclear translocation of p85β and/or an EZH inhibitor is administered subsequent to administration of a PI3K inhibitor such that the inhibitors are administered either in a single composition or in two or more compositions, e.g., administered simultaneously, sequentially, or in alternation. In one aspect, an inhibitor of nuclear translocation of p85β and/or an EZH inhibitor is administered prior to administration of a PI3K inhibitor, such that other therapeutic agents can be administered either in a single composition or in two or more compositions, e.g., administered simultaneously, sequentially, or in alternation.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects, the combination therapies described herein can result in a synergistic effect in the treatment of a PIK3A helical mutant domain cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects, "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, the combination of an inhibitor of nuclear translocation of p85β and/or an EZH inhibitor and a PI3K inhibitor may be administered in combination with radiation therapy. Radiation therapy can also be administered in combination with a composition of the disclosure and another chemotherapeutic agent described herein as part of a multiple agent therapy.

Combination therapy can be achieved by administering (i) an inhibitor of nuclear translocation of p85β and/or an EZH inhibitor and (ii) a PI3K inhibitor, each of which is formulated and administered separately, or by administering the two or more agents in a single formulation. Other combinations are also encompassed by combination therapy. For example, the two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases, even longer intervals are possible. While in many cases it is desirable that the two or more agents used in a combination therapy be present in within the patient's body at the same time, this need not be so.

The disclosure also provides pharmaceutical compositions comprising (i) an inhibitor of nuclear translocation of p85β and/or an EZH inhibitor and (ii) a PI3K inhibitor mixed with pharmaceutically suitable carriers or excipient(s) at doses to treat or prevent a PIK3CA helical domain mutant cancer in a subject in need thereof as described herein.

In some embodiments, the inhibitor of nuclear translocation of p85β is an inhibitor of transport receptor importin-beta, such as importazole.

In other embodiments, the EZH inhibitor includes at least one of EPZ011989 (CAS No. 1598383-40-4), EPZ005687 (CAS No. 1396772-26-1), GSK126 (CAS No. 1346574-57-9), GSK343 (CAS No. 1346704-33-3), GSK503 (CAS No. 1346572-63-1), tazemetostat (EPZ-6438, CAS No. 1403254-99-8), 3-deazaneplanocin A (DZNeP, CAS No. 120964-45-6), El1 (CAS No. 1418308-27-6), CPI-360 (CAS No. 1802175-06-9), CPI-169 (CAS No. 1450655-76-1), JQ-EZ-05 (JQEZ5, CAS No. 1913252-04-6), PF-06726304 (CAS No. 1616287-82-1), UNC1999 (CAS No. 1431612-23-5), UNC2400 (CAS No. 1433200-49-7) or analogs thereof.

Other EZH inhibitors can include compounds of Formula (I)-(VIa) described in U.S. Patent Application Publication Nos. 2019/0151325 and 2012/024734, both of which are incorporated by reference in their entirety. Additional EZH inhibitors will be apparent to those skilled in the art. In some embodiments of the strategies, treatment modalities, methods, combinations, and compositions provided herein, the EZH inhibitor is an EZH2 inhibitor described in U.S. Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120104, and in U.S. Ser. No. 14/839,273, published as US 2015/0368229, the entire contents of each of which are incorporated herein by reference.

A large variety of PI3 kinase inhibitors are known in the art. Examples of the PI3K inhibitors include Pictilisib, dactolisib, wortmannin, LY294002, Idelalisib, duvelisib, buparlisib, IPI-549, SP2523, GDC-0326, TGR-1202, VPS34 inhibitor 1, GSK2269557, GDC-0084, SAR405, AZD8835, LY3023414, PI-103, TGX-221, NU7441, IC-87114, wortmannin, XL147 analogue, ZSTK474, Alpelisib, PIK-75 HCl, A66, AS-605240, 3-Methyladenine (3-MA), PIK-93, PIK-90, AZD64822, PF-04691502, Apitolisib, GSK1059615, Duvelisib, Gedatolisib, TG100-115, AS-252424, BGT226, CUDC-907, AS-604850, PIK-294, GSK2636771, Copanlisib, YM201636, CH5132799, CAY10505, PIK-293, PKI-402, TG100713, VS-5584, Taselisib, CZC24832, AMG319, GSK2292767, HS-173, Perifosine, Quercetin, Voxtalisib, PIK-93, Omipalisib, PIK-90, GNE-317, Pilaralisib, Umbralisib, PX-866, PF-4989216, AZD8186, 740 Y-P, Vps34-IN1, PIK-III, PI-3065 or analogs thereof.

In still other embodiments, the PI3K inhibitor includes a p110α inhibitor, such as a selective p110α inhibitor. The selective p110α inhibitor can include Alpelisib.

In some embodiments, mixtures of compounds described herein can also be administered to the patient as a simple mixture or in suitable formulated pharmaceutical compositions. For example, one aspect of the disclosure relates to a pharmaceutical composition comprising a therapeutically effective dose of an (i) an inhibitor of nuclear translocation of p85β and/or an EZH inhibitor in combination with (ii) a PI3K inhibitor one or more other therapeutic agents, and a pharmaceutically acceptable diluent or carrier.

A "pharmaceutical composition" is a formulation containing the compounds of the disclosure in a form suitable for administration to a subject. Compounds described herein can each be formulated individually or in multiple pharmaceutical compositions in any combinations of the active ingredients. Accordingly, one or more administration routes can be properly elected based on the dosage form of each pharmaceutical composition. Alternatively, compounds described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the disclosure can be administered to a subject in many of the well-known methods currently used for chemotherapeutic treatment. For example, for treatment of cancers, compounds described herein may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

In certain embodiments, the therapeutically effective amount of each therapeutic agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of (i) the inhibitor of nuclear translocation of p85β and/or the EZH inhibitor and (ii) the PI3K inhibitor described herein, other therapeutic agents described herein, compositions comprising (i) the inhibitor of nuclear translocation of p85β and/or the EZH inhibitor and (ii) the PI3K inhibitor described herein and one or more other therapeutic agents, or the pharmaceutical compositions described herein vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The dosage regimen utilizing the compounds described herein is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in Remington: the Science and Practice of Pharmacy, 19th edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In some embodiments, the subject to be treated includes any human subject who has been diagnosed with, has symptoms of, or is at risk of developing a cancer or a precancerous condition. The subject of the disclosure includes any human subject expressing a PIK3CA helical domain mutant cancer. For example, a mutant PIK3CA helical domain comprises one or more mutations, wherein the mutation is a substitution, a point mutation, a nonsense mutation, a missense mutation, a deletion, or an insertion or any other PIK3CA helical domain mutation described herein.

In some embodiments, the PIK3CA helical domain mutant cancer includes a mutation in the p110α helical domain. The mutation can include at least of a mutation of residues E542, E545, or Q546 of the p110α helical domain.

A subject in need thereof may have refractory or resistant PIK3CA helical domain mutant cancer. "Refractory or resistant cancer" means cancer that does not respond to treatment. The PIK3CA helical domain mutant cancer may be resistant at the beginning of treatment or it may become resistant during treatment. In some embodiments, the subject in need thereof has PIK3CA helical domain mutant cancer recurrence following remission on most recent therapy. In some embodiments, the subject in need thereof received and failed all known effective therapies for PIK3CA helical domain mutant cancer treatment. In some embodiments, the subject in need thereof received at least one prior therapy. In certain embodiments the prior therapy is a monotherapy. In certain embodiments the prior therapy is a combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH inhibitors, PIK3CA inhibitors, or any other therapeutic agent.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

In other embodiments, the PIK3CA helical domain mutant cancer includes at least one of breast cancer, colon cancer, colorectal cancer, endometrial cancer, brain cancer, skin cancer, ovarian cancer, gastric cancer, lung cancer, thyroid cancer, head and neck cancer, cervical cancer, pancreatic cancer, esophageal cancer, liver/biliary cancer tract cancer, pituitary tumors, urological tumors, leukemia/lymphoma, or neuroblastoma.

In some embodiments, the PIK3CA helical domain mutant cancer is a cancer affecting lung cells. PIK3CA helical domain mutant cancer of the lung can include lung cancer, a precancer or precancerous condition of the lung, benign growths or lesions of the lung, and malignant growths or lesions of the lung, and metastatic lesions in tissue and organs in the body other than the lung. Preferably, the combination of compounds described herein may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung to neoplasms having histologic and ultrastructual heterogeneity (e.g., mixed cell types).

In some embodiments, the PIK3CA helical domain mutant cancer is a cancer of the colon, such as colon cancer. The combination of compounds described herein can be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In some embodiments, the PIK3CA helical domain mutant cancer is a cancer of the pancreas. PIK3CA helical domain mutant cancers of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

In some embodiments, the PIK3CA helical domain mutant cancer is a cancer of the prostate. Cancers of the prostate can include all forms of cell proliferative disorders affecting prostate cells. Cell proliferative disorders of the prostate can include prostate cancer, a precancer or precancerous condition of the prostate, benign growths or lesions of the prostate, malignant growths or lesions of the prostate and metastatic lesions in tissue and organs in the body other than the prostate. Cell proliferative disorders of the prostate can include hyperplasia, metaplasia, and dysplasia of the prostate.

In some embodiments, the PIK3CA helical domain mutant cancer is a cancer of the skin. PIK3CA helical domain mutant cancers of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

In some embodiments, the PIK3CA helical domain mutant cancer is a cancer of the ovary. PIK3CA helical domain mutant cancers of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

In some embodiments, the PIK3CA helical domain mutant cancer is a cancer of the breast. PIK3CA helical domain mutant cancers of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

The combination of compounds described herein may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructural heterogeneity (e.g., mixed cell types).

In some embodiments, the breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

In some embodiments, the PIK3CA helical domain mutant cancer to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. The PIK3CA helical domain mutant cancer that is to be treated can be staged according to an American Joint Committee on Cancer (AJCC) classification as Stage I, Stage IIA, Stage IIB, Stage IIIA, Stage IIIB, Stage IIIC, or Stage IV. The PIK3CA helical domain mutant cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

The PIK3CA helical domain mutant cancer that is to be treated can include a tumor that has been determined to be less than or equal to about 2 centimeters in diameter. The PIK3CA helical domain mutant cancer that is to be treated can include a tumor that has been determined to be from about 2 to about 5 centimeters in diameter. The PIK3CA helical domain mutant cancer that is to be treated can include a tumor that has been determined to be greater than or equal to about 3 centimeters in diameter. The PIK3CA helical domain mutant cancer that is to be treated can include a tumor that has been determined to be greater than 5 centimeters in diameter. The PIK3CA helical domain mutant cancer that is to be treated can be classified by microscopic appearance as well differentiated, moderately differentiated, poorly differentiated, or undifferentiated. The PIK3CA helical domain mutant cancer that is to be treated can be classified by microscopic appearance with respect to mitosis count (e.g., amount of cell division) or nuclear pleiomorphism (e.g., change in cells). The PIK3CA helical domain mutant cancer that is to be treated can be classified by microscopic appearance as being associated with areas of necrosis (e.g., areas of dying or degenerating cells). The PIK3CA helical domain mutant cancer that is to be treated can be classified as having an abnormal karyotype, having an abnormal number of chromosomes, or having one or more chromosomes that are abnormal in appearance. The PIK3CA helical domain mutant cancer that is to be treated can be classified as being aneuploid, triploid, tetraploid, or as having an altered ploidy. The PIK3CA helical domain mutant cancer that is to be treated can be classified as having a chromosomal translocation, or a deletion or duplication of an entire chromosome, or a region of deletion, duplication or amplification of a portion of a chromosome.

The PIK3CA helical domain mutant cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). The PIK3CA helical domain mutant cancer that is to be treated can be typed as having a low S-phase fraction or a high S-phase fraction.

Treating the PIK3CA helical domain mutant cancer with the combination of compounds can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating the PIK3CA helical domain mutant cancer with the combination of compounds can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating the PIK3CA helical domain mutant cancer with the combination of compounds can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating the PIK3CA helical domain mutant cancer with the combination of compounds can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating the PIK3CA helical domain mutant cancer with the combination of compounds can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with the combination of compounds. An increase in average survival time of a population may also be measured, for example, by calculating for a population the average length of survival following completion of a first round of treatment with the combination of compounds.

Treating the PIK3CA helical domain mutant cancer with the combination of compounds can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with the combination of compounds. An increase in average survival time of a population may also be measured, for example, by calculating for a population the average length of survival following completion of a first round of treatment with combination of compounds.

Treating the PIK3CA helical domain mutant cancer can result in increase in average survival time of a population of treated subjects in comparison to a population receiving monotherapy with a drug that is or is not a compound described herein. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with the combination of compounds. An increase in average survival time of a population may also be measured, for example, by calculating for a population the average length of survival following completion of a first round of treatment with the combination of compounds.

Treating the PIK3CA helical domain mutant cancer with the combination of compounds can result in a decrease in the mortality rate of a population of treated subjects in comparison to a population receiving carrier alone. Treating the PIK3CA helical domain mutant cancer can result in a decrease in the mortality rate of a population of treated subjects in comparison to an untreated population. Treating the PIK3CA helical domain mutant cancer can result in a decrease in the mortality rate of a population of treated subjects in comparison to a population receiving monotherapy with a drug that is or is not a compound described herein. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with the combination of compounds.

Treating the PIK3CA helical domain mutant cancer with the combination of compounds can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating the PIK3CA helical domain mutant cancer with the combination of compounds can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement.

Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing the PIK3CA helical domain mutant cancer with the combination of compounds can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing the PIK3CA helical domain mutant cancer with the combination of compounds can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing the PIK3CA helical domain mutant cancer with the combination of compounds can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing the PIK3CA helical domain mutant cancer with the combination of compounds can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating the PIK3CA helical domain mutant cancer with the combination of compounds can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., Proc Natl Acad Sci USA. 100(5): 2674-8, 2003. In an aspect, cell death occurs by apoptosis.

Preferably, an effective amount of the combination of compounds described herein, is not significantly cytotoxic to normal cells. A therapeutically effective amount of the combination of compounds is not significantly cytotoxic to normal cells if administration of the combination of compounds in a therapeutically effective amount does not induce cell death in greater than 10% of normal cells. A therapeutically effective amount of the combination of compounds does not significantly affect the viability of normal cells if administration of the combination of compounds in a therapeutically effective amount does not induce cell death in greater than 10% of normal cells. In an aspect, cell death occurs by apoptosis.

In still other embodiments, the presence of a mutant PIK3CA helical domain in the cancer cells can be detected or determined prior to administration of (i) the inhibitor of nuclear translocation of p85β and/or the EZH inhibitor in combination with (ii) the PI3K inhibitor. The methods described herein can include assaying mutant PIK3CA helical domain in cancer cells of a subject to determine whether the subject is, or is not, suitable for administration of (i) the inhibitor of nuclear translocation of p85β and/or the EZH inhibitor in combination with (ii) the PI3K inhibitor. Further, in any the methods comprising the measurement of mutant PIK3CA helical domain in a test tissue sample, it should be understood that the step comprising the provision of a test tissue sample obtained from a patient is an optional step. That is, in certain embodiments the method includes this step, and in other embodiments, this step is not included in the method. It should also be understood that in certain preferred embodiments the "assessing" step to identify, or determine the number or proportion of, cells in the test tissue sample that include mutant PIK3CA helical domain is performed by a transformative method of assaying for mutant PIK3CA helical domain, for example by performing a reverse transcriptase-polymerase chain reaction (RT-PCR) assay. In certain other embodiments, no transformative step is involved and mutant PIK3CA helical domain is assessed by, for example, reviewing a report of test results from a laboratory. In certain embodiments, the steps of the methods up to, and including, assessing mutant PIK3CA helical domain provides an intermediate result that may be provided to a physician or other medical practitioner for use in selecting a suitable candidate inhibitor of nuclear translocation of p85β and/or EZH inhibitor in combination with (ii) PI3K inhibitor for administration to the patient. In certain embodiments, the steps that provide the intermediate result may be performed by a medical practitioner or someone acting under the direction of a medical practitioner. In other embodiment, these steps are performed by an independent person or laboratory.

In certain embodiments of any of the methods described herein, the proportion of cells including mutant PIK3CA helical domain is assessed by performing an assay to determine the presence of PIK3CA helical domain. In further embodiments, the presence of mutant PIK3CA helical domain RNA is determined by RT-PCR, in situ hybridization or RNase protection.

This disclosure further provides a method for predicting the therapeutic effectiveness of (i) an inhibitor of nuclear translocation of p85β and/or an EZH inhibitor in combination with (ii) a PI3K inhibitor for treating a cancer patient, which method comprises: (a) optionally providing a test tissue sample obtained from a patient with cancer of the tissue, the test tissue sample comprising tumor cells; (b) assaying the test tissue sample to determine the proportion of cells therein with a mutant PIK3CA helical domain; (c) comparing the proportion of cells with a mutant PIK3CA helical domain with a predetermined threshold value; and (d) predicting the therapeutic effectiveness of (i) an inhibitor of nuclear translocation of p85β and/or an EZH inhibitor in combination with (ii) a PI3K inhibitor in treating the tumor, wherein if the proportion of cells with a mutant PIK3CA helical domain exceeds the threshold proportion the combination of (i) an inhibitor of nuclear translocation of p85β and/or an EZH inhibitor and (ii) a PI3K inhibitor is predicted to be effective in treating the patient, and wherein if the proportion of cells that express a mutant PIK3CA helical domain is below the threshold proportion the combination of (i) an inhibitor of nuclear translocation of p85β and/or an EZH inhibitor and (ii) a PI3K inhibitor is predicted to not be effective in treating the patient.

The present invention is further illustrated by the following examples which should not be construed as further limiting. The contents of all figures and all references, patents and published patent applications cited throughout this application are expressly incorporated herein by reference.

Example 1

In this Example we show that p85 β, but not p85α, disassociates from p110α and translocates into the nucleus in cancer cells with a p110α helical domain mutation, thereby promoting tumor growth. The nuclear p85β recruits deubiquitinase USP7 to stabilize histone methyltransferases EZH1 and EZH2 and enhances histone H3 lysine 27 trimethylation (H3K27Me3). Moreover, we demonstrate that a combination of Alpelisib and an EZH inhibitor, Tazemetostat, induces regression of xenograft tumors harboring a PIK3CA helical domain mutation, but not tumors with either a WT PIK3CA or a PIK3CA kinase domain mutation.

Materials & Methods
Tissue Culture and Transfection

Colorectal cancer (CRC) cell lines DLD1, HCT116, RKO, SW480, LoVo, and genetically engineered isogenic cell lines DLD1 PIK3CA E545K cells and DLD1 PIK3CA WT cells were grown in McCoy's 5A medium (Gibco) supplemented with 10% of fetal bovine serum (Gibco). Lung cancer cell line H460 and breast cancer cell line T47D were cultured in RPMI 1640 medium (Sigma) containing 10% of FBS. Breast cancer cell line MDA-MB361 was maintained in Leibovitz's L-15 medium (Gibco) with 20% of FBS. Human embryonic kidney HEK 293T cells were cultured in DMEM medium (Sigma) containing 10% FBS. Penicillin/Streptomycin (1%) was added to tissue culture media for all cultures. Cells were incubated at 37° C. in a humidified atmosphere with 5% $CO_2$. All cell lines were tested routinely to avoid *Mycoplasma* contamination (Yeasen, cat #40601ES20). The cell lines were authenticated by the Genetica DNA Laboratories using STR profiling. Transfection was conducted using Lipofectamine 3000 reagent (Life Technologies) according to the manufacturer's instructions.

DNA Constructs and Mutagenesis

The plasmids we constructed in this example are listed in Table 1. Briefly, pCMV backbones (Invitrogen) were used for gene expression in mammalian cells using the USER cloning system. LentiCRISPR V2 backbone (Addgene) was used for gene knockout in cells. Point mutations in constructs were generated using a Site-Directed Mutagenesis Kit (Agilent). pAAV-loxP-Neo vector was used for homologous recombination of endogenous p85β NLS point mutation.

CRISPR/CAS9 Genome Editing

Three different guiding RNA pairs for p85β knockout were designed using the IDT design tool and cloned individually into the lentiCRISPRv2 vector as described previously. DLD1 isogenic cell lines with PIK3CA E545K or with wild-type PIK3CA were transfected with these vectors. After 48 hours, cells were trypsinized, and stable clones were selected using 1.5 µg/ml puromycin (Invitrogen) for 2 weeks. Knock-out of p85β was screened using genomic PCR and validated by Western blot.

For CRISPR/CAS9 mediated NLS point mutation on endogenous PIK3R2 locus, 3 different guide RNA pairs surrounding NLS mutation sites of PIK3R2 locus were designed and cloned. Homologous arms of the NLS target sites were mutated and cloned into the pAAV-loxP-Neo vector. Targeting vectors were co-transfected with individual gRNA vectors into DLD1 cells. p85β NLS mutated cell clones were screened by genomic PCR and verified by genomic DNA sequencing.

siRNA Knockdown

The siRNAs targeting human PIK3R2/p85β and the scramble siRNA control were purchased from Biotend (Shanghai, China). Cells were harvested 48-72 hours post-transfection for various assays.

RNA Extraction and Quantitative Real-Time PCR

Total RNA was extracted and purified using TRIzol (Invitrogen) according to the manufacturer's instructions, and 1 µg of total RNA was reverse transcribed using the PrimeScript RT Reagent Kit (TaKaRa, Japan). The gene expression levels were measured by a quantitative real-time PCR system (Qiagen, Germany). β-tubulin was used as the reference gene for normalization.

Cell Growth Assays

For cell proliferation, 3000 cells per well were seeded in a 96-well plate. Cell viability was measured for 5 consecutive days using Cell Counting Kit-8 (Dojindo, Japan) according to the manufacturer's instructions. Absorbance at OD450 was used to plot cell growth curves. For clone formation assay, the same number of cells were seeded in 6-well plates and maintained in McCoy's 5A medium with 1% FBS. After 14 days, cells were washed with PBS and stained with 0.5% crystal violet.

Immunofluorescence Staining

Immunofluorescence staining was performed as described previously. Briefly, cells were seeded on coverslips in a 6-well plate. After 24 to 48 hours, cells were fixed in 4% paraformaldehyde for 20 min, permeabilized with 0.5% Triton X-100 for 30 min, and blocked in 10% goat serum for 1 hour at room temperature. The cells were then incubated with p85β antibodies in 10% goat serum at 4° C. overnight, followed by incubation with secondary fluorochrome-labeled antibodies for 40 min at 37° C. After incubation with DAPI for 3-5 min at room temperature to stain the nucleus, cells were washed three times with PBS and imaged with a confocal laser scanning microscope.

Co-Immunoprecipitation and Western Blotting

Co-immunoprecipitation (Co-IP) was performed. For transfection-based Co-IP assays, cells were transfected with indicated vectors and lysed in 1 mL of lysis buffer (50 mM Tris-HCl at pH 7.5, 1 mM EDTA at pH 8.0, 150 mM NaCl, 1% NP-40, cOmplete Protease Inhibitor, PhosSTOP, and PMSF). Cell lysates were immunoprecipitated with indicated primary antibodies overnight at 4° C. and then Protein A/G for 2 hrs. The beads were washed three times with the lysis buffer and eluted in SDS sample buffer. The eluted immunocomplexes were resolved by SDS-PAGE, followed by Western blotting.

Nuclear/Cytoplasmic Fractionation

Cell pellets were resuspended in 1 ml fractionation buffer (0.1% NP-40, cOmplete Protease Inhibitor, PhosSTOP, and PMSF in PBS buffer) and gently pipetted up and down 15 times and then centrifuged at 12000 rpm for 30 seconds immediately. The supernatants were labeled as cytoplasmic fractions. The pellets were washed twice with fractionation buffer and then dissolved in 160 µl of fractionation buffer as the nuclear fraction. Each fraction was sonicated 10 seconds at 60% output settings.

Xenografts

All animal experiments were performed in accordance with protocols approved by either the IACUC committee at Case Western Reserve University. Xenografts were established as described previously. Briefly, for cells, three million cells were injected subcutaneously and bilaterally into athymic nude mice. For PDXs, two pieces of xenograft tumors (~2 to 4 mm$^3$) were inserted subcutaneously and bilaterally into athymic nude mice. Tumor volume was measured at the indicated time points and calculated as length×width$^2$/2.

Drug Treatment

Alpelisib (BYL719) and Tazematostat (EPZ-6438) were dissolved in 0.5% carboxymethylcellulose sodium salt (CMC). GSK2816126 was dissolved in 20% Captisol. Once tumor sizes reached 100-150 mm$^3$, mice were randomly assigned into different groups (5 mice per group) and treated with vehicle, Alpelisib (BYL719, 12.5 mg/kg, oral gavage, once daily), EPZ-6438 [500 mg/kg, oral gavage], GSK2816126 (25 mg/kg, once daily, I.P.), a combination of BYL719 and EPZ-6438, or a combination of BYL719 and GSK2816126.

Microarray Analysis

DLD1 cells and two independently-derived clones of DLD1 p85$^{KR-AA}$ mutant cells were grown to 80% confluence in 6-well plates, and RNAs were extracted for microarray analysis. Input RNA was provided at 50 ng/µl, and the labeling reaction was initiated with 150 ng of RNA. Protocol for the chemistry used to prepare the samples for interrogation on the expression microarrays followed the manufacturer's instructions. Samples were labeled robotically using the Affymetrix WT [Whole transcript] labeling protocol and the Beckman Coulter Biomek FX$^P$ Laboratory Automation Workstation; scripts were provided by Affymetrix to process up to 96 samples in batch. Samples were interrogated on the Human Gene Array 2.1 in the PEG format. Hybridization, washing, staining, and data collection were carried out in the Affymetrix Gene Titan MC [Multi channel] instrument. Differential expression of genes (DLD1 vs. both p85$^{KR-AA}$ Mut clones, fold change ≥2 or ≤−2 and p-value≤0.05) was analyzed by the Gene Expression and Genotyping Facility of Case Western Reserve University.

Immunohistochemistry

Immunohistochemistry was performed. Briefly, paraffin-embedded mouse and human tissues were deparaffinized in xylene and antigen retrieved by boiling the sample for 20 min. Samples were incubated with primary antibodies at 4° C. overnight. The sections were stained with secondary antibody for 30 min at room temperature and then stained with an EnVision-HRP kit (Dako).

Mining the TCGA Datasets

The dataset files of colorectal cancer (COAD), bladder carcinoma (BLCA), endometrial carcinoma (UCEC), and breast cancer (BRCA) were downloaded from the TCGA website. The files include the RNA-seq files providing normalized FPKM values, the somatic mutations, and the 5-year survival of each patient.

For gene expression analysis, FPKM values of indicated genes from tumor samples and corresponding normal tissue samples, if available, were plotted. The statistical significance difference of tumor versus non-tumor was calculated using the student t-test.

To analyze the association of PIK3R2 expression with 5-year survival, patients were divided into three groups according to their PIK3CA mutation status: helical domain mutation group (Patients with PIK3CA mutation at E542, E545, and Q546), non-helical domain mutation group (Patients with PIK3CA mutation at H1047 and other sites) and wild type group (Patients with wild-type PIK3CA), and then patients were further divided into PIK3R2 high and PIK3R2 low according to the median expression of PIK3R2 in each group. Due to the limitation of the patient number of helical domain mutation group in individual tumor type, PIK3R2 high and PIK3R2 low in each group of four tumor types were combined to assess the relevance of PIK3R2 expression and 5-year survival of all patients. Kaplan-Meier analysis of 5-year survival was performed with a Cox proportional hazards model.

Quantification and Statistical Analysis

GraphPad Prism software was used to create the graphs. Data are plotted as mean±SEM.

We applied the t-test to compare the means between the two groups, assuming unequal variances. For xenograft growth, we carried out ANOVA for repeated measurements to test whether there is an overall difference in the tumor sizes by testing group differences as well as whether there was a difference in the development of tumor sizes over time between the 2 groups by testing the interaction between time and group.

Results p85β Disassociates from p110α Helical Domain Mutant Protein

Figure 8A:
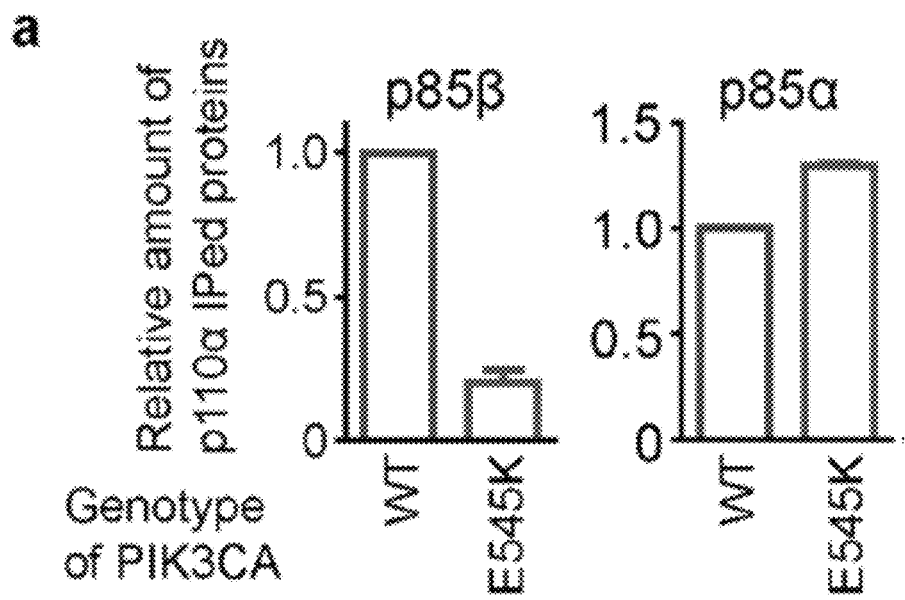
Figure 8B:
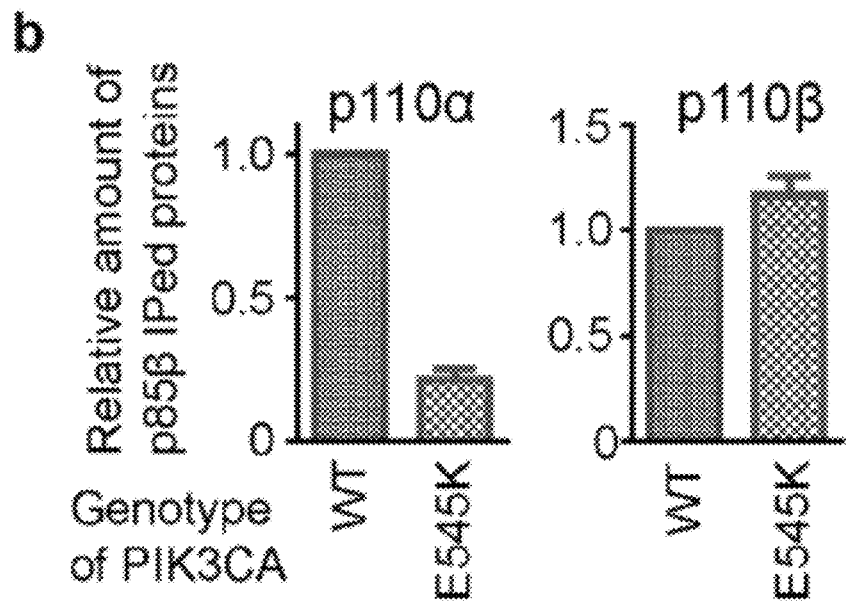
Figure 8C:
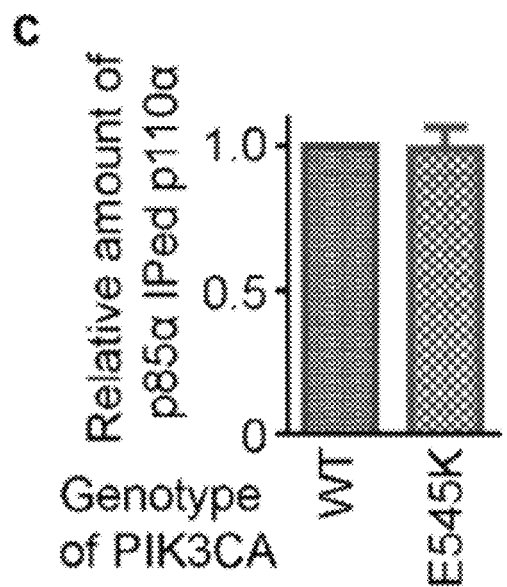
Figure 8D:
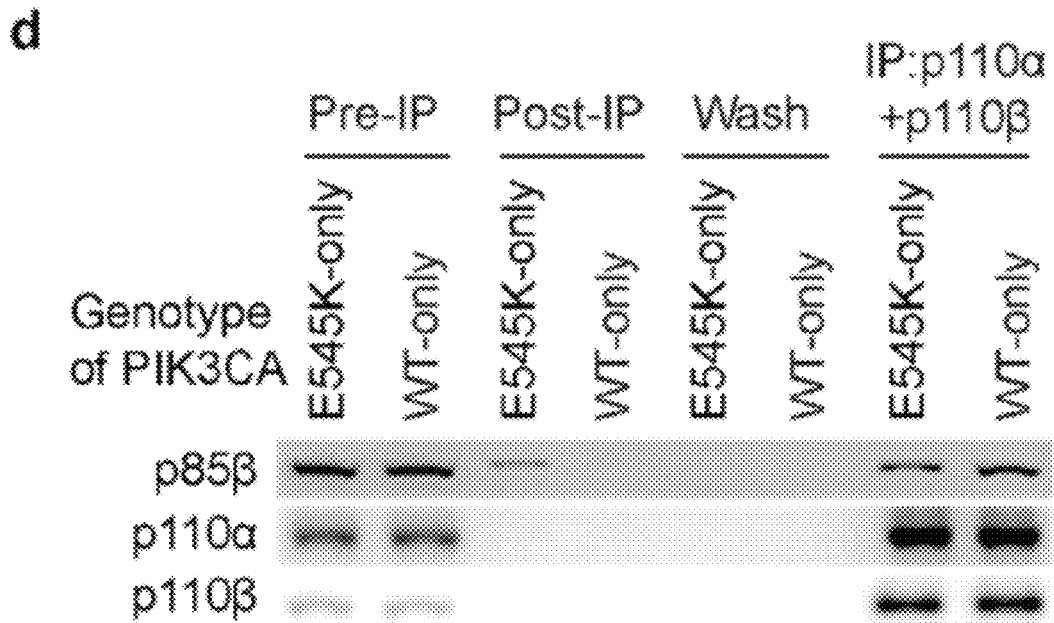
Figure 8E:
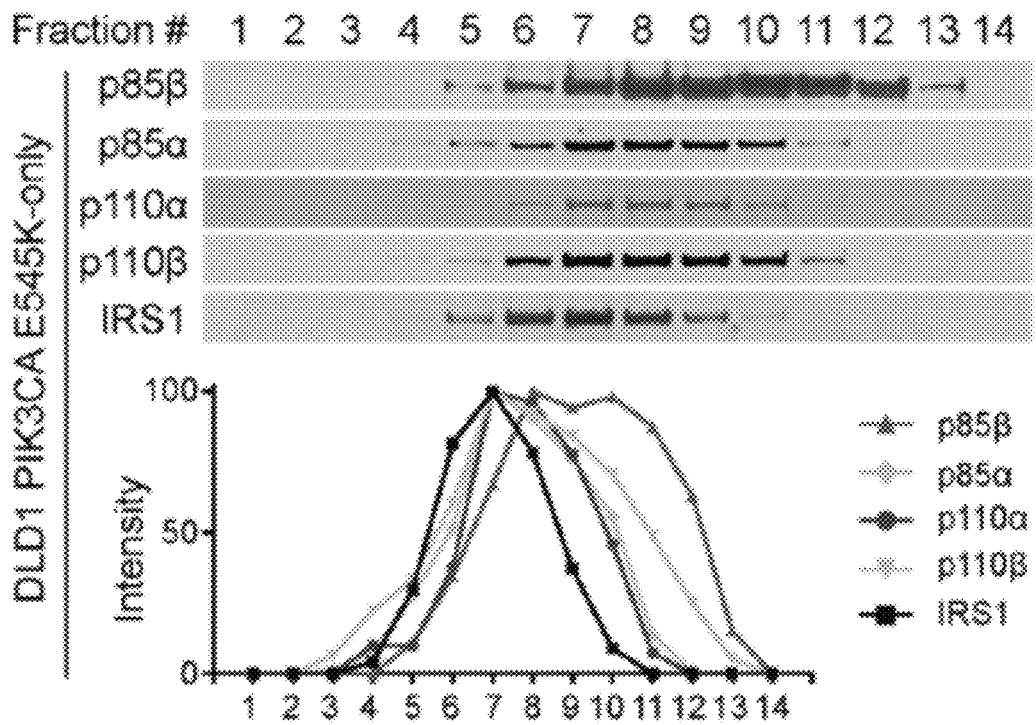
Figure 8E:
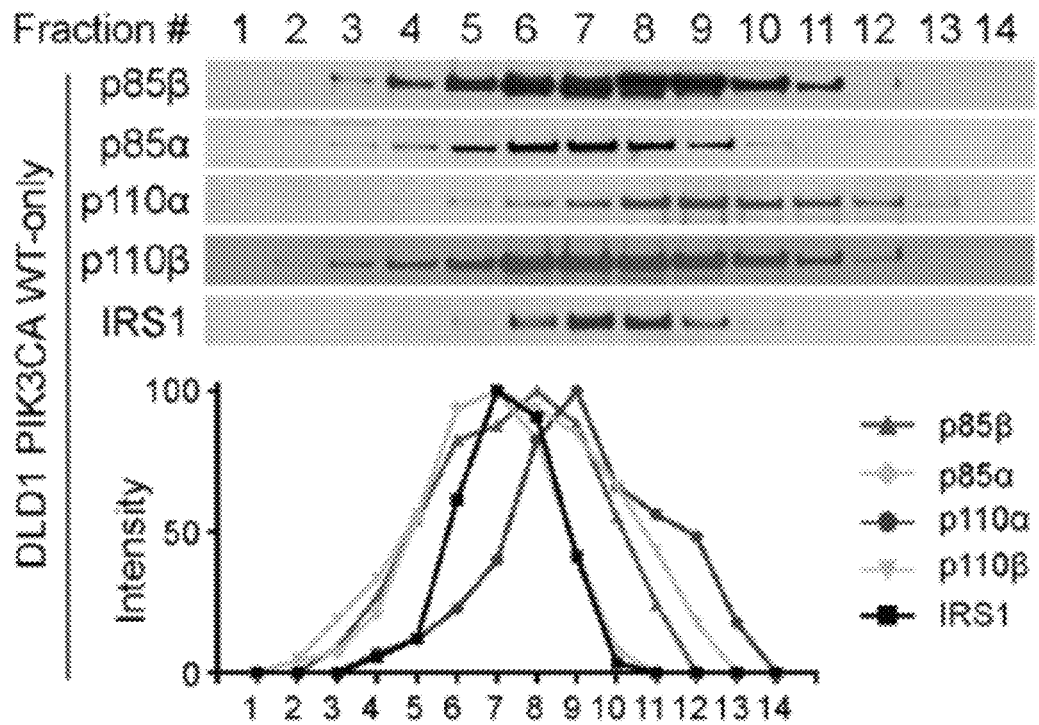

We previously demonstrated that p110α helical domain mutant proteins (e.g., E545K) gain direct interaction with IRS1 independent of p85α and β, thereby rewiring oncogenic signaling. To gain insights into how the p110α helical domain mutations impact PI3K complex formation, we immunoprecipitated either wild-type (WT) p110α or p110 α E545K mutant protein in cell lines with the WT or mutant endogenous p110α proteins tagged with 3×FLAG [FIG. 1A]. Interestingly, compared to the WT p110α protein, the p110 α E545K protein drastically reduced its binding to p85β, but not p85α (FIGS. 1B and 8A). This observation was further validated by reciprocal immunoprecipitation of either p85β or p85α in isogenic DLD1 cell lines with either WT-only (PIK3CA E545K allele knockout) or E545K-only (PIK3CA WT allele knockout, FIGS. 1C, 1D, 8B, and 8C). We postulated that some of the p85β proteins might disassociate from the PI3K complexes in PIK3CA E545K mutant cells. Indeed, immunoprecipitation with both p110α and p110β in the isogenic DLD1 E545K-only and WT-only cells showed more PI3K complex-free (post-IP) p85β were present in the E545K-only cells than in the WT-only cells (FIG. 8C). These results were further validated by gel-filtration analyses (FIG. 8E).

Figure 1E:
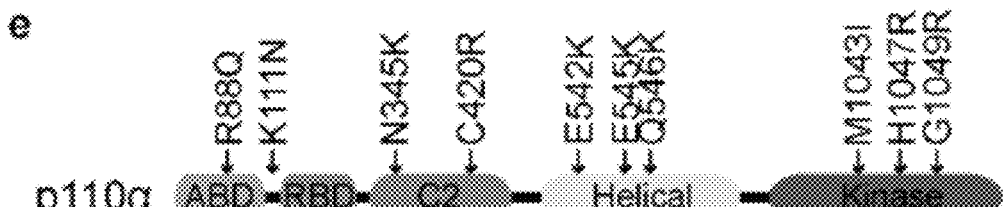
Figure 1F:
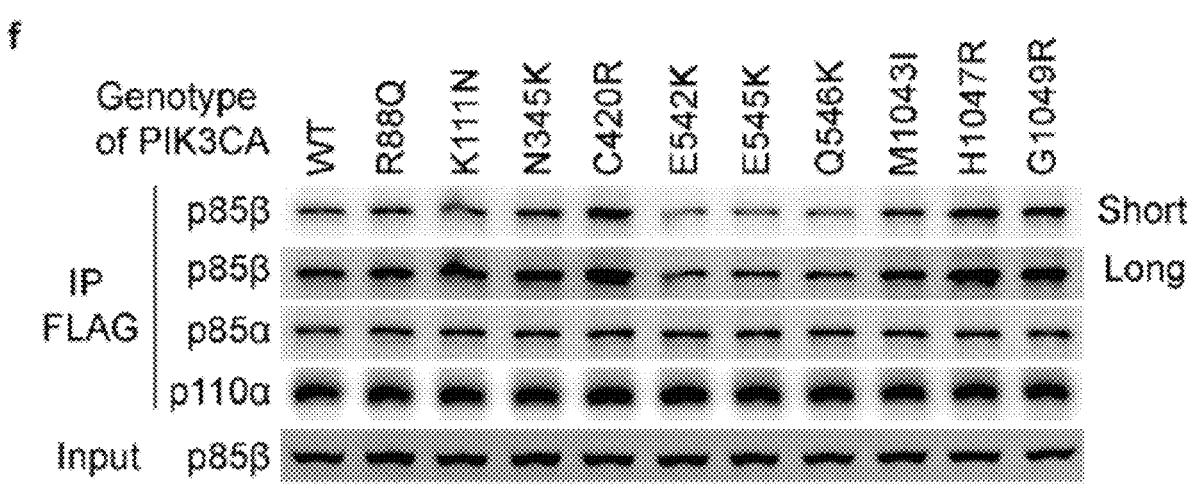
Figure 1G:
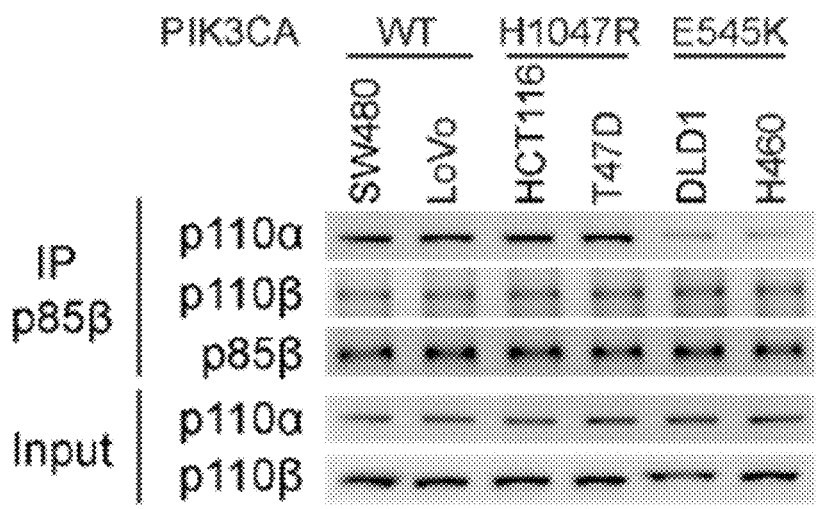
Figure 1H:
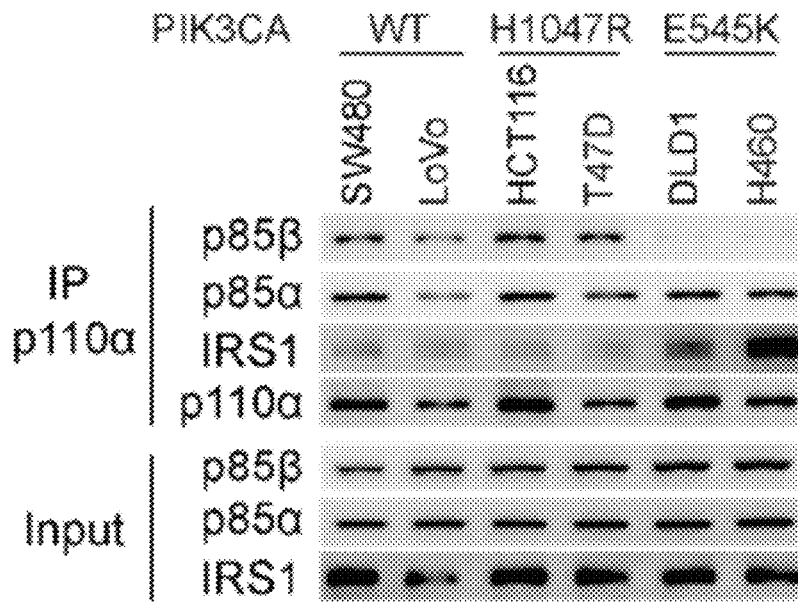
Figure 8F:
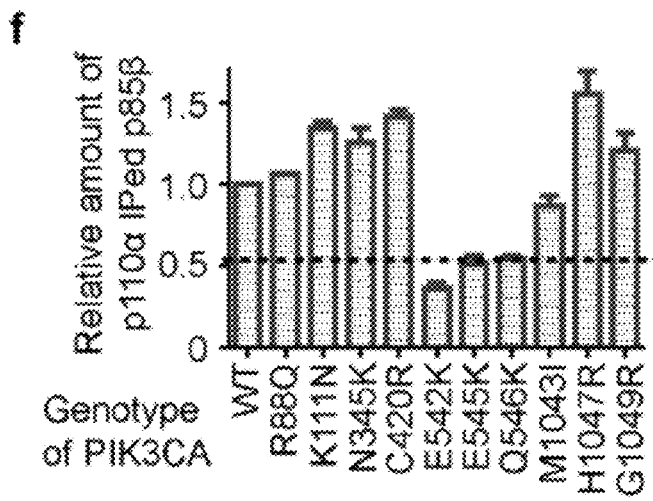
Figure 8G:
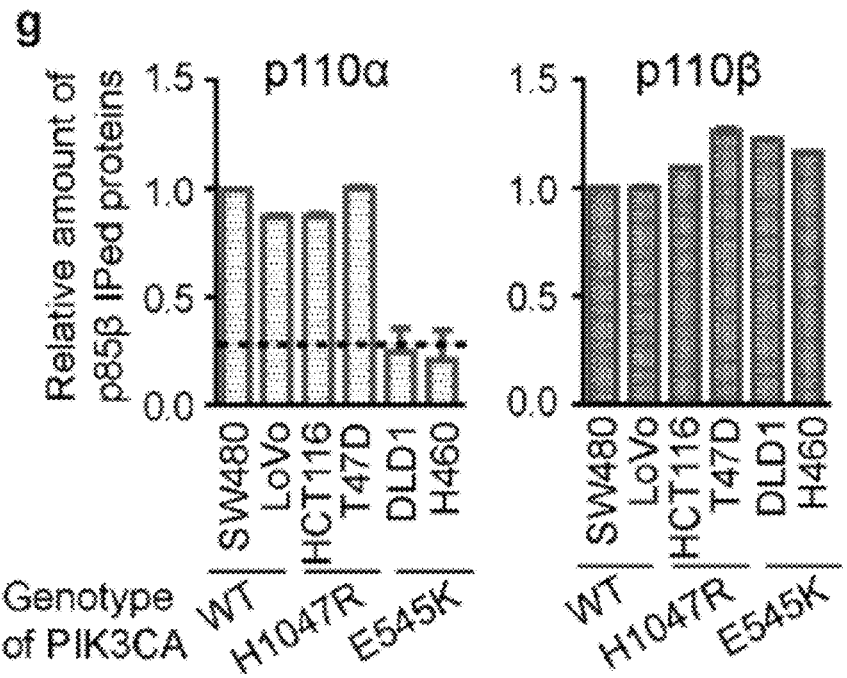
Figure 8H:
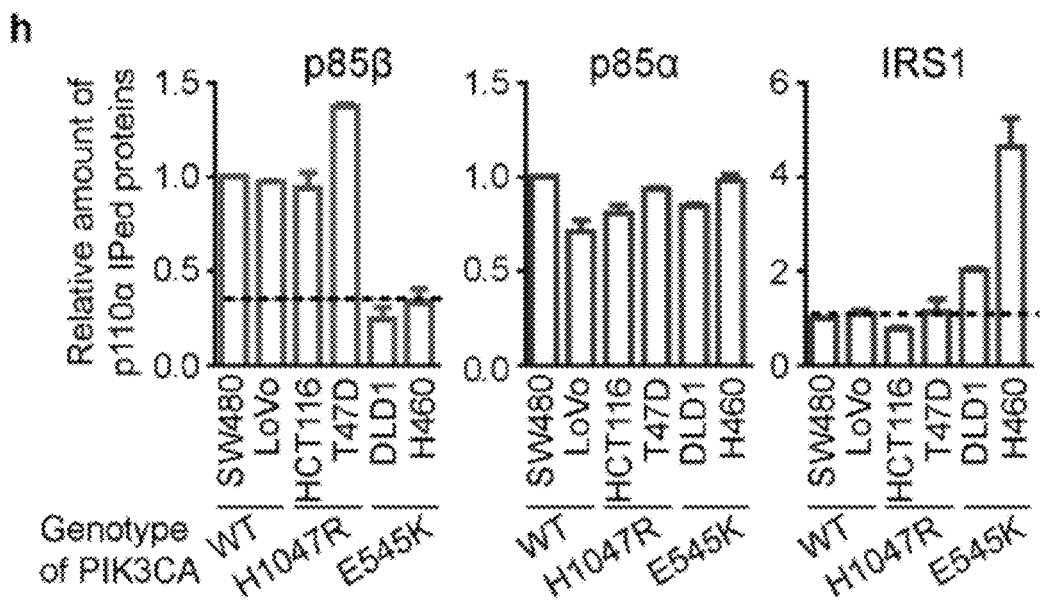

Tumor-derived PIK3CA mutations are clustered in two hotspots: one in the helical domain at E542, E545, Q546, and the other in the kinase domain at the H1047 site. We set out to determine which mutations in p110α affect binding to p85β. As shown in FIGS. 1E, 1F and 8F, as with the p110α E545K mutant, the p110α E542K and Q546K mutant proteins disrupted their interactions with p85β compared to the WT p110α. In contrast, the kinase domain p110α H1047R mutant protein had no impact on p85β binding. Neither did other relative rare p110α mutant proteins including R88Q and K111N in the ABD domain, N345K and C420R in the C2 domain, M1043I and G1049R in the kinase domain (FIGS. 1E, 1F, and 8F).

We then used six different cell lines to assess p85β-p110 complex formation. Consistently, the interaction between p85β and p110α were weaker in two cell lines with PIK3CA E545K mutation (DLD1 and H460) than in either two cell lines with wild-type PIK3CA (SW480 and LoVo) or two cell lines with PIK3CA H1047R mutation (HCT116 and T47D) (FIGS. 1G, 1H, 8G, and 8H). In contrast, the interactions between p85β and p110β or between p85α and p110α were similar in these six cell lines (FIGS. 1G, 1H, 8G, and 8H). Together, our data suggest that the p85β protein dissociates from the mutant p110α in cancer cells with a PIK3CA helical domain mutation.

Figure 1I:
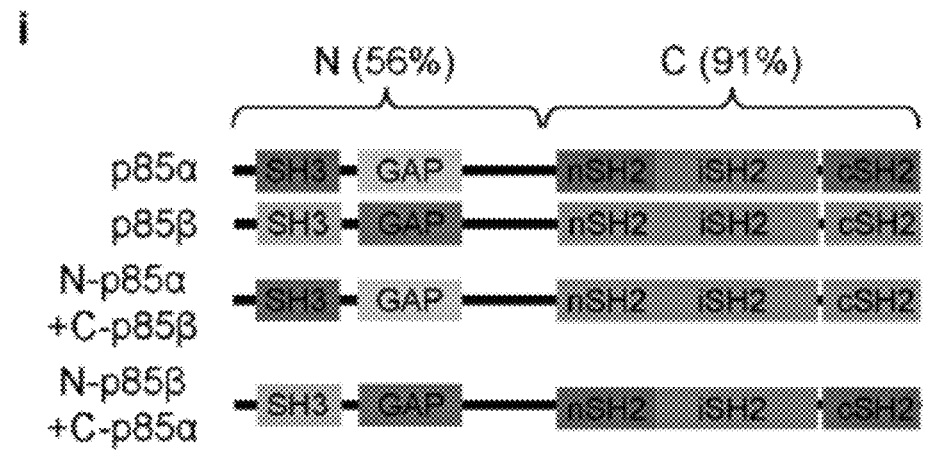
Figure 1J:
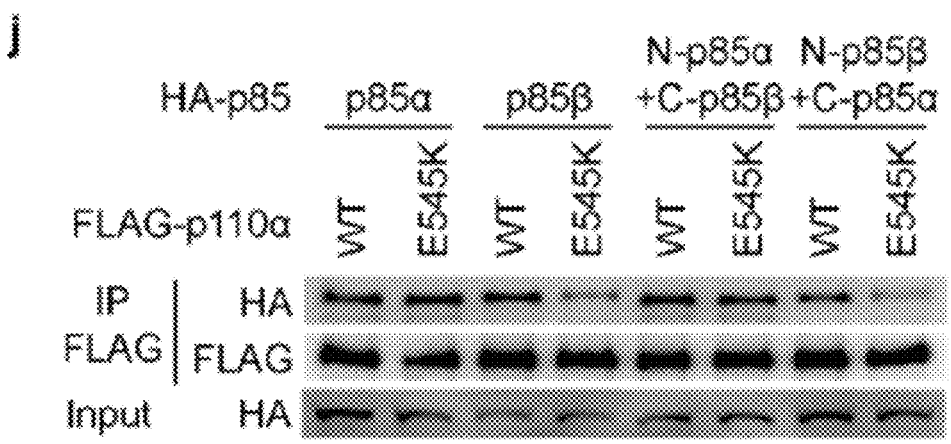
Figure 2A:
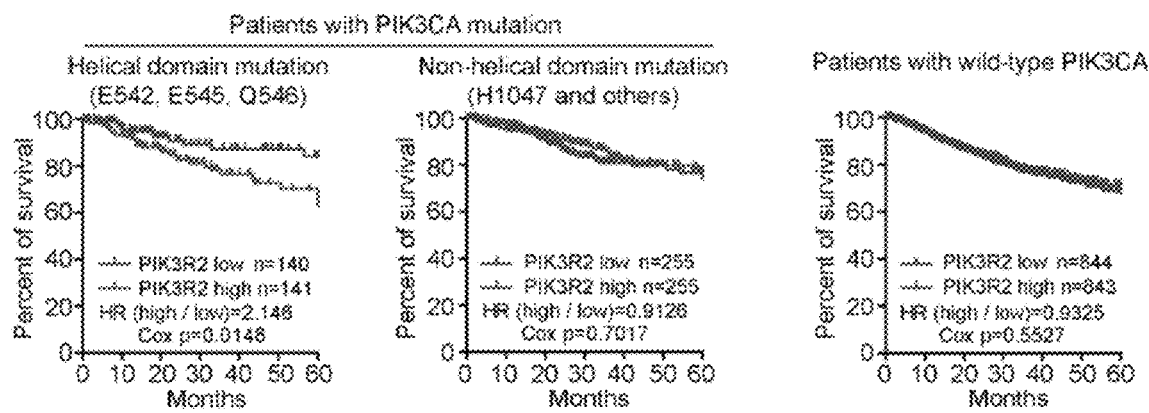
Figure 9A:
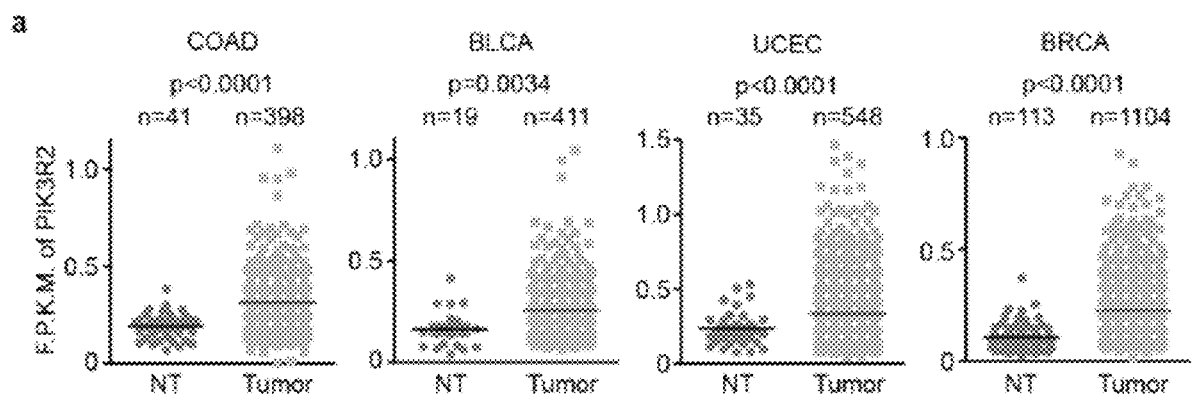
Figure 9B:
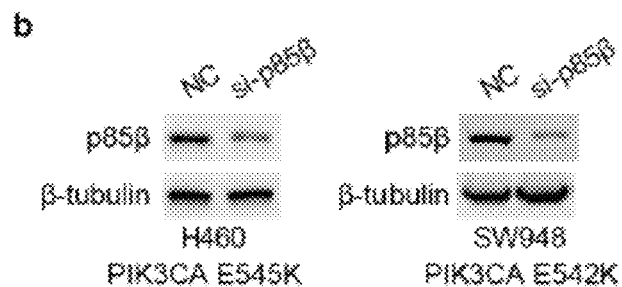
Figure 9C:
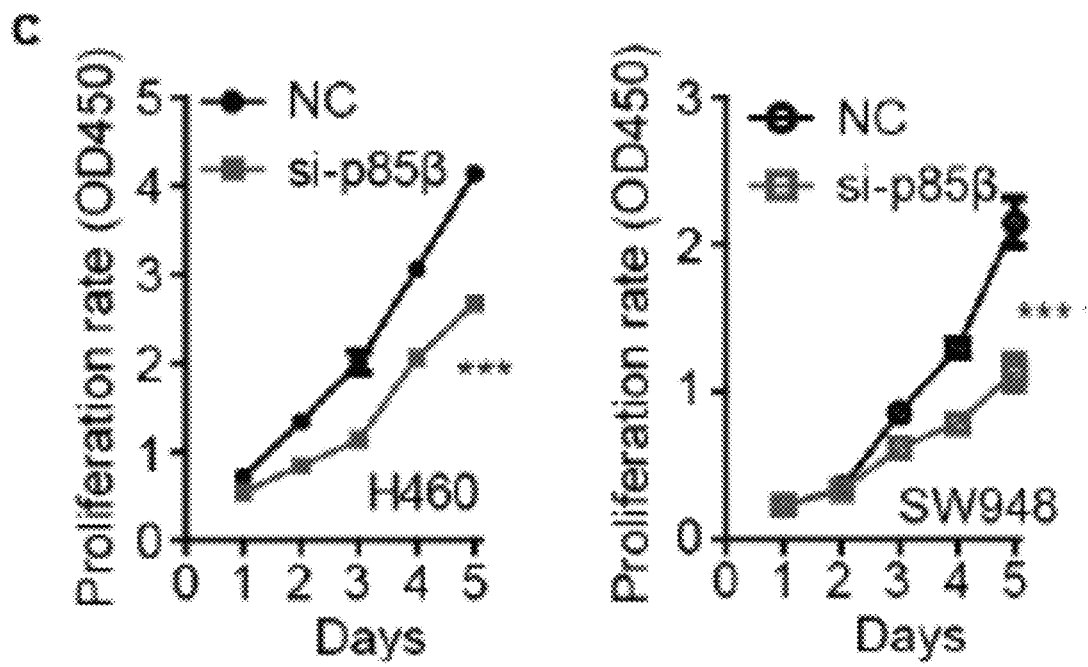
Figure 9D:
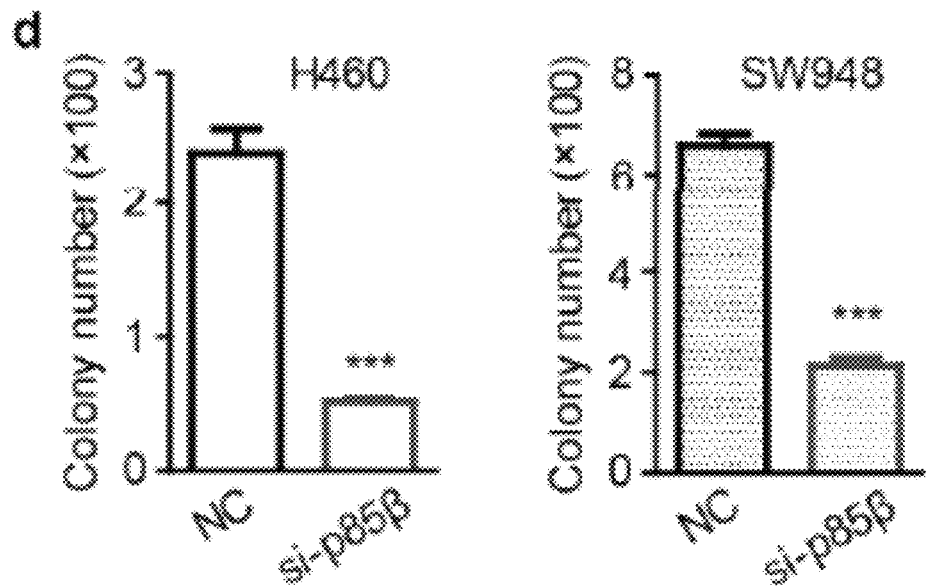
Figure 9E:
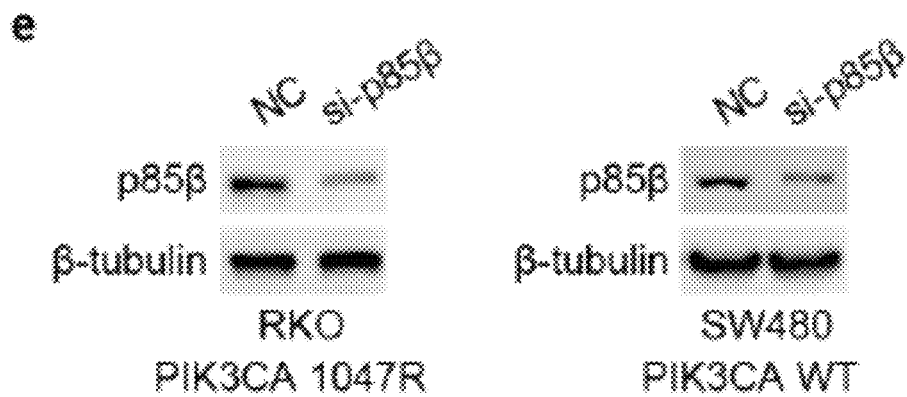
Figure 9F:
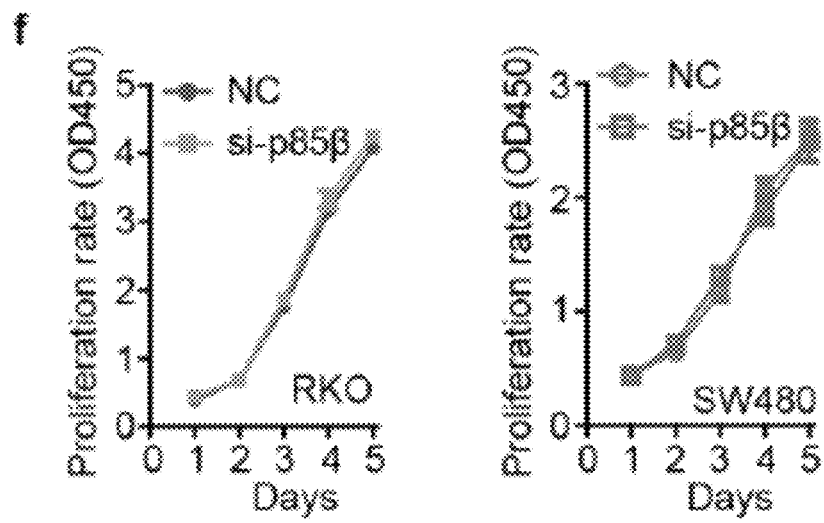
Figure 9G:
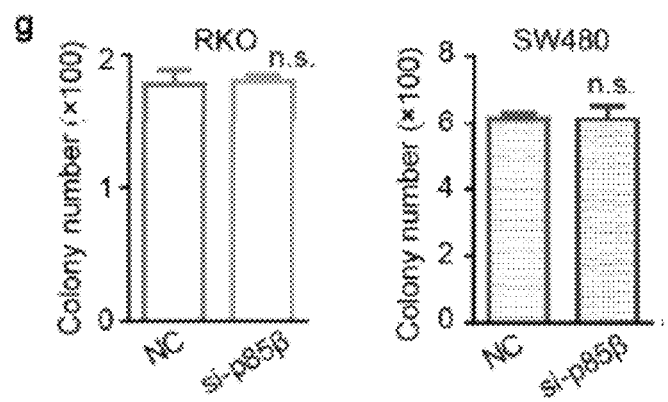

The N-Terminal p85β Sequences Cause its Dissociation from p110α Helical Domain Mutant Protein It is interesting that p85β, but not p85α, disassociates from the p110α helical domain mutant proteins. A protein sequence alignment showed that the SH3 domain, GAP domain, and link region between the GAP and nSH2 domains in the N-terminus sequences between p85α and p85β are less conserved (56% identical, FIG. 1I). In contrast, the three SH2 domains in the two proteins' C-terminus are highly conserved (91% identical, FIG. 1I). We postulated that the N-terminus sequences of p85β might cause its disassociation from the p110α helical domain mutant proteins. To this end, we constructed two chimeric p85 proteins that swapped the N-terminus regions of p85α and p85β (FIG. 1I). As shown in FIG. 1J, the N-terminal p85α-C-terminal p85β chimeric proteins bound similarly to both p110α WT and E545K mutant proteins, whereas the N-terminal p85β-C-terminal p85α chimeric protein bound to less p110α E545K mutant protein compared to the WT counterpart (FIG. 1J). These data suggest that the N-terminal sequences of p85β cause its disassociation from the p110α helical domain mutant proteins.

p85β Plays an Oncogenic Role in Cancer Cells with a PIK3CA Helical Domain Mutation To explore the specific function of p85β in p110α helical domain mutated tumors, we assessed whether p85β expression levels are associated with any clinical outcomes. We chose to analyze the following four TCGA datasets because PIK3CA is frequently mutated, and PIK3R2 is overexpressed in these tumor types: colorectal cancer (COAD), bladder carcinoma (BLCA), endometrial carcinoma (UCEC), and breast cancer (BRCA) (FIG. 9A). Because the number of patients whose tumors harbor PIK3CA mutations is small in each tumor type, we combined the TCGA data of the four tumor types together and divided the patients into three groups according to the PIK3CA mutation status: helical domain mutation group, non-helical domain mutation group, and wild-type group. Interestingly, high expression of PIK3R2 was found to be significantly associated with poor five-year survival only in the helical domain mutation group (HR=2.146, 95% CI 1.162~3.96, p=0.0148), but not in the non-helical domain mutation group (HR=0.9126, 95% CI 0.5714~1.4, p=0.7017) or wild-type group (HR=0.9325, 95% CI 0.7404~1.1, p=0.5527) (FIG. 2A). These data suggest that p85β may promote tumorigenesis in tumors with a PIK3CA helical domain mutation.

Figure 2B:
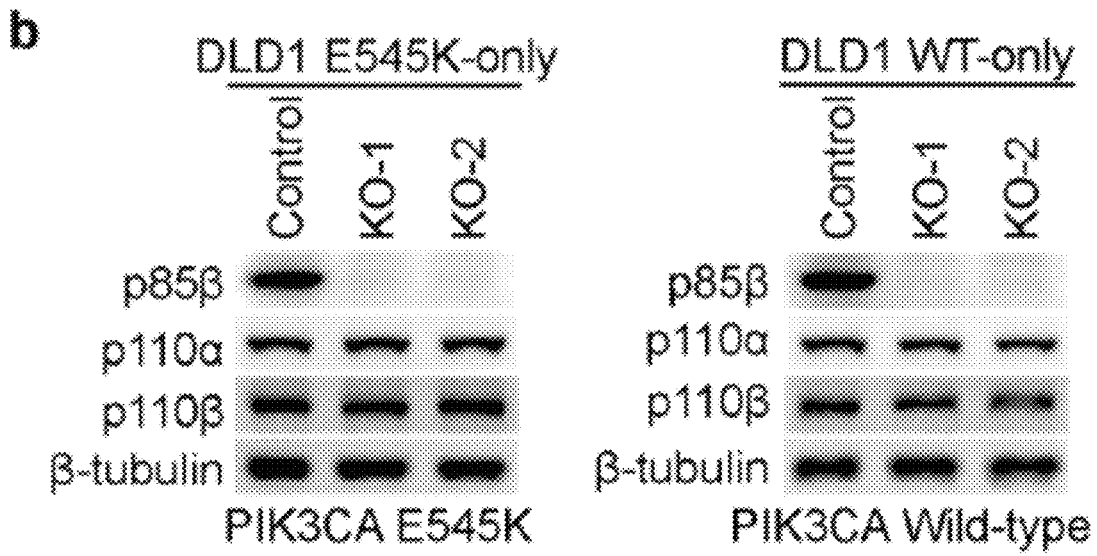
Figure 2C:
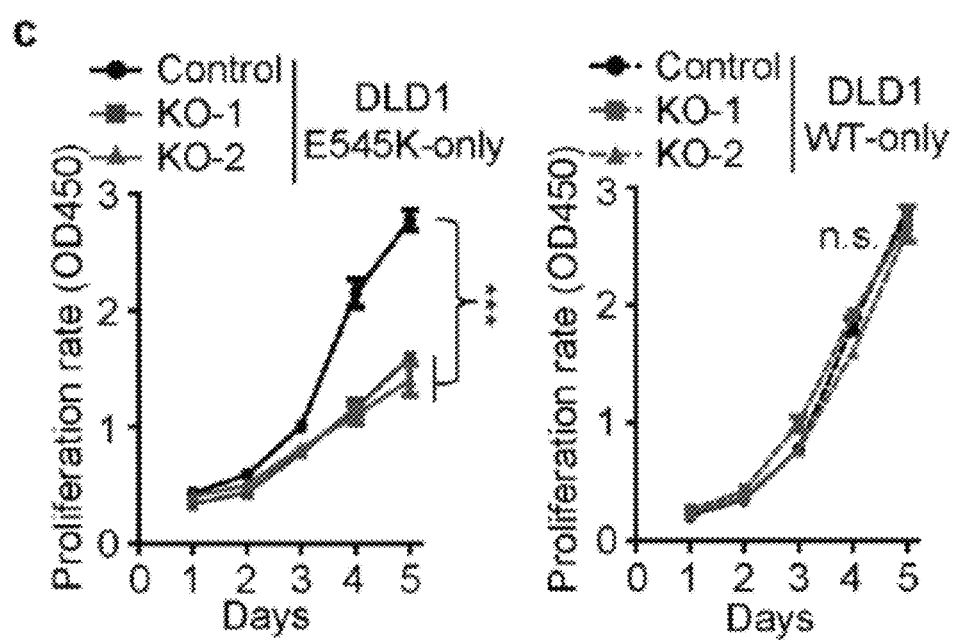
Figure 2D:
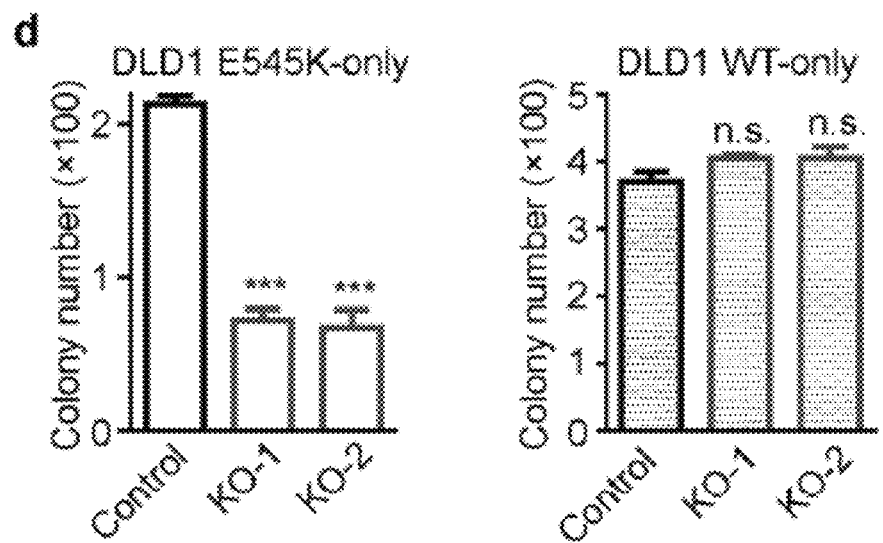
Figure 2E:
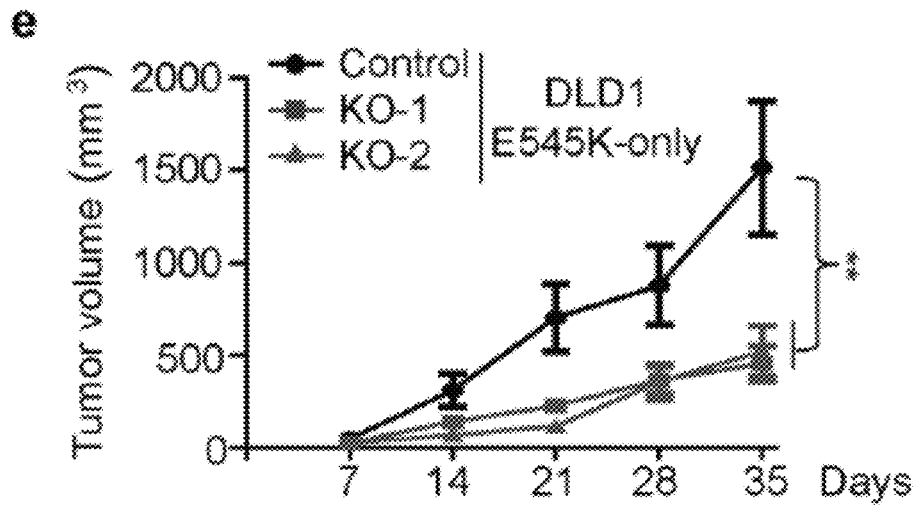
Figure 2F:
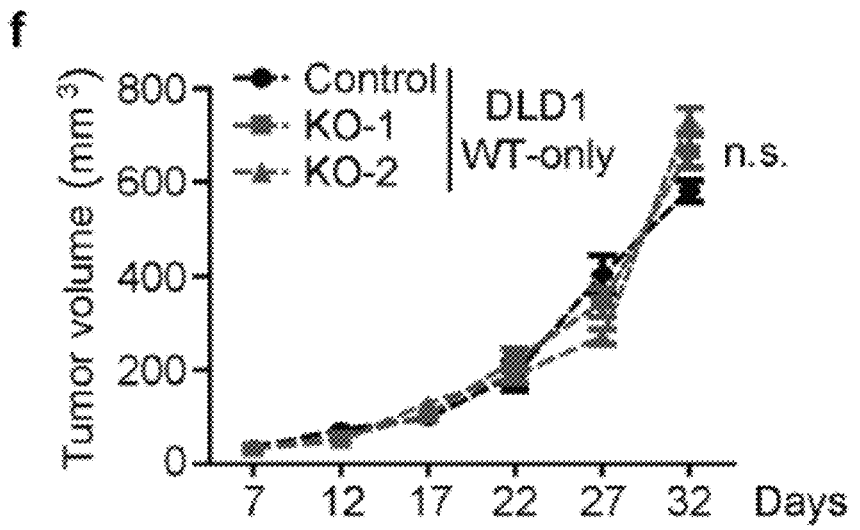
Figure 2G:
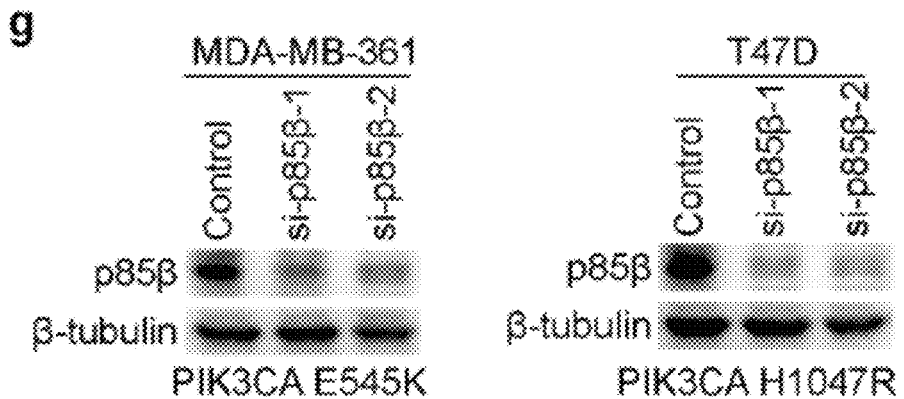
Figure 2H:
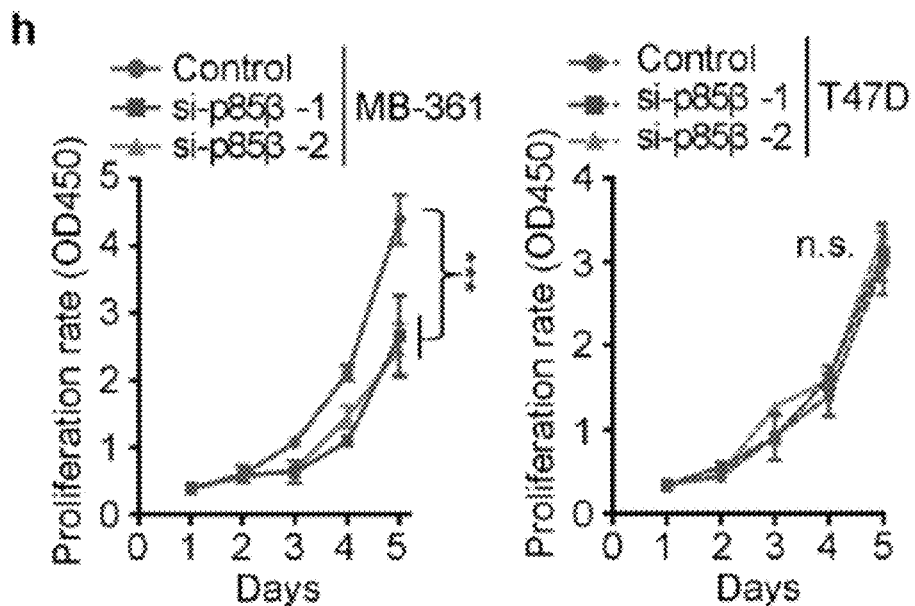
Figure 2I:
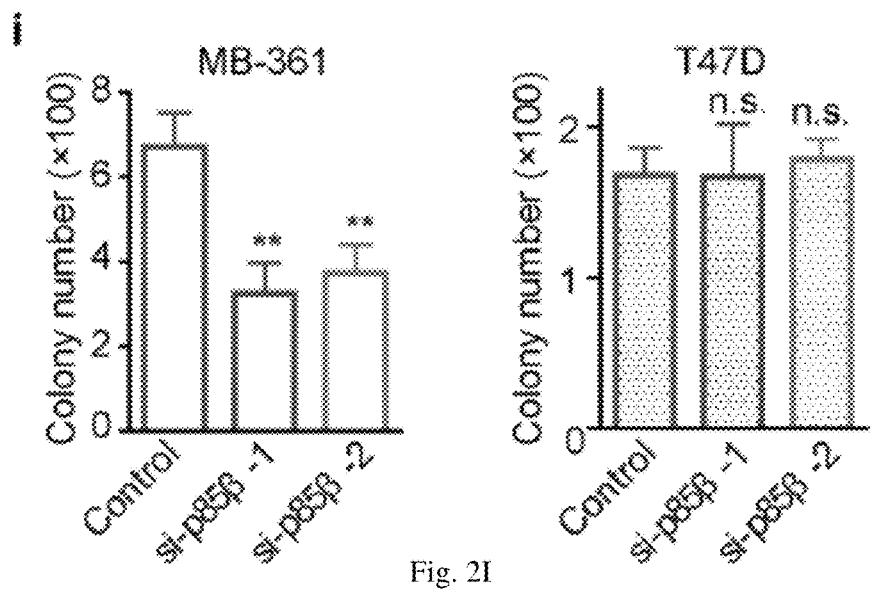
Figures 9H, 10A:
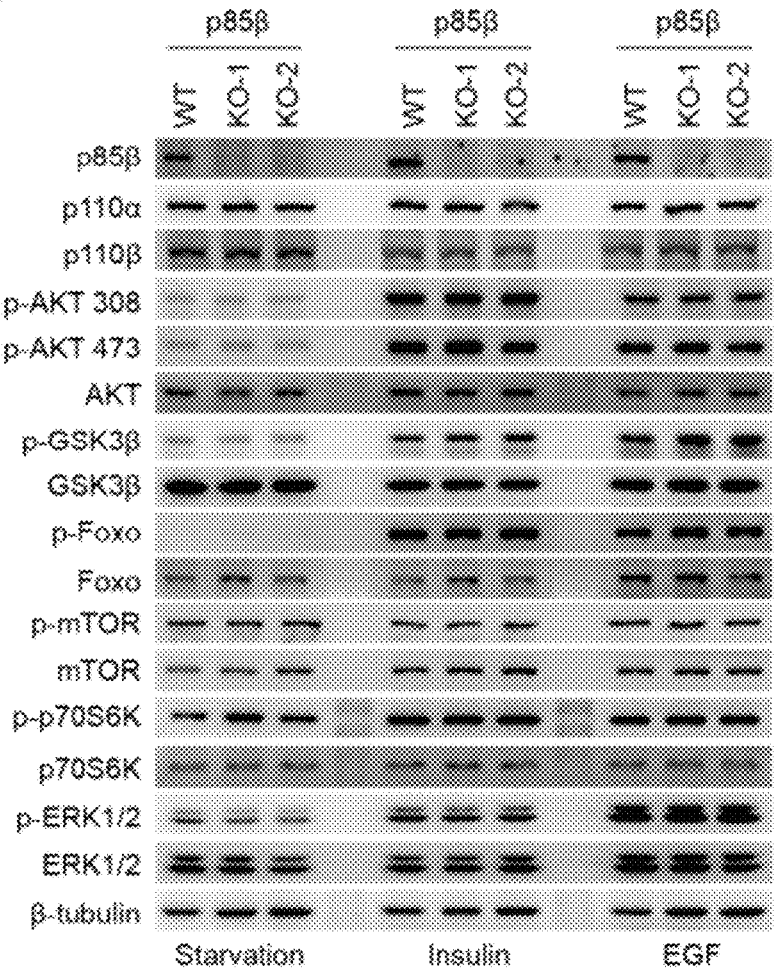
Figure 10B:
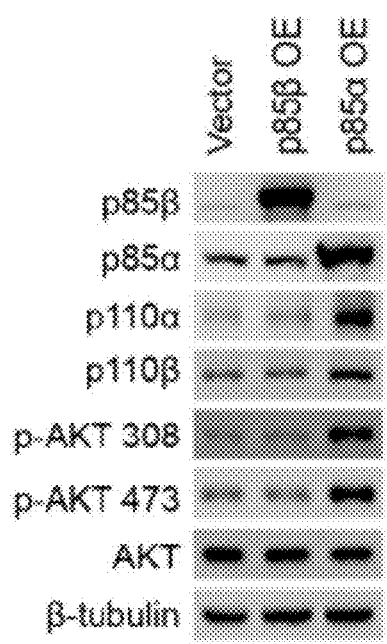

The Depletion of p85β Reduces the Growth of Cancer Cells with a PIK3CA Helical Domain Mutation, but not Cells with WT or a Kinase Domain Mutant PIK3CA To further investigate the function of p85β in the context of PIK3CA helical domain mutation, we knocked out p85β in the isogenic DLD1 PIK3CA E545K-only and PIK3CA WT-only cell lines (FIG. 2B). As shown in FIGS. 2C to 2F, knockout of p85β reduced cell proliferation, colony formation, and xenograft tumor growth of the DLD1 PIK3CA E545K-only cells, but not the WT PIK3CA-only counterpart. Similarly, knockdown of p85β reduced cell proliferation and colony formation of PIK3CA E545K mutant MDA-MB361 breast cancer cells and H460 lung cancer cells and PIK3CA E542K mutant SW948 cells (FIGS. 2G-I, 9B-D). In contrast, knockdown of p85β had no impact on cell proliferation and colony formation of PIK3CA H1047R mutant T47D breast cancer cells and RKO colon cancer cells, or PIK3CA WT SW480 cells (FIGS. 2G-O, 9E-H). Together, these data suggest that p85β promotes the growth of tumors harboring PIK3CA helical domain mutations, but not those tumors with WT or PIK3CA kinase domain mutations.

p85β Translocates into the Nucleus in Cancer Cells with a PIK3CA Helical Domain Mutation Next, we set out to elucidate the molecular mechanisms by which p85β promotes the growth of cancer cells with a PIK3CA helical domain mutation. Given that it is well documented that PI3K transduces signaling to AKT, we examined whether p85β knockout impacts AKT and its downstream signaling. As shown in FIG. 10A, knockout of p85β did not affect phosphorylation of AKT, GSK3β, Foxo, mTOR, and p70S6K in DLD1 PIK3CA E545K-only cells regardless of whether under serum starvation conditions or when stimulated by insulin or EGF. Moreover, neither knockout of p85β impacted p110α and p110β protein levels in PIK3CA mutant-only cells (FIG. 10A), nor did overexpression of p85β affect the levels of p110α, p110β, and AKT phosphorylation in DLD1 PIK3CA E545K-only cells (FIG. 10B). In contrast, overexpression of p85α increases the levels of p110α, p110β and AKT phosphorylation (FIG. 8B). Those data suggest that p85α, but not p85β, is the major regulatory subunit for PI3K activity in DLD1 colorectal cancer cells.

Figure 3A:
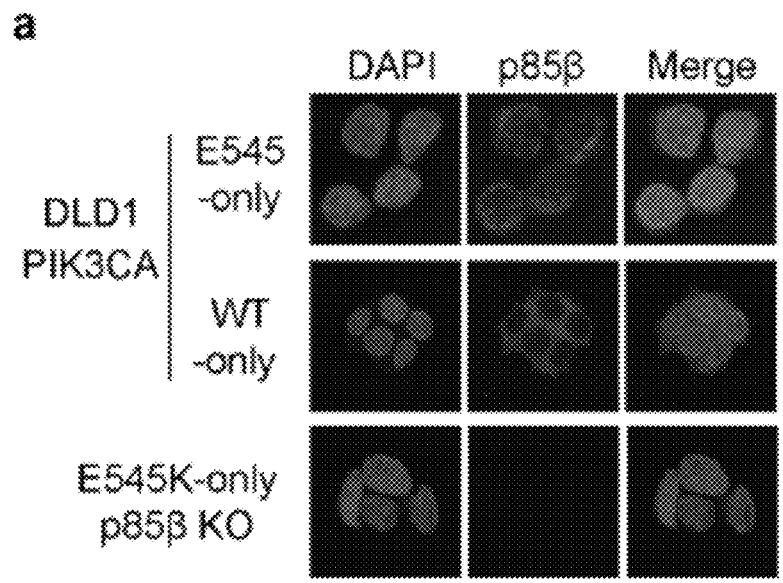
Figure 3B:
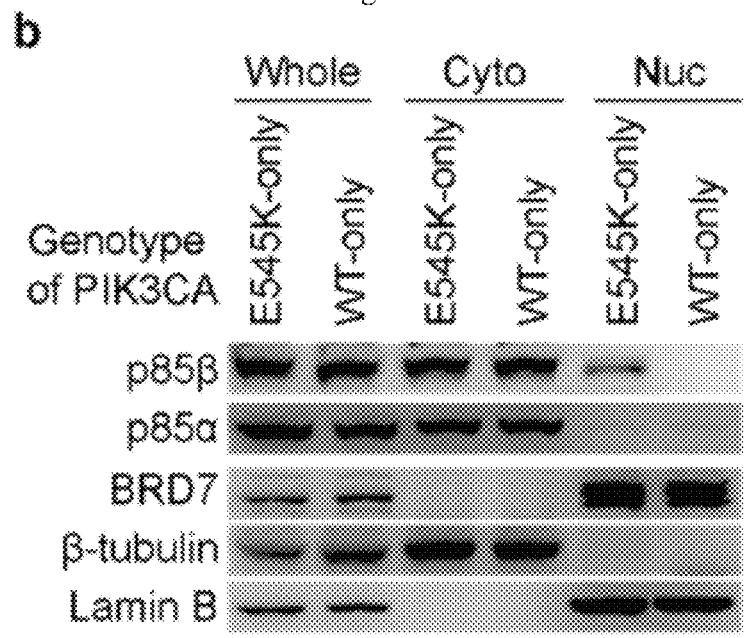
Figure 3C:
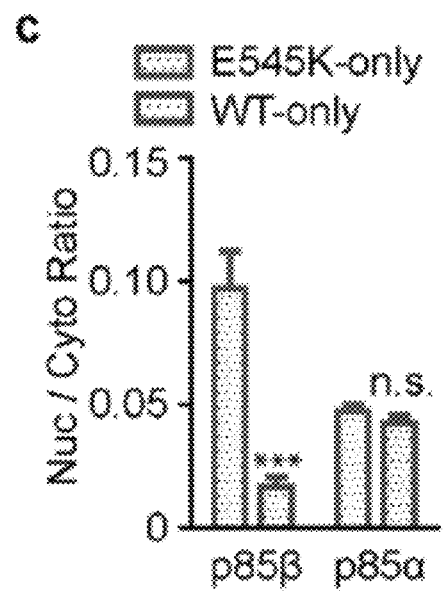
Figure 3D:
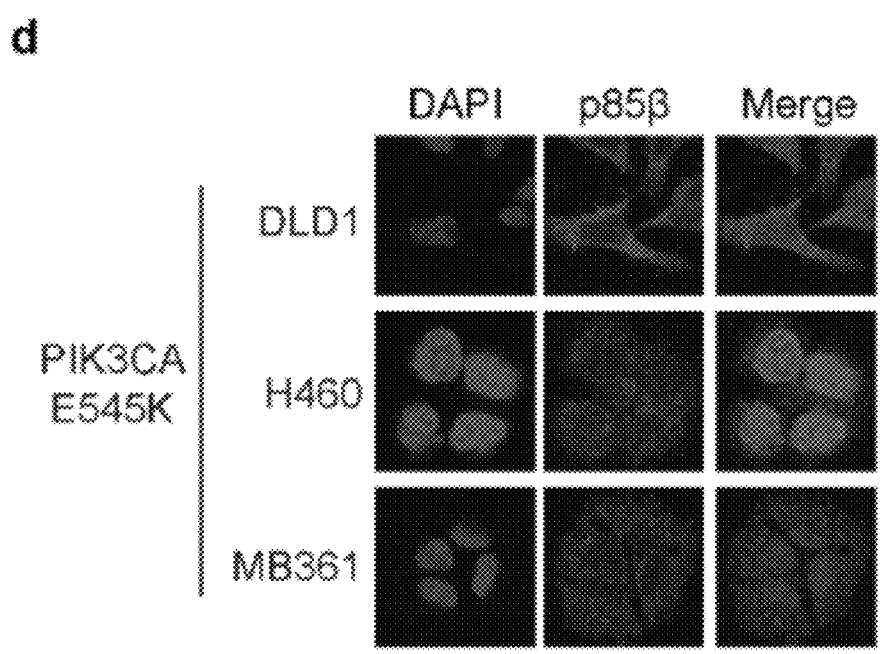
Figure 3E:
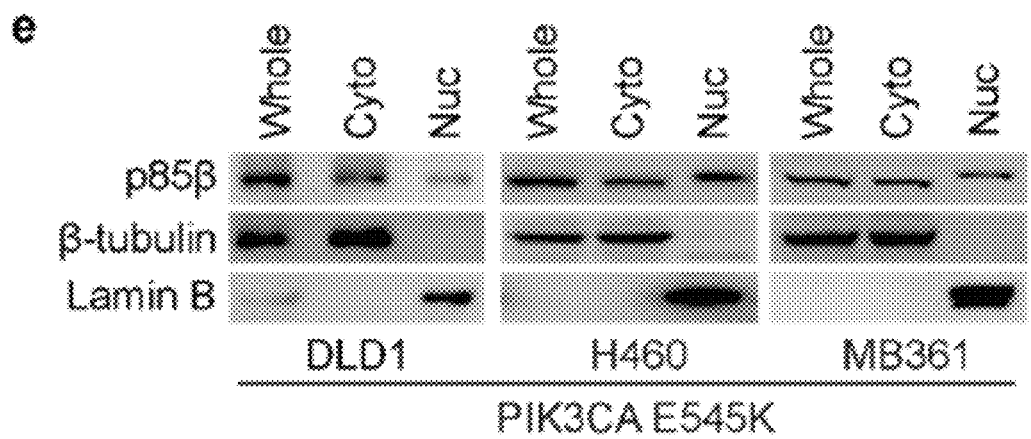
Figure 3F:
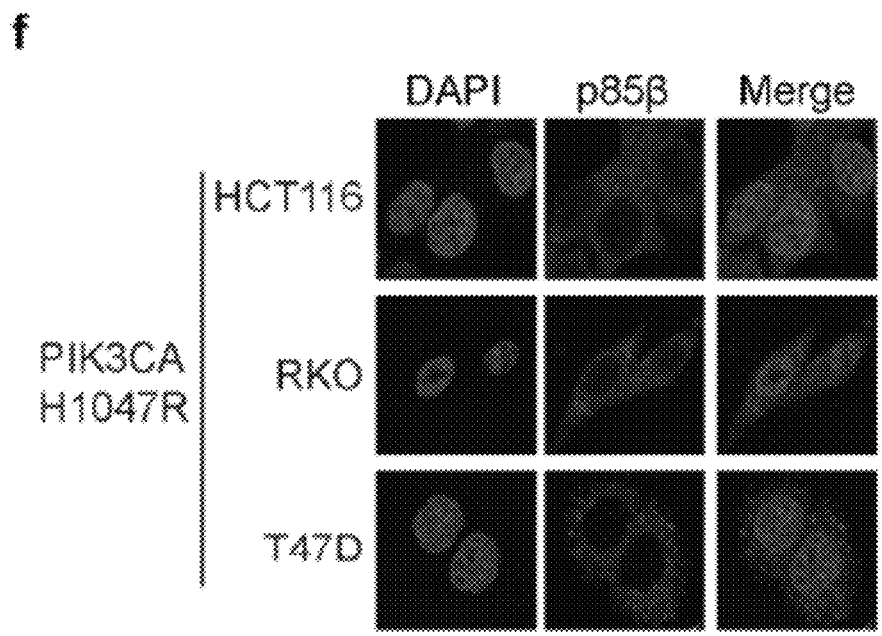
Figure 3G:
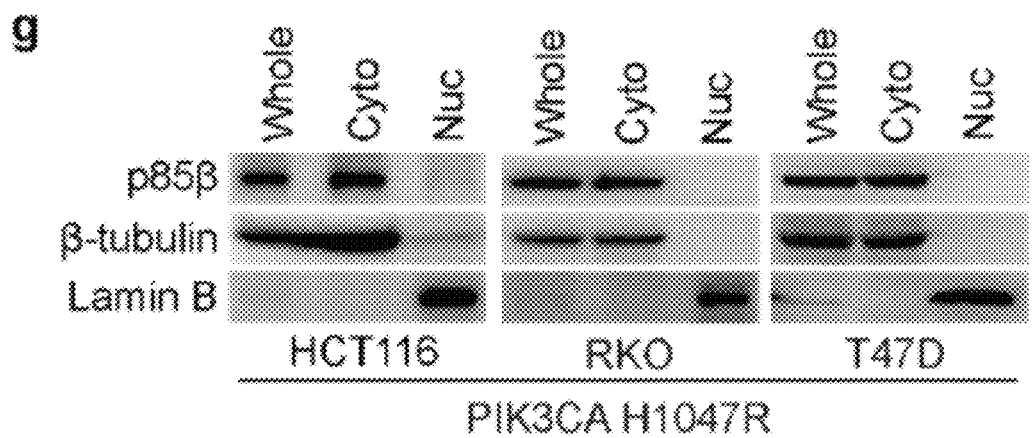
Figure 3H:
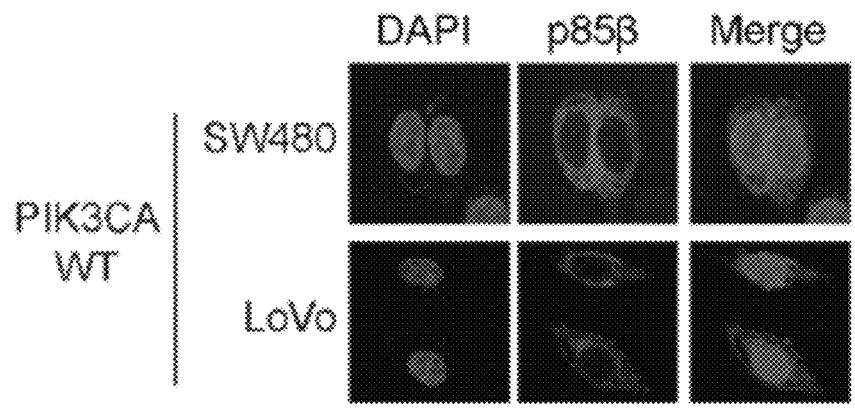
Figure 3I:
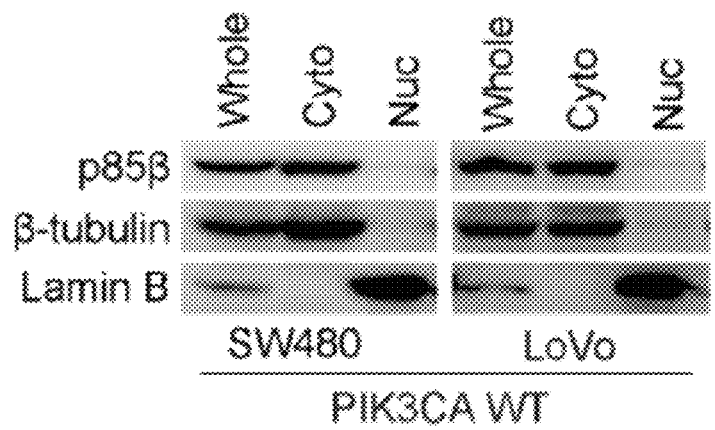
Figure 3J:
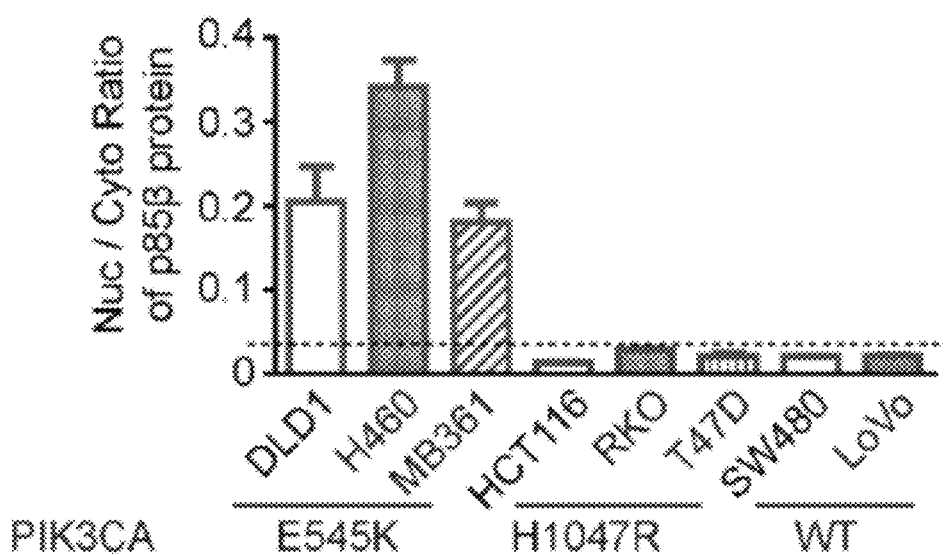
Figure 10C:
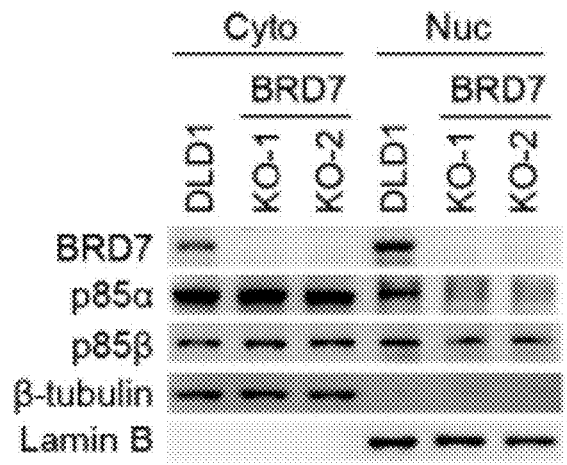
Figure 10D:
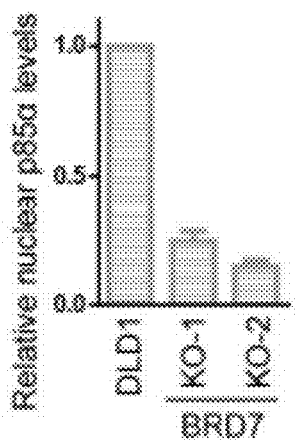
Figure 10D:
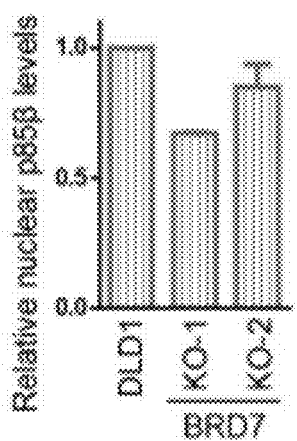

It has been reported that p85 proteins can translocate to the nucleus. We thus performed immunofluorescent staining of p85β in the isogenic DLD1 PIK3CA E545K-only and PIK3CA WT-only cell lines. As shown in FIG. 3A, p85β was present in both nucleus and cytoplasm in the DLD1 PIK3CA E545K-only cells, but only in the cytoplasm in the DLD1 PIK3CA WT-only cells. The specificity of the anti-p85β antibody was demonstrated by the lack of staining in the DLD1 PIK3CA E545K-only p85β knockout cells (FIG. 3A). Consistently, cell fractionation analyses showed that significantly more p85β was located in the nucleus in the DLD1 PIK3CA E545K-only cells than in the DLD1 PIK3CA WT-only cells (FIGS. 3B & 3C). In agreement with previous reports, a small fraction of p85α was also present in the nucleus (FIG. 3B), although the amounts of nuclear p85α were similar between the isogenic DLD1 PIK3CA E545K-only cells and DLD1 PIK3CA WT-only cells (FIG. 3C). Because BRD7 was reported to facilitate nuclear translocation of p85α, we compared BRD7 protein levels between the DLD1 PIK3CA E545K-only and PIK3CA WT-only cells. FIG. 3B shows that BRD7 proteins were largely localized to the nucleus to a similar degree in the two cell lines, suggesting that the differential nuclear localization of p85β in the DLD1 PIK3CA E545K cells is unlikely to be mediated by BRD7. Consistently, knockout of BRD7 in DLD1 cells largely abolished nuclear translocation of p85α but not p85β (FIGS. 10C and D).

Figure 10E:
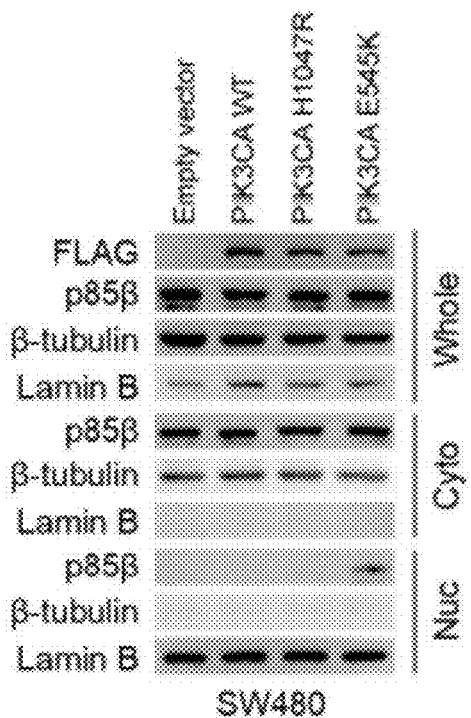
Figure 10F:
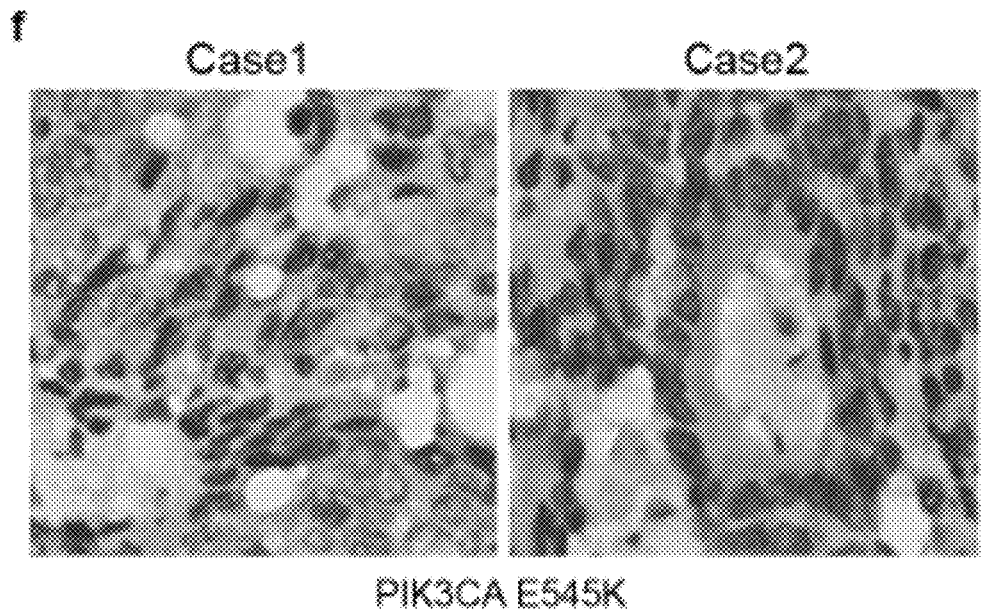
Figure 10G:
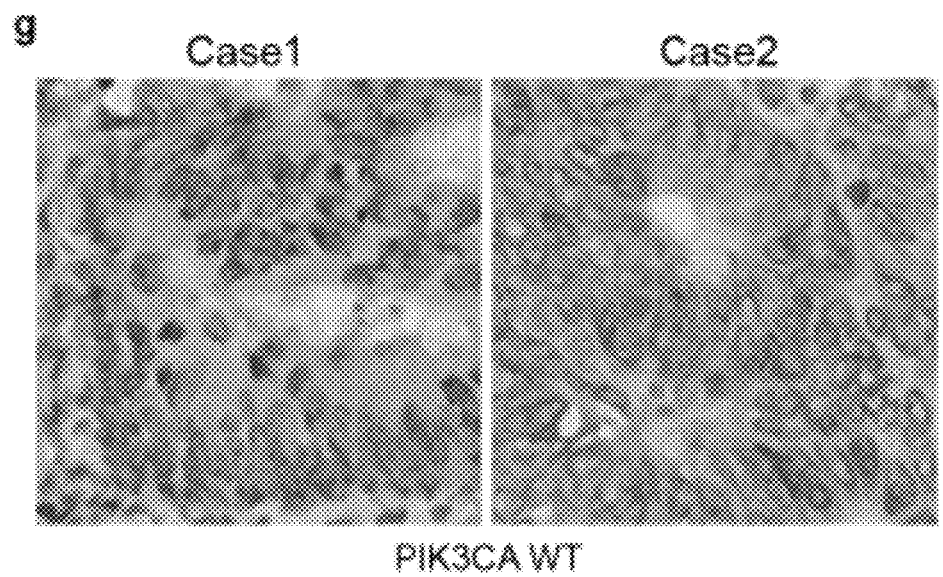

To assess the generality and specificity of p85β nuclear localization in PIK3CA helical domain mutant cells, we analyzed cellular localization of p85β in a panel of cell lines: two additional PIK3CA E545K mutant cell lines (H460 and MB361); three PIK3CA H1047R mutant cells lines (HCT116, RKO, and T47D); and two WT PIK3CA cell lines (SW480 and LoVo). Both immunofluorescent staining and cell fractionation demonstrated that p85β was translocated into the nucleus in the cell lines with a PIK3CA E545K mutation, but not in cell lines with WT PIK3CA or H1047R mutation (FIGS. 3D to 3J). Furthermore, overexpressing PIK3CA E545K protein into SW480 cells facilitates the nuclear translocation of p85β (FIG. 10E). Consistently, compared to PIK3CA wild-type tumors, immunohistochemistry staining of human colon cancer specimens showed that p85β was predominantly localized in the nuclei of tumors with a PIK3CA E545K mutation (FIG. 10F), but mostly localized in the cytoplasm of tumors with wild-type PIK3CA (FIG. 10G). Together, those data suggest that p85β dissociates from the PI3K complexes and translocates into the nucleus in cancer cells with a PIK3CA helical domain mutation.

Figure 4D:
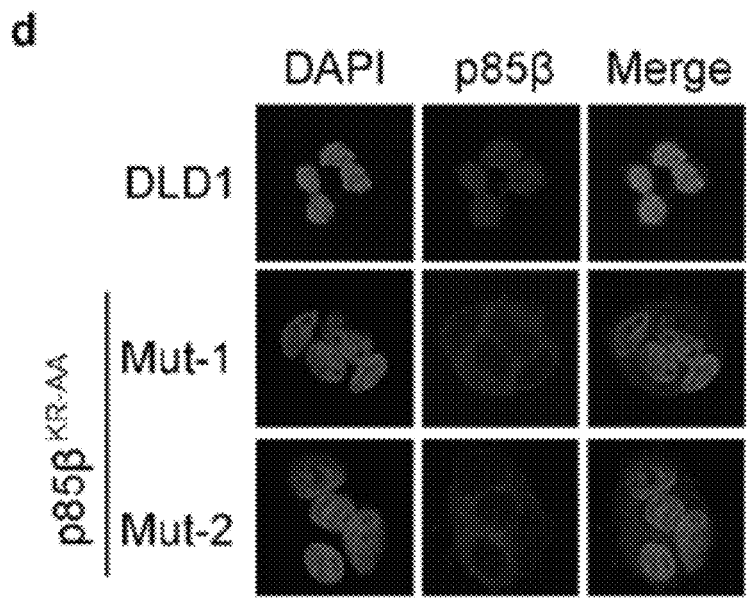
Figure 4E:
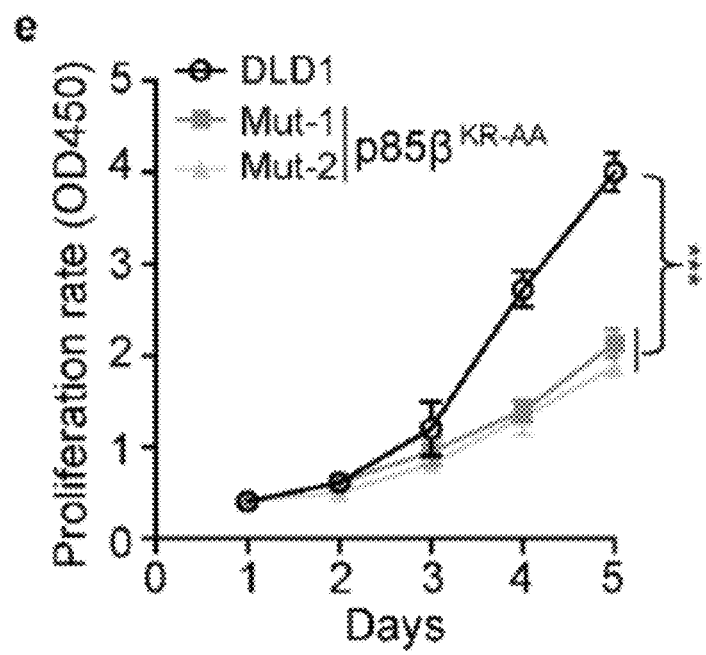
Figure 4F:
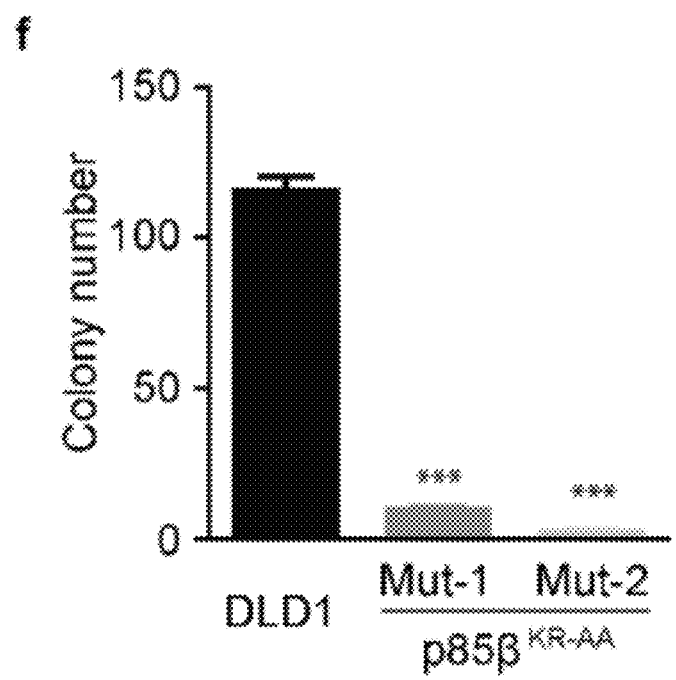
Figure 4G:
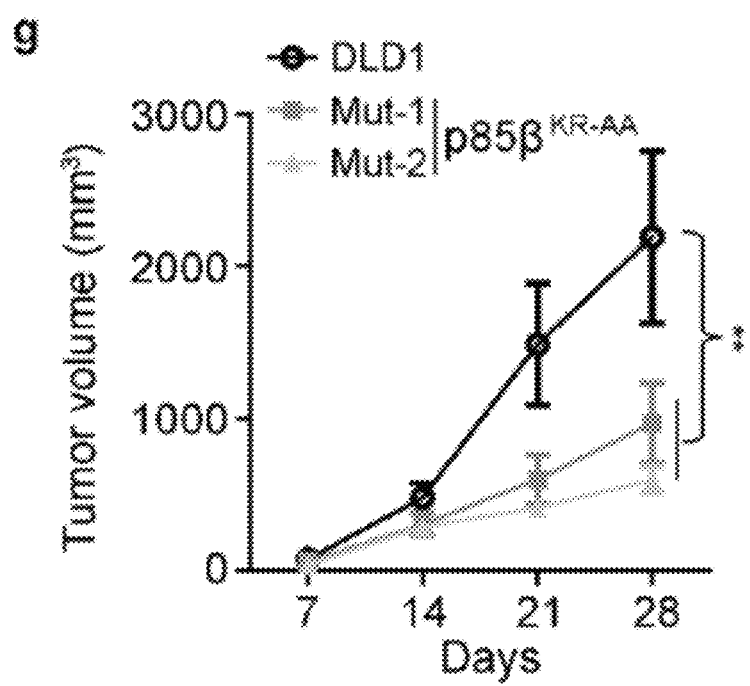
Figure 11A:
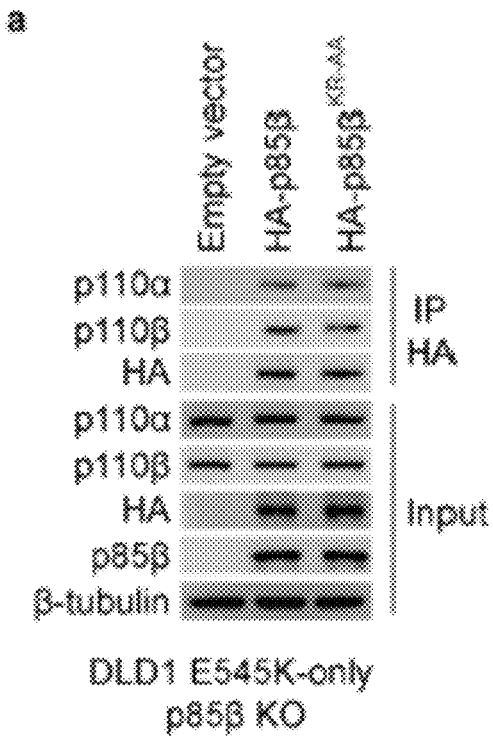
Figure 11B:
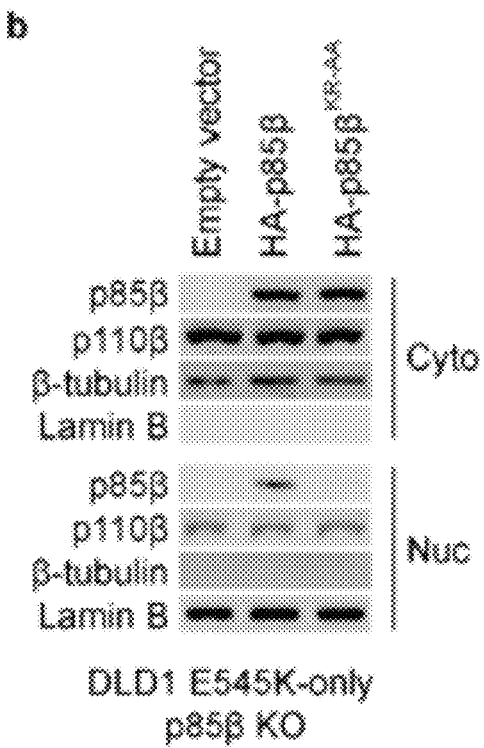
Figure 11C:
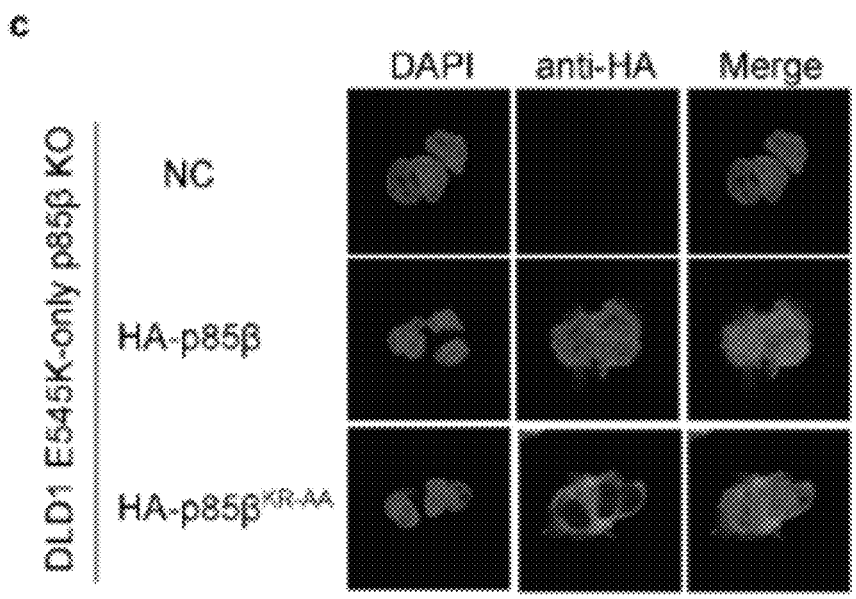
Figure 11D:
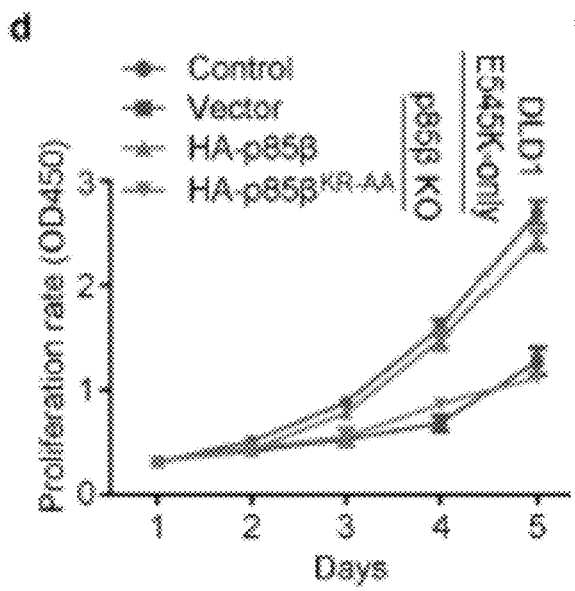
Figure 11E:
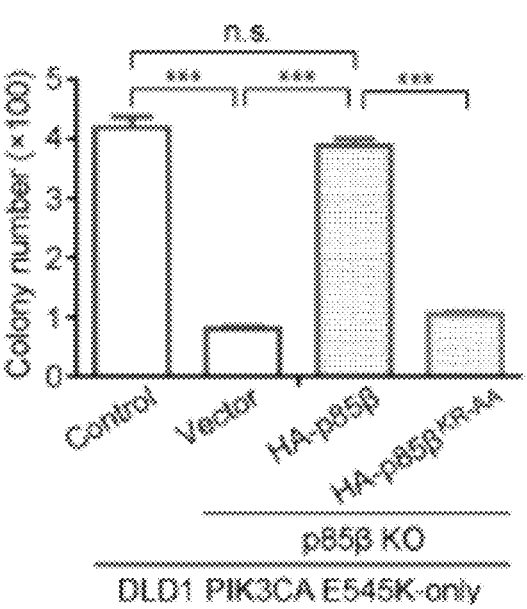
Figure 11F:
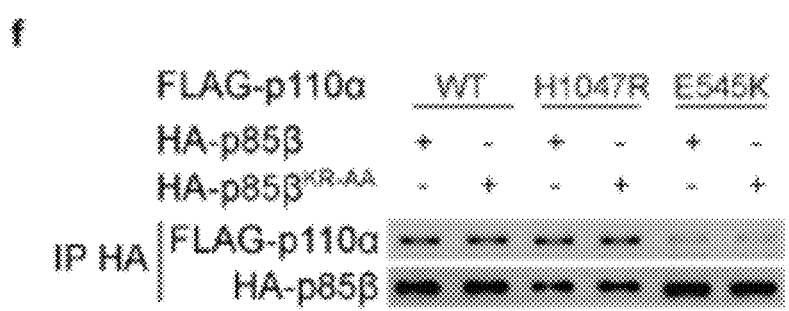

Nuclear Translocation of p85β is Critical for Tumorigenicity of PIK3CA E545K Mutant Cells To determine how p85β translocates into the nucleus, we exploited a nuclear localization sequence (NLS) prediction tool (cNLS Mapper) and identified a putative NLS at amino acids 474 to 484 of p85β (FIG. 4A). To test if this NLS mediates nuclear translocation of p85β, we reconstituted the DLD1 PIK3CA E545K-only p85β KO cells with HA-tagged WT p85β, or mutant p85β construct, in which the two basic amino acids K477 and R478 in the NLS were mutated to alanine (FIG. 11A). Although both the WT and K477A/R478A mutant p85β bound similarly to WT p110α and p110β, immunofluorescent staining and cell fractionation showed that the WT p85β translocated into the nucleus, but the K477A/R478A mutant p85β remained in the cytoplasm (FIGS. 11B & C). Interestingly, reconstitution of the WT, but not the mutant p85β, rescued the defects in cell growth and colony formation of the DLD1 PIK3CA E545K-only p85β KO cells (FIGS. 11D & E). As expected, both WT and the mutant p85β reduced their interactions with p110α E545K mutant protein, but retained the interactions with p110α H1047R mutant protein and p110β (FIGS. 11A &F). To further validate this observation, we generated p85β. K477A/R478A mutant knockin (KI) DLD1 cells using CRISPR/Cas9 mediated gene editing (FIG. 4B). Two independently-derived homozygous KI clones termed p85β$^{KR-AA}$ were chosen for in-depth analyses. The p85β$^{KR-AA}$ mutation did not impact levels of itself, p110α, p110β, and AKT phosphorylation (FIG. 4C), suggesting that the p85β NLS mutant does not affect the kinase activity of PI3K. Nonetheless, the NLS mutant p85β$^{KR-AA}$ failed to translocate into the nucleus (FIG. 4D). Moreover, p850$^{KR-AA}$ mutant KI cell lines displayed reduced cell proliferation, colony formation, and xenograft tumor growth (FIGS. 4E to G). Together, those data suggest that nuclear but not cytoplasmic p85β promotes the growth of cancer cells with a PIK3CA helical domain mutation.

Figure 12A:
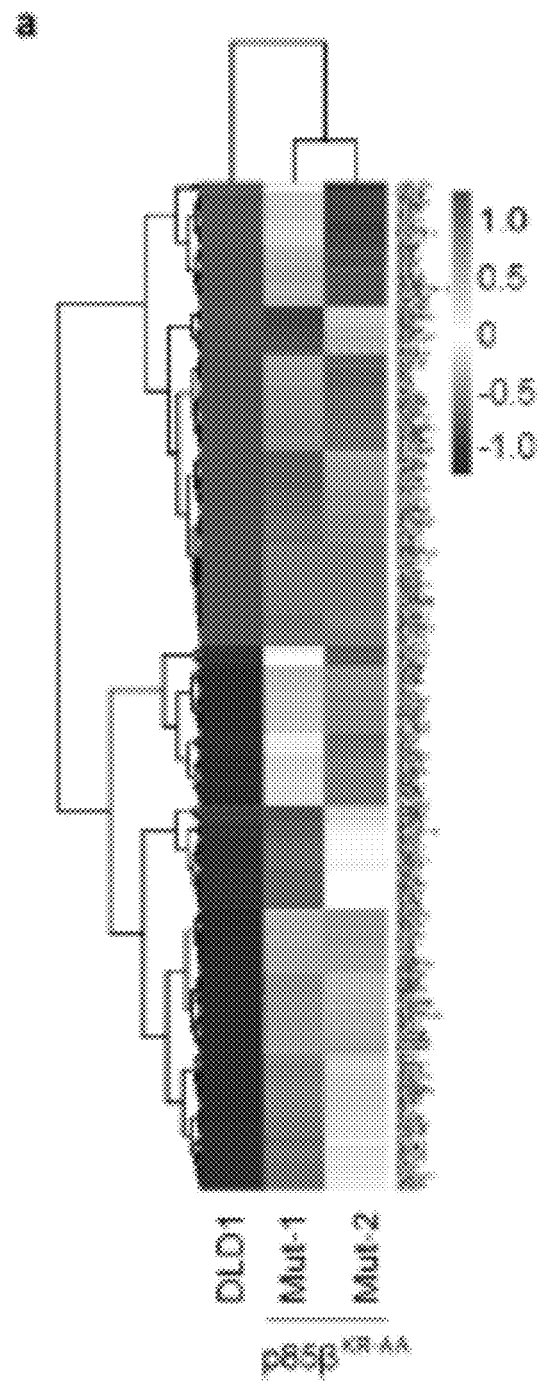
Figure 12B:
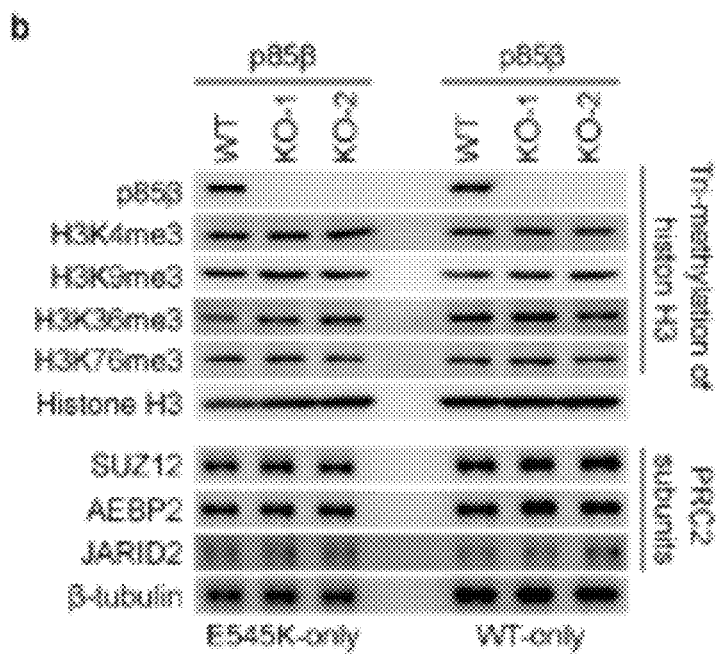

Nuclear p85β Stabilizes EZH1/2 Proteins, Thereby Increasing H3K27 Tri-Methylation We postulated that the p85β present in the nucleus might regulate gene expression. Thus, we performed expression profiling of DLD1 parental cells and the two independently-derived p85β KR-AA mutant clones. Compared with the parental cells, expression levels of 137 genes were up-regulated, and 116 genes were down-regulated in both p85β KR-AA mutant clones (FIG. 12A), suggesting that the nuclear p85β might regulate global gene transcription. We thus examined histone modifications in parental cells and p85β KR-AA mutant clones. As shown in FIG. 5A, levels of histone H3K27 trimethylation (H3K27me3) were reduced in the two p85β KR-AA mutant clones compared to the parental DLD1 cells (FIG. 5A). Consistently, levels of H3K27me3 were higher in DLD1 PIK3CA E545K-only cells than in the isogenic PIK3CA WT-only cells (FIG. 5B). Moreover, knockout of p85β in DLD1 PIK3CA E545K-only cells or knockdown of p85β in MB-361 cells, which harbors a PIK3CA E545K mutation, decreased the levels of H3K27me3 (FIG. 5B). Conversely, the reconstitution of WT p85β, but not p85β KR-AA mutant, in DLD1 PIK3CA E545K-only p85β KO cells restored the levels of H3K27me3 (FIG. 5C). In contrast, the depletion of p85β in DLD1 PIK3CA WT-only cells or T47D (PIK3CA H1047R mutant cells) had no impact on H3K27me3 (FIG. 5B). Furthermore, knockout of p85β did not affect histone trimethylation at other sites, including H3K4, H3K9, H3K36, and H3K76 (FIG. 12B). Taken together, the data suggest that nuclear p85β modulates H3K27me3, a marker for transcriptional repression.

Figure 12C:
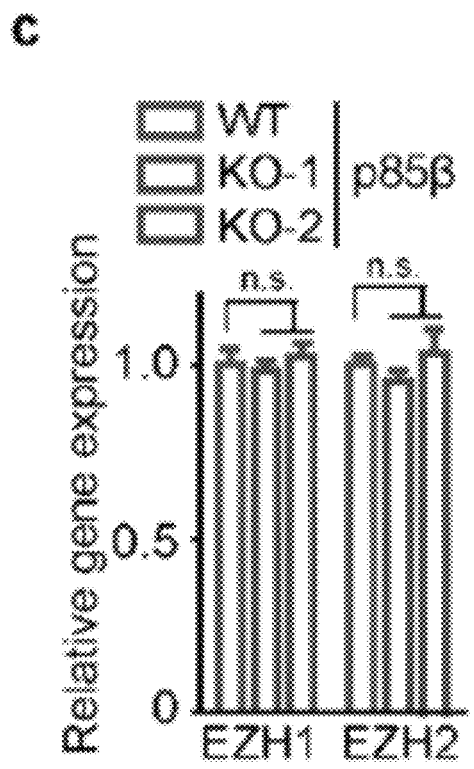
Figure 12D:
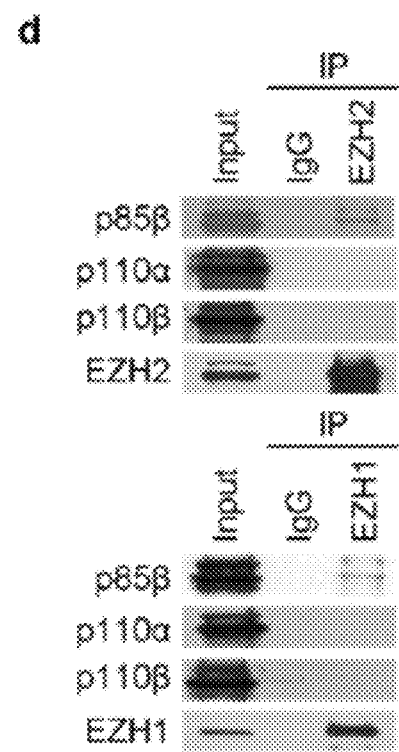

Given that EZH1 and EZH2 are the histone methyltransferases for the H3K27 site, we next examined if nuclear p85β regulates EZH1 and EZH2. As shown in FIG. 5A, compared to parental cells, levels of EZH1 and EZH2 proteins were markedly reduced in p85β KR-AA mutant knockin clones. Consistently, levels of EZH1 and EZH2 proteins were higher in DLD1 PIK3CA E545K-only cells than in the isogenic PIK3CA WT-only cells (FIG. 5B), whereas the depletion of p85β decreased EZH1 and EZH2 protein levels in PIK3CA E545K mutant cells (DLD1 E545K and MB-361), but not in cells with WT PIK3CA or a PIK3CA H1047R mutation (DLD1 PIK3CA WT and T47D) (FIG. 5B). Conversely, the reconstitution of WT p85β, but not p85β KR-AA mutant, in DLD1 PIK3CA E545K-only p85β KO cells restored EZH1 and EZH2 protein levels (FIG. 5C). Moreover, the knockout of p85β reduced EZH 1 and EZH2 protein stability (FIG. 12C). Consistently, the knockout of p85β in DLD1 PIK3CA E545K-only cells did not affect mRNA levels of EZH1 and EZH2 (FIG. 12D). It is worth noting that the knockout of p85β did not impact other components of the PCR2 complex (FIG. 12B). Together, these data suggest that nuclear p85β regulates EZH1 and EZH2 protein stability, thereby enhancing H3K27me3.

Figure 5H:
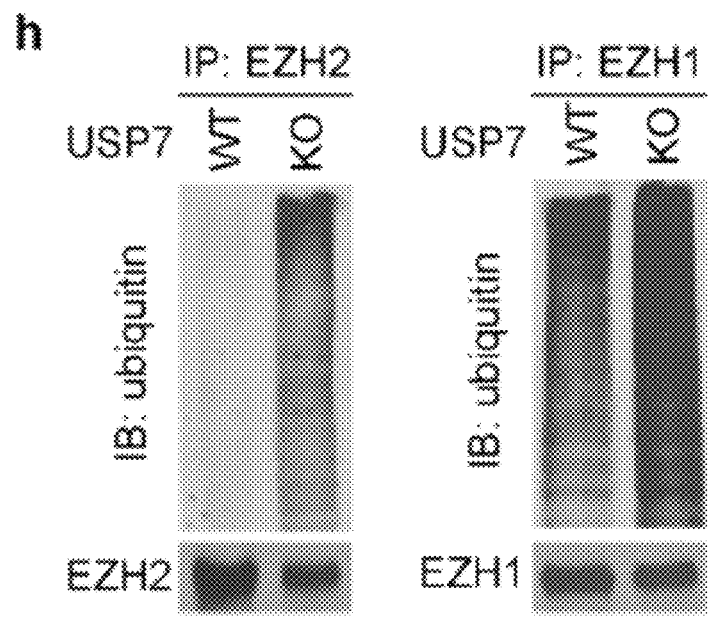
Figure 12E:
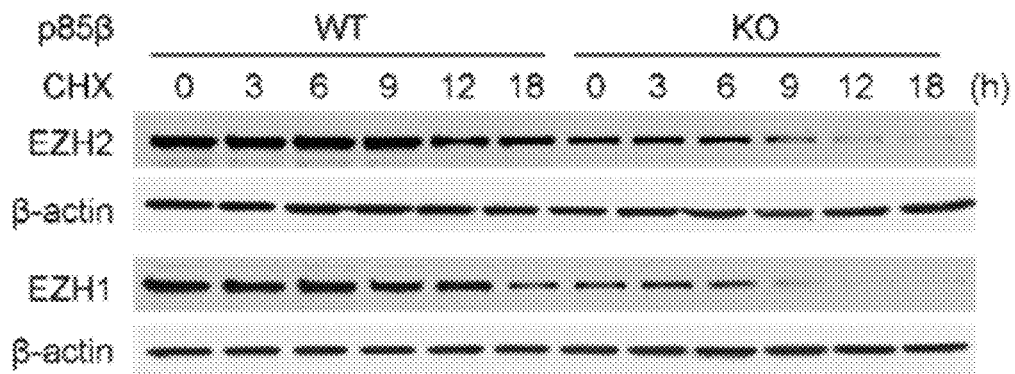
Figure 12F:
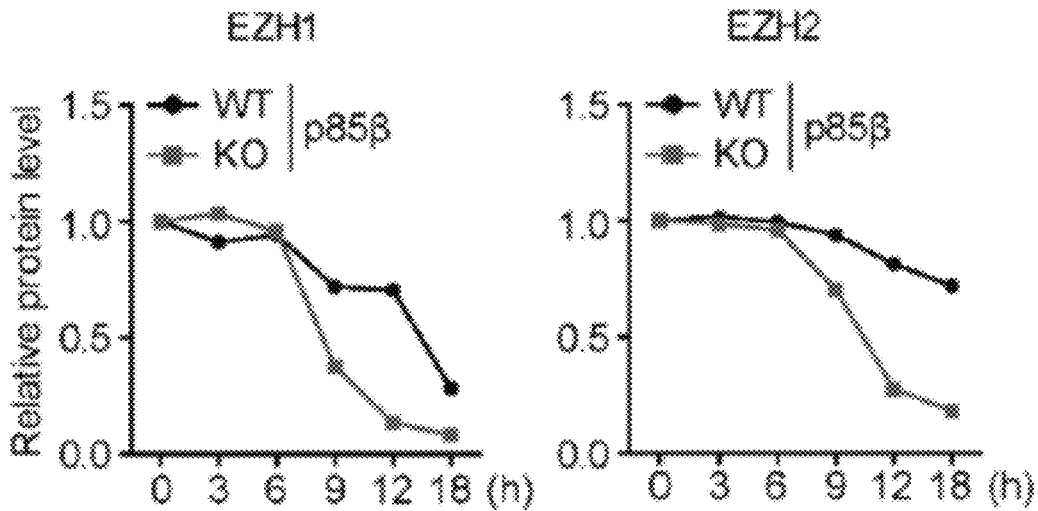
Figure 13A:
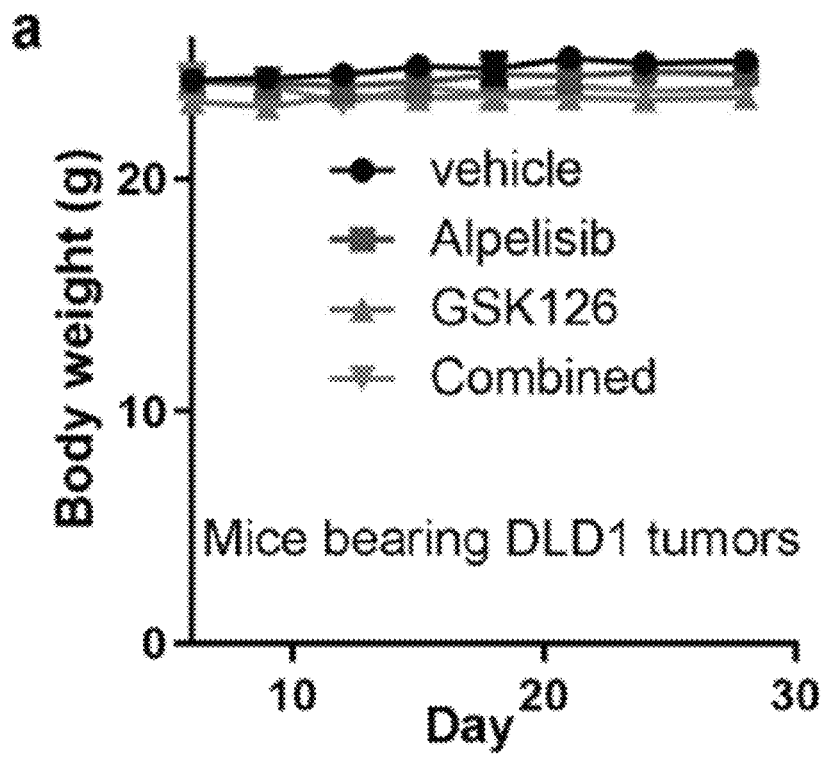
Figure 13B:
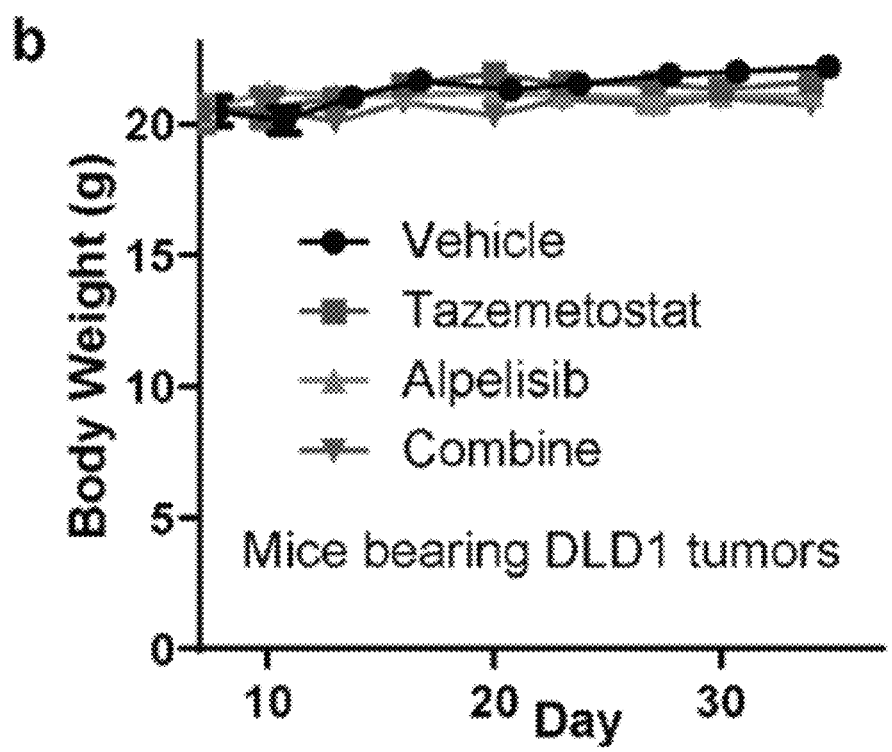
Figure 13C:
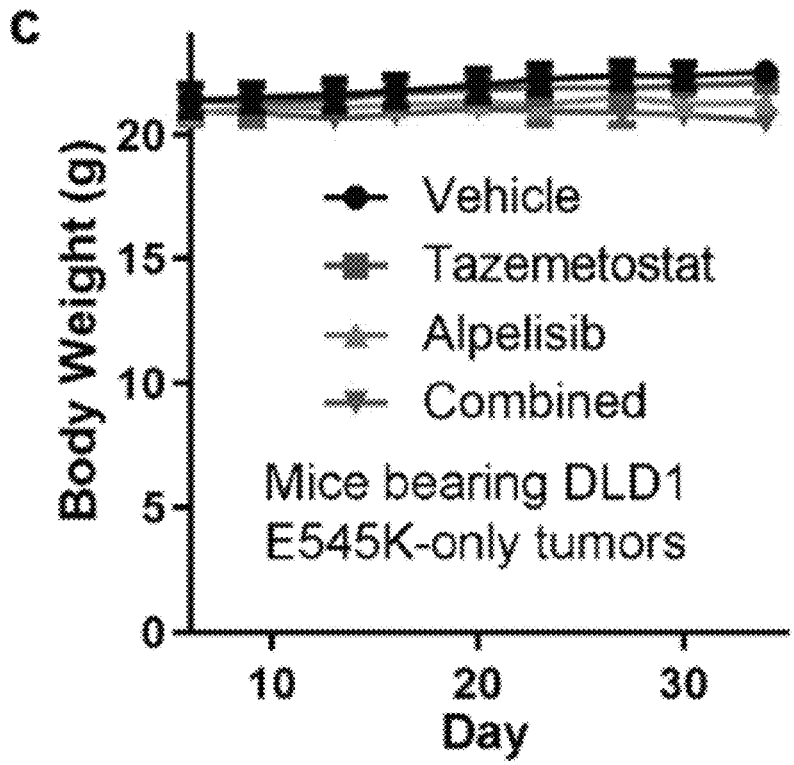
Figure 13D:
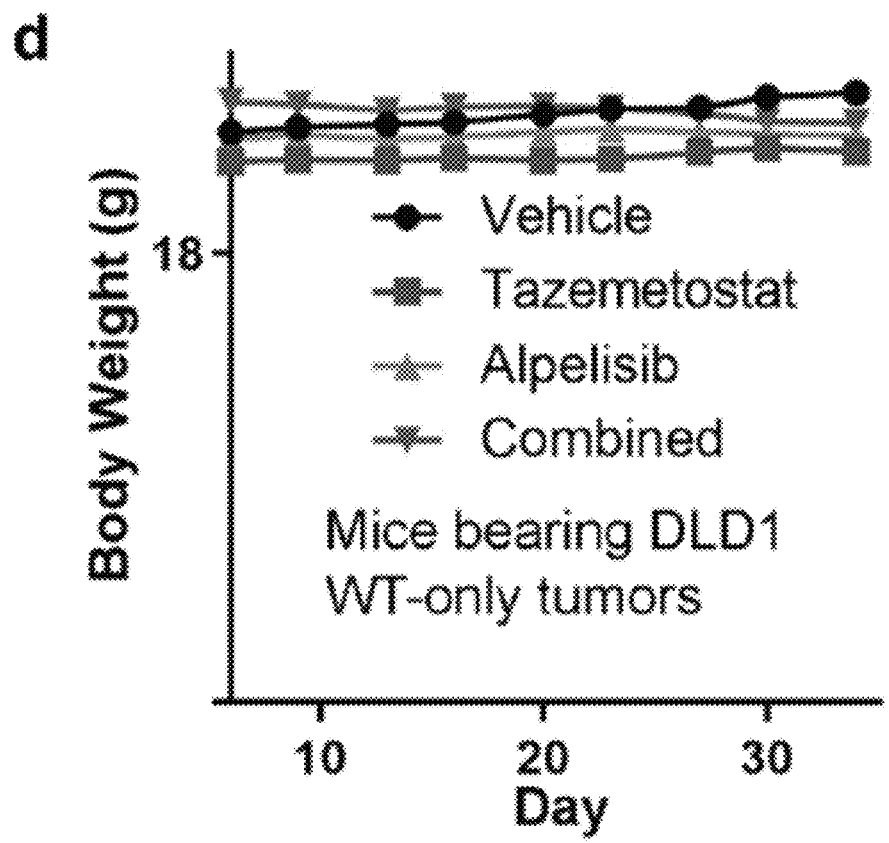
Figure 13E:
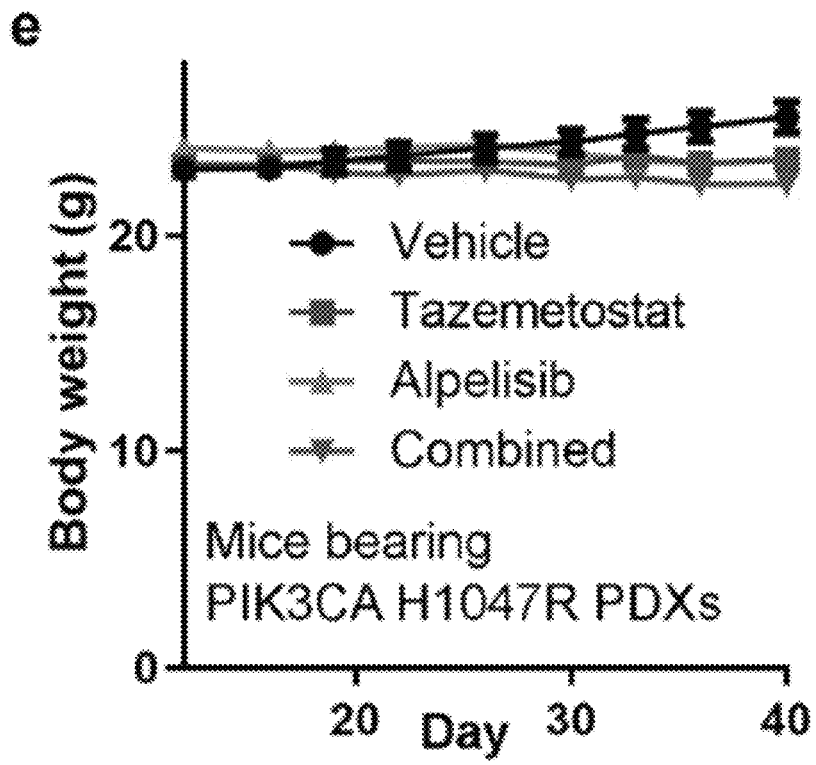
Figure 13F:
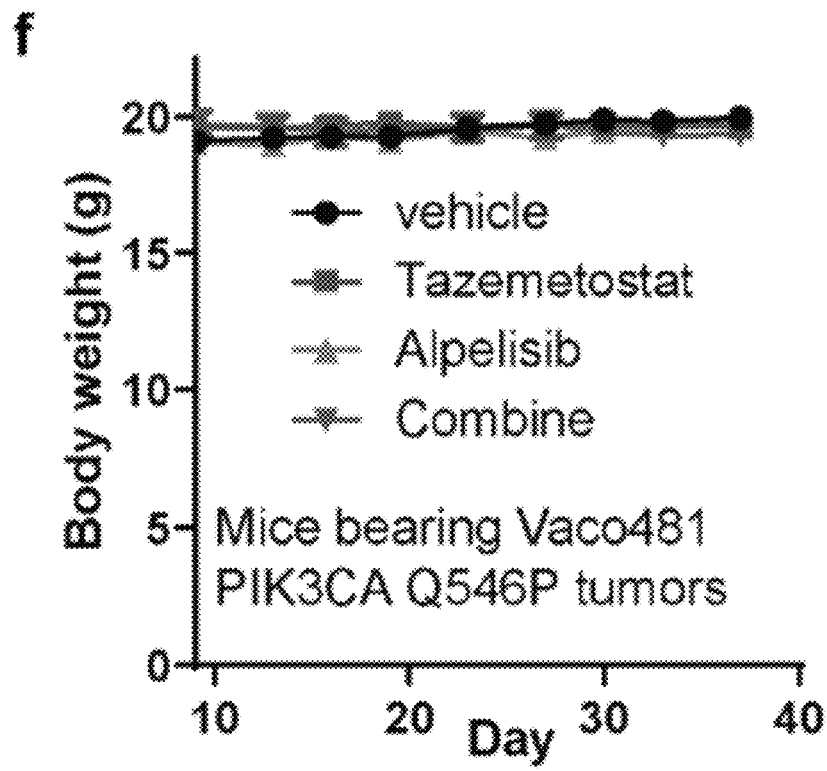
Figure 13G:
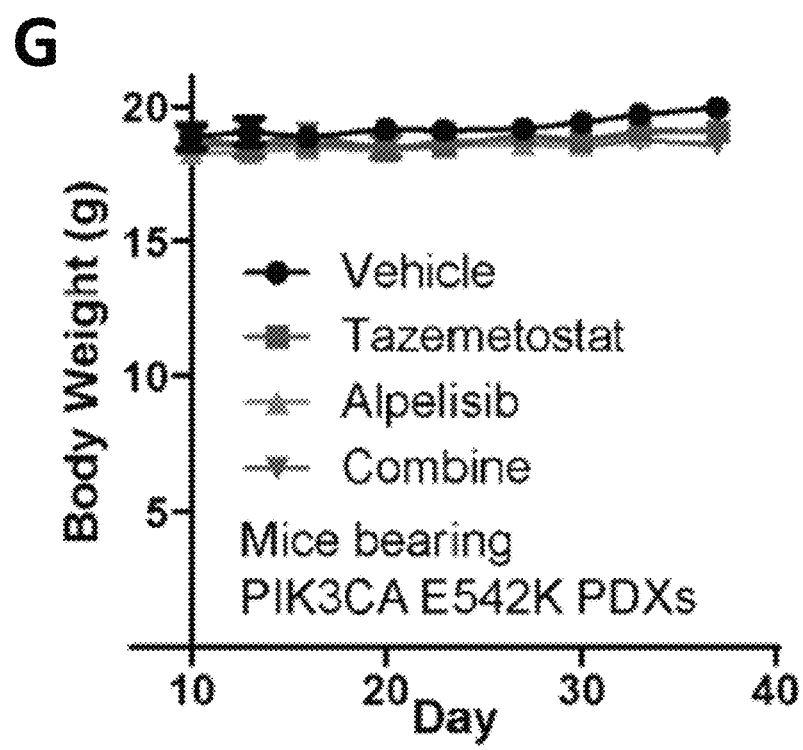
Figure 13H:
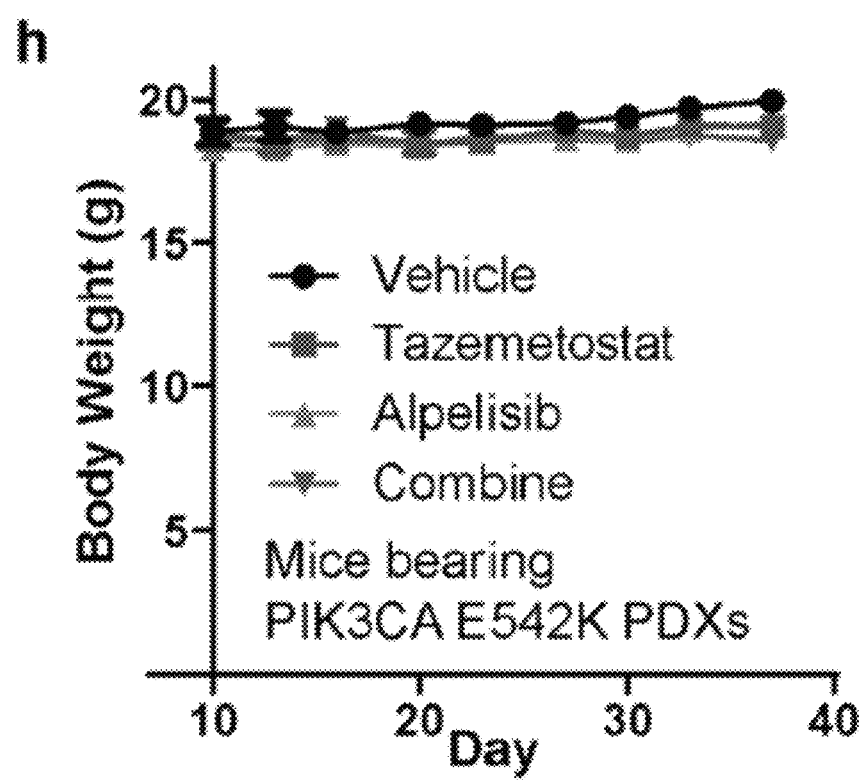

Nuclear p85β Recruits USP7 to EZH1/2 to Protect them from Ubiquitin-Mediated Protein Degradation We next set out to determine how nuclear p85β stabilizes EZH1 and EZH2 proteins. It has been reported that USP7 deubiquitinates and stabilizes EZH2 in prostate cancer cells. We thus postulated that nuclear p85β brings USP7 to EZH1 and EZH2, thereby protecting them from ubiquitin-mediated protein degradation. This notion is supported by the following pieces of evidence: 1) immunoprecipitation analyses showed that p85β interacted with USP7, EZH1, and EZH2 in DLD1 cells, which harbor a PIK3CA E545K mutation (FIG. 5D); 2) more USP7 bound to EZH1 or EZH2 in DLD1 PIK3CA E545K-only cells than in the isogenic p85β KO cells (FIG. 5E); 3) EZH1 and EZH2 protein levels were reduced in DLD1 USP7 KO cells that we generated previously, compared to the parental cells (FIG. 5F); 4) proteasome inhibitor MG132 treatment restored EZH1 and EZH2 protein levels in USP7 KO cells (FIG. 5G); and 5) EZH1 and EZH2 ubiquitination levels were increased in USP7 KO cells compared to the parental cells (FIG. 5H). Moreover, the stabilization of EZH1 and EZH2 by the nuclear p85β seems not to involve the p110α or p110β catalytic subunits, because EZH1 and EZH2 bound to p85β, but not p110α and p110β (FIG. 12E). Taken together, the data suggest that nuclear p85β recruits USP7 to stabilize EZH1/2, thereby enhancing H3K27 trimethylation.

Figure 6A:
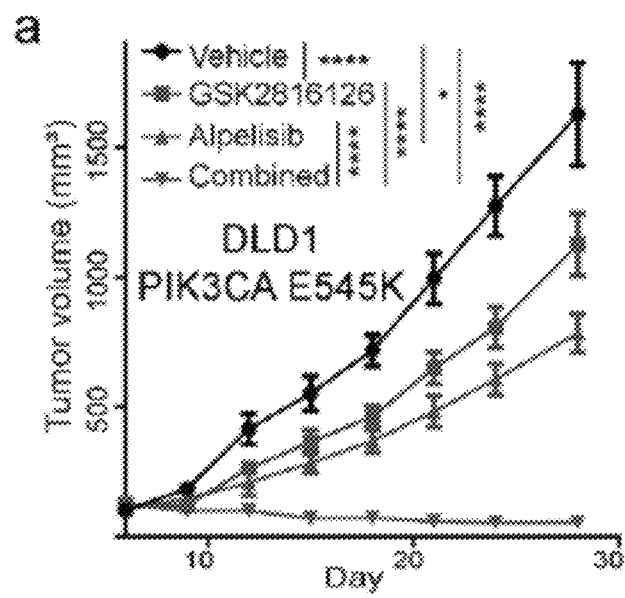
Figure 6B:
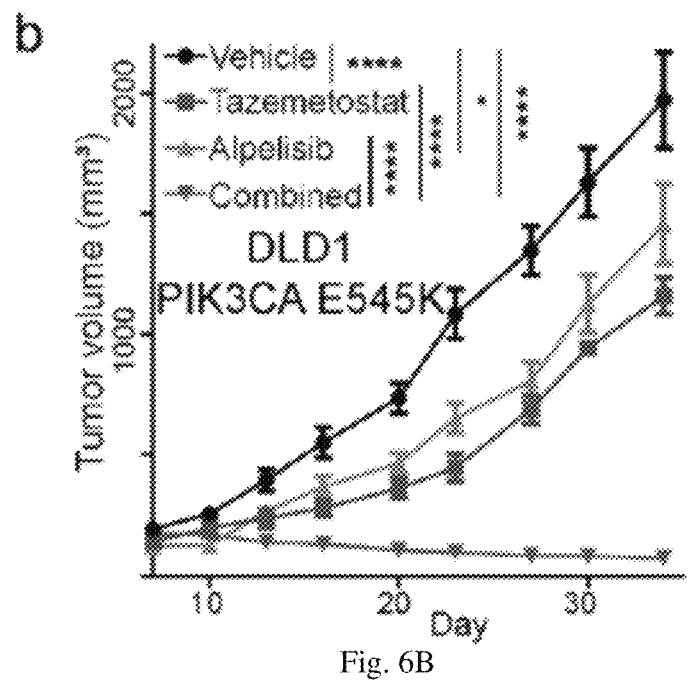
Figure 6C:
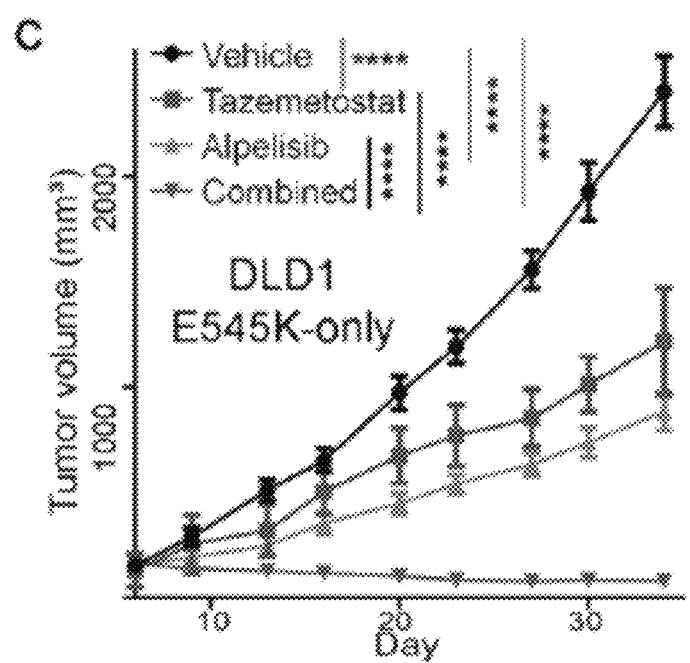
Figure 6D:
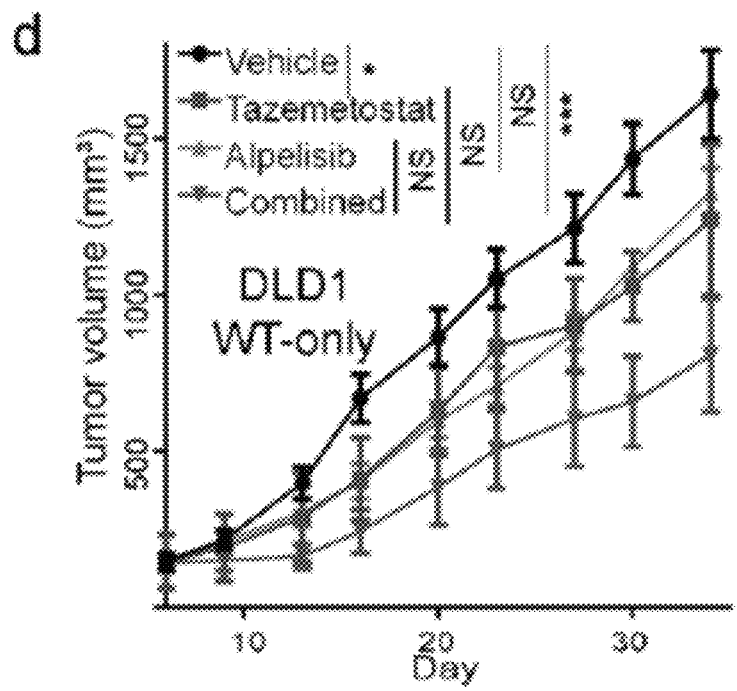
Figure 6E:
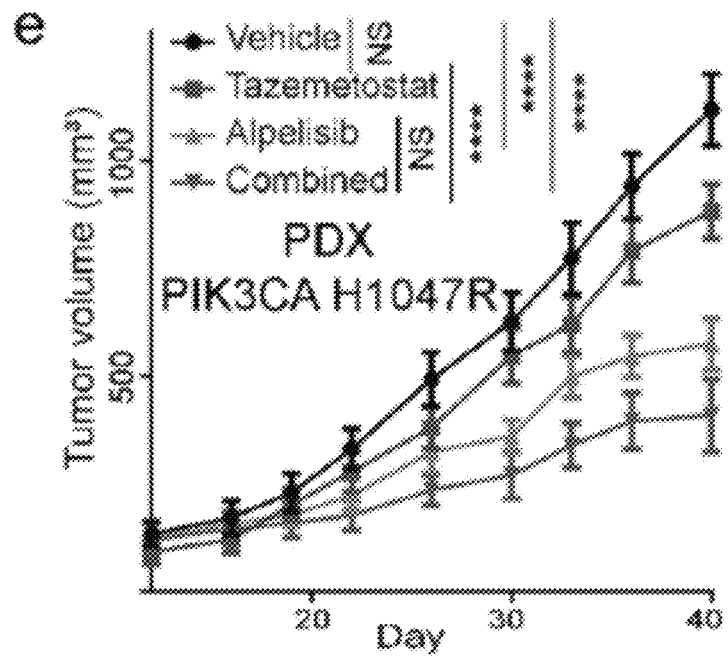
Figure 6F:
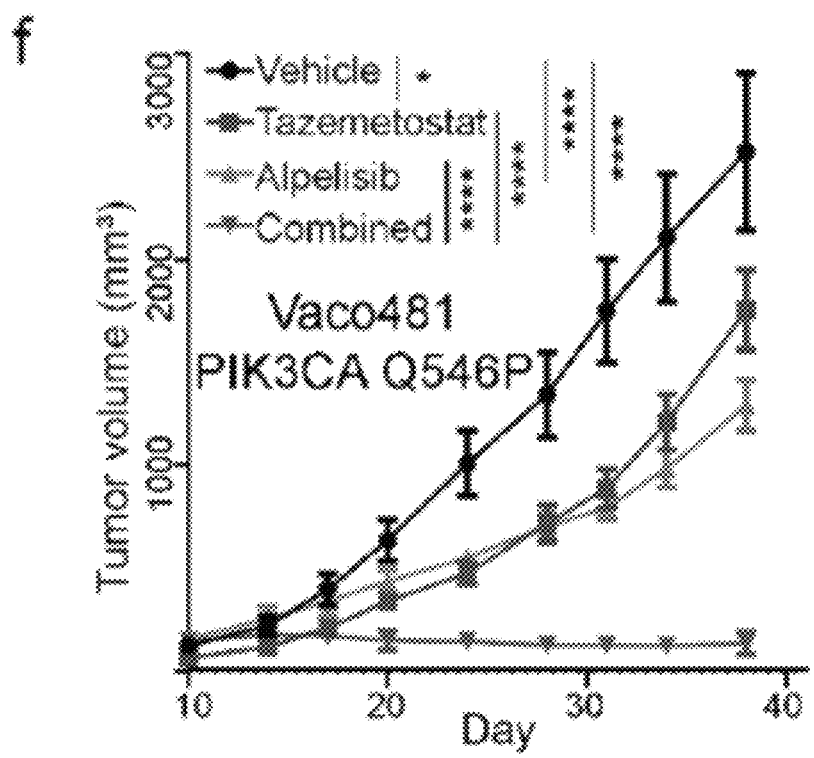
Figure 6G:
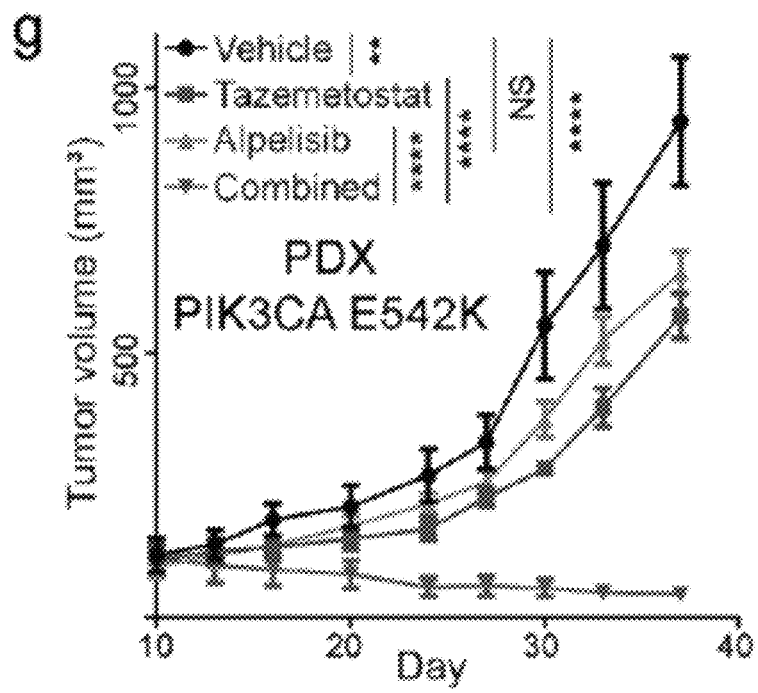
Figure 6H:
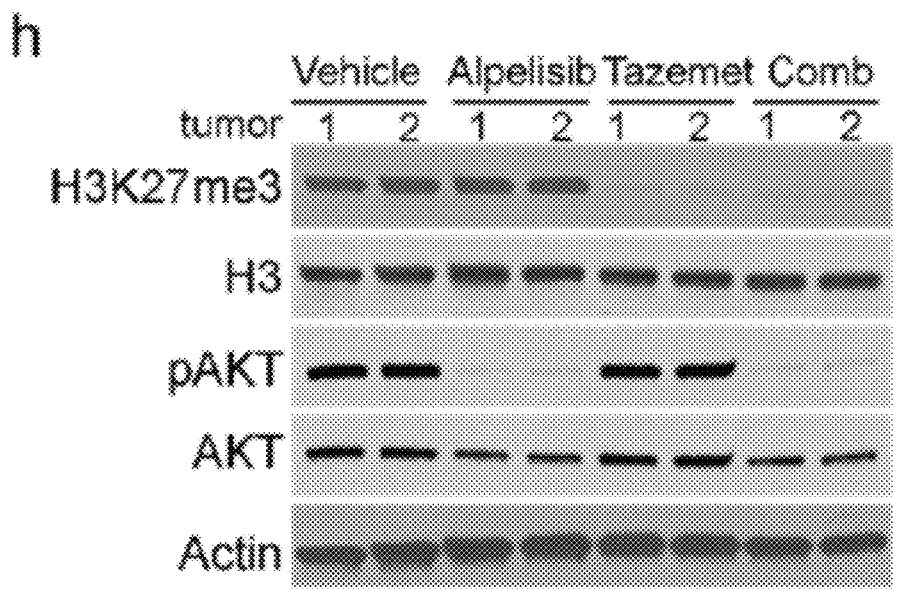

A Combination of an EZH Inhibitor and the p110α Inhibitor Alpelisib Induces Tumor Repression We have shown that the nuclear p85β stabilizes EZH1 and EZH2 in cancer cells with a PIK3CA E545K mutation. Given that the mutation also activates p110α kinase activity, we hypothesized that a combination of an EZH inhibitor and a p110α inhibitor would have a better tumor inhibitory effect than either alone. We first tested a combination of p110α inhibitor Alpelisib (BYL-719) with an EZH inhibitor, GSK2816126. As shown in FIG. 6A, the drug combination induced tumor regression of xenografts established from DLD1 cells, which harbor a PIK3CA E545K mutation, whereas single drugs alone only slowed tumor growth (FIG. 6A). Similar results were obtained with a combination of Alpelisib with another EZH2 inhibitor Tazemetostat (FIG. 6B). We chose Tazemetostat for in-depth studies, because it was recently approved by the FDA to treat EZH2 mutant follicular lymphoma and advanced epithelioid sarcoma. Our hypothesis predicts that tumors that harbor a PIK3CA helical domain mutation are more sensitive to the drug combination than tumors with WT PIK3CA. To test this notion, we treated tumors established from either PIK3CA E545K-only or PIK3CA WT-only cells. The combination of Alpelisib and Tazemetostat induced regression of tumors established with PIK3CA E545K-only (FIG. 6C), whereas the drug combination only slowed down the growth of the PIK3CA WT-only tumors (FIG. 6D). Moreover, the drug combination did not induce tumor regression of a CRC patient-derived xenograft (PDX) harboring a PIK3CA H1047R kinase domain mutation (FIG. 6E). As shown in FIG. 2, the PIK3CA helical domain mutations occurred in three residues (E545, E542, and Q546). Since we had demonstrated that the combination of Alpelisib and Tazemetostat induced tumor regression of PIK3CA E545K mutant tumors, we next tested if the drug combination induced regression of tumors harboring the other two recurrent PIK3CA helical domain mutations (E542K and Q546P). As shown in FIGS. 6F and G, the combination of Alpelisib and Tazemetostat induced tumor regression of Vaco481 CRC cells with a PIK3CA Q546P mutation and a CRC PDX harboring a PIK3CA E542K mutation. As expected, compared to PIK3CA E542K mutant PDXs treated with vehicle control, Alpelisib reduced pAKT levels only, Tazemetostat reduced H3K27me3 only, whereas the drug combination decrease levels of both pAKT and H3K27me3 (FIG. 6H). It is worth noting the drug combination was well-tolerated as the body weights of mice were maintained during the course of the drug treatments (FIGS. 13A to H). These results suggest that the combination of Tezametostat and Alpelisib could be an effective treatment for cancers harboring PIK3CA helical domain mutations.

This Example describes a previously unrecognized mechanism by which PIK3CA helical domain mutations exert oncogenic signaling: p85β, but not p85α, dissociates from the p110α helical domain mutant protein and translocates into the nucleus. The nuclear p85β stabilizes EZH1/2 by recruiting deubiquitinase USP7 to the two proteins and enhancing H3K27 trimethylation. Additionally, our previous study demonstrated that the p110α helical domain mutant proteins directly bind to IRS1 and activate the canonical PDK1-AKT signaling pathways. Therefore, PIK3CA helical domain mutations promote oncogenesis through two independent pathways: a canonical p110-PDK1-AKT pathway and a nuclear p85β-USP7-EZH1/2 axis (FIG. 7). Moreover, our data suggest that targeting both pathways with Alpelisib and Tazemetostat could be an effective therapeutic approach for PIK3CA helical domain mutant cancers.

Firstly, this Example sheds new light on the nuclear translocation and function of p85β. We identified an NLS in p85β that plays a major role in its nuclear translocation. When we mutated the critical basic amino acids KR to AA in both ectopically expressed and endogenous p85β, the mutant p85β protein fail to translocate into the nucleus (FIGS. 4 and 11). However, the p85β NLS is not sufficient to induce nuclear translocation, as our data showed that p85β translocates into the nucleus in the PIK3CA helical domain mutant cell lines, but not in the WT and PIK3CA kinase domain mutant cell lines (FIG. 3). We postulate that the release of p85β from the PI3K complexes and exposure of the NLS in the iSH2 domain trigger p85β nuclear translocation. Although BRD7 has been reported to act as a chaperone for nuclear transport of p85α and p85β, our data suggest that BRD7 is not the major mediator of p85β nuclear translocation in PIK3CA helical domain mutant cancer cells, because knockout of BRD7 only had a marginal effect on nuclear p85β levels. It is interesting that p85β, but not p85α, dissociates from the p110α helical domain mutant proteins. Our domain-swapping experiment shows that the N-terminal p85β sequences cause its dissociation from the p110α helical domain mutant proteins (FIGS. 1I & J). Although p85α also has a putative NLS sequence, it still tightly binds to p110α helical mutant protein, which prevents it from the NLS-mediated nuclear translocation.

Secondly, our data suggest that the nuclear p85β plays an oncogenic role in tumors. Nuclear p85β has been shown to interact with XBP1 to modulate endoplasmic reticulum stress or binds to BRD7 and XBP1 to regulate glucose homeostasis. Although it has been proposed that overexpression of p85β in some tumor types promotes cancer progression through the canonical PI3K enzymatic activity, none of the previous studies have implicated nuclear p85β in tumorigenesis. Here, we provide several lines of evidence implicating an oncogenic role of nuclear p85β in PIK3CA helical domain mutant cancers: (1) knockout of p85β reduces xenograft tumor growth of DLD1 PIK3CA E545K cells, but not the isogenic PIK3CA WT cells; (2) knockdown of p85β reduces the growth of a panel of PIK3CA helical domain mutant cell lines, not a panel of PIK3CA kinase domain mutant cell lines; (3) the p85β NLS mutant DLD1 knockin cells, lacking nuclear translocation of p85β, have reduced xenograft tumor growth.

Thirdly, our data suggest that the nuclear p85β stabilizes EZH1 and EZH2 by recruiting deubiquitinase USP7, and enhances H3K27 trimethylation, thereby promoting the growth of PIK3CA helical domain mutant tumors. Consistently, an oncogenic role of EZH1/2, especially EZH2, has been well-documented because recurrent gain-of-function EZH2 mutations have been identified in 22% of diffuse large-cell B cell lymphomas and ~10% of follicular lymphomas. Interestingly, the aforementioned oncogenic nuclear p85β function seems to be independent of p110α and p110β, because our data demonstrated that EZH1 and EZH2 bind to p85β, but not p110α and p110β (FIG. 12E).

Lastly, our data suggest that simultaneously targeting nuclear p85β-stabilized EZHs and p110α could be an effective cancer treatment. The p110α specific inhibitor Alpelisib in combination with Fulvestrant has been approved by the FDA for the treatment of HR-positive and HER2-negative breast cancers with PIK3CA mutation. However, the efficacy of Alpelisib in other tumor types (such as colorectal cancer) has been disappointing. Moreover, in some early clinical trials, patients with PIK3CA helical domain mutations are more resistant to Alpelisib than those with PIK3CA kinase domain mutations. Thus, novel approaches are needed to target the PIK3CA helical domain mutations. Our data demonstrated that the combination of Alplelisb and EZH2 inhibitor Tazmetostat induced regression of tumors harboring each of the three recurrent PIK3CA helical domain mutations, but not tumors with PIK3CA WT or a kinase domain mutation. The molecular mechanisms we uncovered here apply not only to CRC but to other types of tumor types with a PIK3CA helical domain mutation as well.

TABLE 1

| REAGENT or RESOURCE | SOURCE | IDENTIFIER |
|---|---|---|
| Antibodies | | |
| Mouse monoclonal antibody anti-FLAG | Sigma-Aldrich | Cat# F1804, RRID: AB_262044 |
| Mouse monoclonal antibody anti-Myc | Santa Cruz | Cat# sc-40, RRID: AB_627268 |
| Mouse polyclonal antibody anti-HA | Santa Cruz | Cat# sc-805, RRID: AB_631618 |
| Rabbit monoclonal antibody anti-p110 alpha | Cell Signaling Technology | Cat# 4249, RRID: AB_2165248 |
| Rabbit monoclonal antibody anti-p110 beta | Cell Signaling Technology | Cat# 3011, RRID: AB_2165246 |
| Rabbit monoclonal antibody anti-p85 alpha | Abcam | Cat# ab191606 |
| Rabbit monoclonal antibody anti-p85 alpha pY607 | Abcam | Cat# ab182651, RRID: AB_2756407 |
| Rabbit monoclonal antibody anti-p85 beta | Abcam | Cat# ab180967 |
| Rabbit monoclonal antibody anti-p85 beta pY464 | Abcam | Cat# ab138364 |
| Mouse monoclonal antibody anti-P-Tyr-100 | Cell Signaling Technology | Cat# 9411, RRID: AB_331228 |
| Rabbit polyclonal antibody anti-IRS1 | Proteintech | Cat# 17509-1-AP, RRID: AB_10596914 |
| Rabbit polyclonal antibody anti-EGFR | Proteintech | Cat# 18986-1-AP, RRID: AB_10596476 |
| Rabbit polyclonal antibody anti-BRD7 | Proteintech | Cat# 51009-2-AP, RRID: AB_2259226 |
| Rabbit polyclonal antibody anti-β-tubulin | Bioss | Cat# bs-4511R, RRID: AB_11114300 |
| Rabbit monoclonal antibody anti-Lamin B | Bioss | Cat# bsm-33010M |
| Rabbit monoclonal antibody anti-AKT pT308 | Cell Signaling Technology | Cat# 13038, RRID: AB_2629447 |
| Rabbit monoclonal antibody anti-AKT pS473 | Cell Signaling Technology | Cat# 4060, RRID: AB_2315049 |
| Rabbit monoclonal antibody anti-AKT | Cell Signaling Technology | Cat# 9272, RRID: AB_329827 |
| Rabbit polyclonal antibody anti-GSK-3β pS9 | Cell Signaling Technology | Cat# 9336, RRID: AB_331405 |
| Rabbit monoclonal antibody anti-GSK-3β | Cell Signaling Technology | Cat# 9315, RRID: AB_490890 |
| Rabbit monoclonal antibody anti-FoxO1 pT24 | Cell Signaling Technology | Cat# 9464, RRID: AB_329842 |
| Mouse monoclonal antibody anti-FoxO1 | Millipore | Cat# 3012276 |

TABLE 1-continued

| REAGENT or RESOURCE | SOURCE | IDENTIFIER |
| --- | --- | --- |
| Rabbit monoclonal antibody anti-mTOR pS2448 | Cell Signaling Technology | Cat# 5536, RRID: AB_10691552 |
| Rabbit monoclonal antibody anti-mTOR | Cell Signaling Technology | Cat# 2983, RRID: AB_2105622 |
| Rabbit monoclonal antibody anti-p70 S6 kinase pS371 | Cell Signaling Technology | Cat# 9208, RRID: AB_330990 |
| Rabbit monoclonal antibody anti-anti-p70 S6 kinase | Cell Signaling Technology | Cat# 2708, RRID: AB_390722 |
| Rabbit monoclonal antibody anti-Erk1/2 pT202, pT204 | Cell Signaling Technology | Cat# 4370, RRID: AB_2315112 |
| Rabbit monoclonal antibody anti-Erk1/2 | Cell Signaling Technology | Cat# 4695, RRID: AB_390779 |
| Rabbit polyclonal antibody anti-DIRAS2 | Proteintech | Cat# 15557-1-AP, RRID: AB_2261563 |
| Rabbit monoclonal antibody anti-H3K4me3 | Cell Signaling Technology | Cat# 9783, Tri-Methyl Histone H3 Antibody Sampler Kit |
| Rabbit monoclonal antibody anti-H3K9me3 | Cell Signaling Technology | Cat# 9783, Tri-Methyl Histone H3 Antibody Sampler Kit |
| Rabbit monoclonal antibody anti-H3K27me3 | Cell Signaling Technology | Cat# 9783, Tri-Methyl Histone H3 Antibody Sampler Kit |
| Rabbit monoclonal antibody anti-H3K36me3 | Cell Signaling Technology | Cat# 9783, Tri-Methyl Histone H3 Antibody Sampler Kit |
| Rabbit monoclonal antibody anti-H3K79me3 | Cell Signaling Technology | Cat# 9783, Tri-Methyl Histone H3 Antibody Sampler Kit |
| Rabbit monoclonal antibody anti-H3 | Cell Signaling Technology | Cat# 9783, Tri-Methyl Histone H3 Antibody Sampler Kit |
| Rabbit monoclonal antibody anti-EZH1 | Cell Signaling Technology | Cat# 62083, PRC2 Antibody Sampler Kit |
| Rabbit monoclonal antibody anti-EZH2 | Cell Signaling Technology | Cat# 62083, PRC2 Antibody Sampler Kit |
| Rabbit monoclonal antibody anti-SUZ12 | Cell Signaling Technology | Cat# 62083, PRC2 Antibody Sampler Kit |
| Rabbit monoclonal antibody anti-EED | Cell Signaling Technology | Cat# 62083, PRC2 Antibody Sampler Kit |
| Rabbit monoclonal antibody anti-JARID2 | Cell Signaling Technology | Cat# 62083, PRC2 Antibody Sampler Kit |
| Rabbit monoclonal antibody anti-AEBP2 | Cell Signaling Technology | Cat# 62083, PRC2 Antibody Sampler Kit |
| USP7 antibody | Cell Signaling Technology | Cat# 4833, RRID: AB_10557113 |
| Rabbit polyclonal antibody anti-KPNA1 | Proteintech | Cat# 18137-1-AP, RRID: AB_2133553 |
| Rabbit monoclonal antibody anti-Ki67 | Abcam | Cat# ab92742, RRID: AB_10562976 |
| Rabbit polyclonal antibody anti-IgG | Cell Signaling Technology | Cat# 2729, RRID: AB_1031062 |
| Chemicals and reagents | | |
| Anti-Flag Affinity Gel | Bimake | Cat# B23101 |
| Anti-Myc tag Mouse mAb conjugated Agarose Beads | Engibody Biotechnology | Cat# AT0080 |
| Anti-HA tag Mouse mAb conjugated Agarose Beads | Engibody Biotechnology | Cat# AT0079 |
| EGF | Sigma-Aldrich | Cat# E5036 |
| Insulin | Sigma-Aldrich | Cat# I2643 |
| Alpelisib | Selleck Chemicals | Cat# S2814 |
| Importazole | CSNpharm | Cat# CSN19098 |
| LY294002 | CSNpharm | Cat# CSN11346 |
| GSK126 (EZH1/2 Inhibitor) | Selleck Chemicals | Cat# S7061 |
| DAPI | Sigma-Aldrich | Cat# D9542 |
| Critical Commercial Assays | | |
| USER cloning system | NEB | Cat# #M5505L |
| Site-Directed Mutagenesis Kit | Agilent | Cat# 200523 |
| EnVision-HRP kit | Dako | Cat# K4001 |
| PrimeScript RT Reagent Kit | TAKARA | Cat# RR037A |
| Dual-Luciferase Reporter Assay System | Promega | Cat# E1910 |
| ChIP assay kit | Beyotime | Cat# P2078 |
| Mycoplasma Detection Kit | Yeasen | Cat# 40601ES20 |
| Experimental Models: Cell Lines | | |
| Human: 293T | ATCC | Cat# CRL-1573 |
| Human: DLD1 | ATCC | Cat# CCL-221 |
| Human: DLD1 PIK3CA E545K-only | Gift | Dr. Bert Vogelstein |

TABLE 1-continued

| REAGENT or RESOURCE | SOURCE | IDENTIFIER |
|---|---|---|
| Human: DLD1 PIK3CA WT-only | Gift | Dr. Bert Vogelstein |
| Human: DLD1 Kras G13D-only | Gift | Dr. Bert Vogelstein |
| Human: DLD1 Kras WT-only | Gift | Dr. Bert Vogelstein |
| Human: HCT116 | ATCC | Cat# CCL-247 |
| Human: SW480 | ATCC | Cat# CCL-228 |
| Human: LOVO | ATCC | Cat# CCL-229 |
| Human: RKO | ATCC | Cat# CRL-2577 |
| Human: SW948 | ATCC | Cat# CCL-237 |
| Human: T47D | ATCC | Cat# CRL-3436 |
| Human: MDA-MB-361 | ATCC | Cat# HTB-27 |
| Human: H460 | ATCC | Cat# HTB177 |
| Experimental Models: Organisms/Strains | | |
| Mouse: BALB/c nude | The Jackson Laboratory | Stock No: 002019 |
| Mouse: BALB/c nude | Experimental Animal Research Center of Shanghai Cancer Institute | N/A |
| Recombinant DNA | | |
| pCMV FLAG-p110α WT | Hao et al., 2013 | N/A |
| pCMV FLAG-p110α R88Q | Hao et al., 2013 | N/A |
| pCMV FLAG-p110α K111N | Hao et al., 2013 | N/A |
| pCMV FLAG-p110α N345K | Hao et al., 2013 | N/A |
| pCMV FLAG-p110α C420R | Hao et al., 2013 | N/A |
| pCMV FLAG-p110α E542K | Hao et al., 2013 | N/A |
| pCMV FLAG-p110α E545K | Hao et al., 2013 | N/A |
| pCMV FLAG-p110α Q546K | Hao et al., 2013 | N/A |
| pCMV FLAG-p110α M1043I | Hao et al., 2013 | N/A |
| pCMV FLAG-p110α H1047L | Hao et al., 2013 | N/A |
| pCMV FLAG-p110α G1049R | Hao et al., 2013 | N/A |
| pCMV HA-p85α WT | This paper | N/A |
| pCMV HA-p85β WT | This paper | N/A |
| pCMV HA-p85β Y449F, Y453F | This paper | N/A |
| pCMV HA-p85β Y460F, Y464F, Y467F | This paper | N/A |
| pCMV HA-p85β Y605F | This paper | N/A |
| pCMV HA-p85β Y655F | This paper | N/A |
| pCMV HA-p85β Y671F | This paper | N/A |
| pCMV HA-p85β KR477, 478AA | This paper | N/A |
| AAV-neo-PIK3R2 KR477, 478AA | This paper | N/A |
| pGL3-DIRAS2 3 kb | This paper | N/A |
| pGL3-DIRAS2 2 kb | This paper | N/A |
| pGL3-DIRAS2 1 kb | This paper | N/A |
| pGL3-DIRAS2 0.5 kb | This paper | N/A |
| pGL3-SOWAHB 3 kb | This paper | N/A |
| pGL3-SOWAHB 2 kb | This paper | N/A |
| pGL3-SOWAHB 1 kb | This paper | N/A |
| pGL3-SOWAHB 0.5 kb | This paper | N/A |
| pCMV MYC-KPNA1 WT | This paper | N/A |
| pCMV MYC-KPNA2 WT | This paper | N/A |
| Software and Algorithms | | |
| CRISPR design tool | IDT design tool | https://sg.idtdna.com/pages/ |
| TCGA data source | TCGA Hub | https://xenabrowser.net/datapages/ |

Example 2

Combination of Tazemetostat and Alpelisib Induces Tumor Regression of PIK3CA Helical Domain Mutant Cancer We have demonstrated that the combination of EZH inhibitor GSK126 and p110α inhibitor Alpelisib induced tumor regression of xenografts for DLD1 colorectal cancer cells, which harbor a PIK3CA E545K helical domain mutation. Tazemetostat, another EZH inhibitor, has been recently approved by the FDA to treat epithelioid sarcomas and EZH2 mutant follicular lymphomas. In this example, we set out to test if a combination of Tazemetostat and Alpelisib also induces tumor regression of DLD1 xenografts. As show in the FIG. 14(A-B) below, the combination of Tazemetostat and Alpelisib indeed induced tumor regression of DLD1 xenografts, whereas either single drug alone only slowed down tumor growth.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:
1. A method of treating PIK3CA helical domain mutant cancer in a subject in need thereof, the method comprising:
administering to the subject therapeutically effective amounts of (i) an EZH inhibitor in combination with (ii) Alpelisib, wherein the EZH inhibitor is tazemetostat (EPZ-6438, CAS No. 1403254-99-8) or GSK126 (GSK2816126, CAS No. 1346574-57-9).

2. The method of claim 1, wherein the PIK3CA helical domain mutant cancer includes a mutation in the p110α helical domain and wherein the mutation includes at least one of a mutation of residues E542, E545, or Q546 of the p110α helical domain.

3. The method of claim 1, wherein the cancer includes at least one of breast cancer, colon cancer, colorectal cancer, endometrial cancer, brain cancer, skin cancer, ovarian cancer, gastric cancer, lung cancer, thyroid cancer, head and neck cancer, cervical cancer, pancreatic cancer, esophageal cancer, liver/biliary cancer, tract cancer, pituitary tumors, urological tumors, leukemia/lymphoma, or neuroblastoma.

4. A method of treating cancer in a subject in need thereof, the method comprising:
    detecting the presence of mutant PIK3CA helical domain in cancer cells of the subject,
    administering to a subject having cancer cells with a mutant PIK3CA helical domain therapeutically effective amounts of (i) an EZH inhibitor in combination with (ii) Alpelisib, wherein the EZH inhibitor is tazemetostat (EPZ-6438, CAS No. 1403254-99-8) or GSK126 (GSK2816126, CAS No. 1346574-57-9).

5. The method of claim 4, wherein the PIK3CA helical domain mutant cancer includes a mutation in the p110α helical domain and wherein the mutation includes at least one of a mutation of residues E542, E545, or Q546 of the p110α helical domain.

6. The method of claim 4, wherein the cancer includes at least one of breast cancer, colon cancer, colorectal cancer, endometrial cancer, brain cancer, skin cancer, ovarian cancer, gastric cancer, lung cancer, thyroid cancer, head and neck cancer, cervical cancer, pancreatic cancer, esophageal cancer, liver/biliary cancer, tract cancer, pituitary tumors, urological tumors, leukemia/lymphoma, or neuroblastoma.

* * * * *